(12) United States Patent
Harweger et al.

(10) Patent No.: US 11,314,213 B1
(45) Date of Patent: Apr. 26, 2022

(54) AUTONOMOUS CROP DRYING, CONDITIONING AND STORAGE MANAGEMENT

(71) Applicant: HABER TECHNOLOGIES, INC., Ames, IA (US)

(72) Inventors: Eric G. Harweger, Ames, IA (US); Dillon G. Hurd, Ames, IA (US)

(73) Assignee: HABER TECHNOLOGIES, INC., Ames, IA (US)

( * ) Notice: Subject to any disclaimer, the term of this patent is extended or adjusted under 35 U.S.C. 154(b) by 0 days.

(21) Appl. No.: 17/347,941

(22) Filed: Jun. 15, 2021

(51) Int. Cl.
  *F26B 9/06* (2006.01)
  *G05B 13/04* (2006.01)
  (Continued)

(52) U.S. Cl.
  CPC ............ *G05B 13/048* (2013.01); *A01F 25/22* (2013.01); *F26B 9/063* (2013.01); *G01K 13/00* (2013.01);
  (Continued)

(58) Field of Classification Search
  CPC ....... G05B 13/048; A01F 25/22; G01K 13/00; G01N 33/0098; G01N 2033/245; G06Q 30/0201
  See application file for complete search history.

(56) References Cited

U.S. PATENT DOCUMENTS

| | | |
|---|---|---|
| 4,253,244 A | 3/1981 | Kranzler |
| 4,583,300 A | 4/1986 | Mast |

(Continued)

FOREIGN PATENT DOCUMENTS

| | | |
|---|---|---|
| CA | 2885751 A1 | 9/2016 |
| CN | 201919594 U | 8/2011 |

(Continued)

OTHER PUBLICATIONS

Xueqiang Liu, Xiaoguang Chen, Wenfu Wu, Guilan Peng, "A neural network for predicting moisture content of grain drying process using genetic algorithm," 2007, Science Direct, Food Control 18, pp. 928-933. (Year: 2007).*

(Continued)

*Primary Examiner* — Mohamed Charioui
*Assistant Examiner* — Christine Y Liao
(74) *Attorney, Agent, or Firm* — Lazaris IP, Inc.

(57) ABSTRACT

A post-harvest crop management platform is provided for regulating conditions of an agricultural crop being dried and/or stored. The platform utilizes data collected from sensors positioned proximate to, or embedded within, an agricultural crop, and analyzes selected crop characteristics affecting the stored crop in multiple sections thereof. The platform identifies parameters relative to achieving a desired crop characteristic level in the agricultural crop, generates a profile of the selected crop characteristic across the multiple sections of the stored crop, and models an application of a fluid flow pattern to achieve the desired crop characteristic level in each section. The crop storage monitoring and management platform also actuates a multi-stack assembly, configured within the stored crop, to automatically apply the fluid flow pattern in one or more cycles that are adjustable to changing conditions within the stored crop in real time. The crop storage monitoring and management platform further integrates with, and connects to and communicates with, other systems within an autonomous field activity ecosystem.

30 Claims, 19 Drawing Sheets

(51) Int. Cl.
| | |
|---|---|
| *G06Q 30/02* | (2012.01) |
| *G01N 33/00* | (2006.01) |
| *G01K 13/00* | (2021.01) |
| *A01F 25/22* | (2006.01) |
| *G01N 33/24* | (2006.01) |

(52) U.S. Cl.
CPC ..... *G01N 33/0098* (2013.01); *G06Q 30/0201* (2013.01); *G01N 2033/245* (2013.01)

(56) References Cited

U.S. PATENT DOCUMENTS

| | | | |
|---|---|---|---|
| 4,688,332 | A | 8/1987 | Kallestad et al. |
| 5,957,773 | A * | 9/1999 | Olmsted ............ A01D 41/1272 460/7 |
| 6,530,160 | B1 * | 3/2003 | Gookins ................ F26B 25/22 34/418 |
| 6,986,294 | B2 | 1/2006 | Fromme et al. |
| 7,818,894 | B2 | 10/2010 | Noyes et al. |
| 9,347,904 | B1 | 5/2016 | Schaefer, Jr. |
| 9,551,737 | B2 | 1/2017 | Bloemendaal et al. |
| 9,714,790 | B2 | 7/2017 | Bartosik et al. |
| 10,496,113 | B2 | 12/2019 | Boisjoli |
| 10,614,403 | B2 | 4/2020 | Kaloudis et al. |
| 2010/0250017 | A1 | 9/2010 | Kallestad |
| 2014/0172360 | A1 | 6/2014 | Folk |
| 2014/0250717 | A1 * | 9/2014 | Bloemendaal ........ F26B 25/002 34/487 |
| 2015/0354895 | A1 * | 12/2015 | Bloemendaal .......... F26B 21/12 34/495 |
| 2016/0054058 | A1 * | 2/2016 | Pauling ............... F26B 17/1408 34/235 |
| 2017/0346953 | A1 | 11/2017 | Abassi |
| 2019/0018378 | A1 | 1/2019 | Varikooty et al. |
| 2019/0265082 | A1 | 8/2019 | Zafar et al. |
| 2020/0263923 | A1 | 8/2020 | Bloemendaal |

FOREIGN PATENT DOCUMENTS

| | | |
|---|---|---|
| CN | 101919330 B | 2/2012 |
| CN | 102379195 A | 3/2012 |
| CN | 102283283 B | 5/2013 |
| CN | 203133641 U | 8/2013 |
| CN | 203181630 U | 9/2013 |
| CN | 104237056 B | 9/2016 |
| CN | 107166663 A | 9/2017 |
| CN | 109375531 A | 2/2019 |
| CN | 107246715 B | 5/2020 |
| CN | 111642256 A | 9/2020 |
| CN | 112136519 A | 12/2020 |
| CN | 212108909 U | 12/2020 |
| CN | 109186239 B | 2/2021 |

OTHER PUBLICATIONS

Dr. Keller Sullivan Oliveira Rocha, José Helvecio Martins, Marcio Arêdes Martins, Jairo Alexander Osorio Saraz &Adílo Flauzino Lacerda Filho, Three-Dimensional Modeling and Simulation of Heat and Mass Transfer Processes in Porous Media: An Application for Maize Stored in a Flat Bin, Drying Technology, Jun. 27, 2013.

M. Esther Magdalene Sharon, C.V. Kavitha Abirami and K. Alagusundaram, Grain Storage Management in India, Journal of Postharvest Technology, Jan. 31, 2014.

Temesgen Belay Tedla et al., Automated Granary Monitoring and Controlling System Suitable for the Sub-Saharan Region, International Journal of Scientific & Technology Research, vol. 8, Issue 12, p. 1943-1951, Dec. 1, 2019.

Post-Harvest Monitoring Stored Grain web article; Source: https://nuseed.com/us/post-harvest-monitoring-stored-grain/ Date Originally Accessed: Apr. 29, 2021.

Grain Monitoring System web article; Source: https://www.gescaser.com/grain-monitoring-system/ Date Originally Accessed: Apr. 29, 2021.

Grain web article; Source: https://crop-protector.com/products/ Date Originally Accessed: Apr. 29, 2021.

Agrolog Tms6000 web article; Source: https://www.agrolog.io/agrolog-tms6000 Date Originally Accessed: Apr. 29, 2021.

* cited by examiner

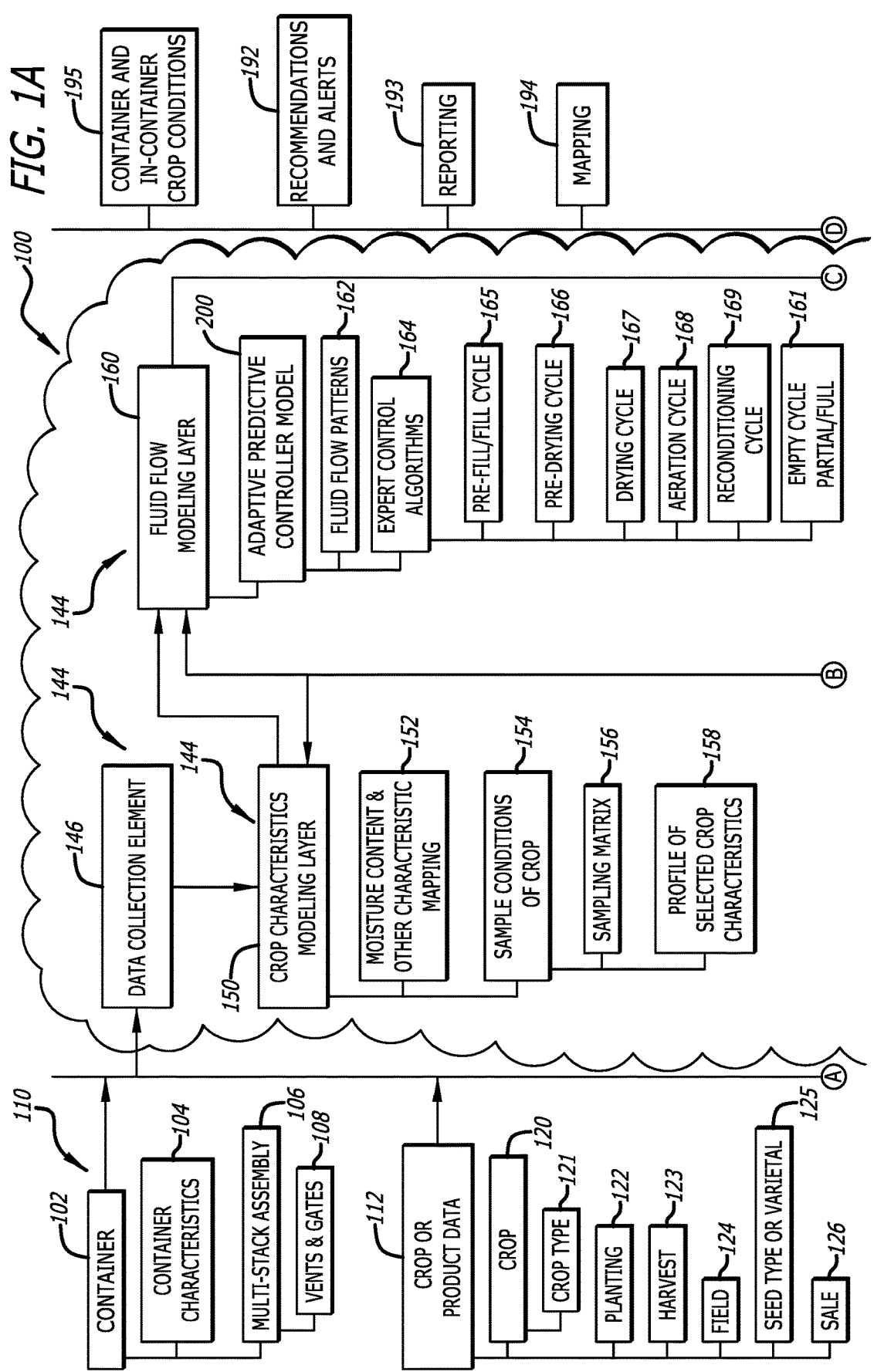

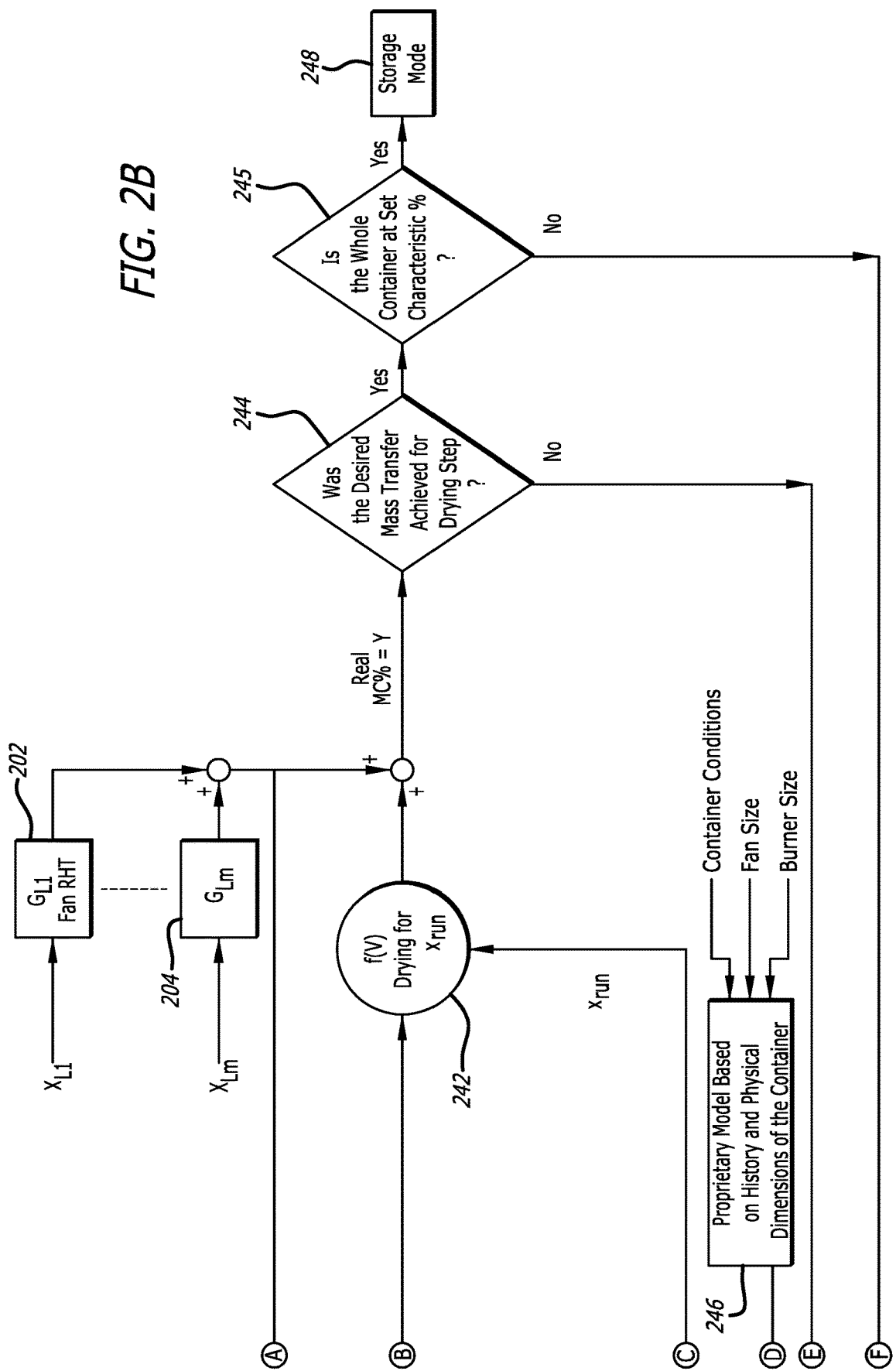

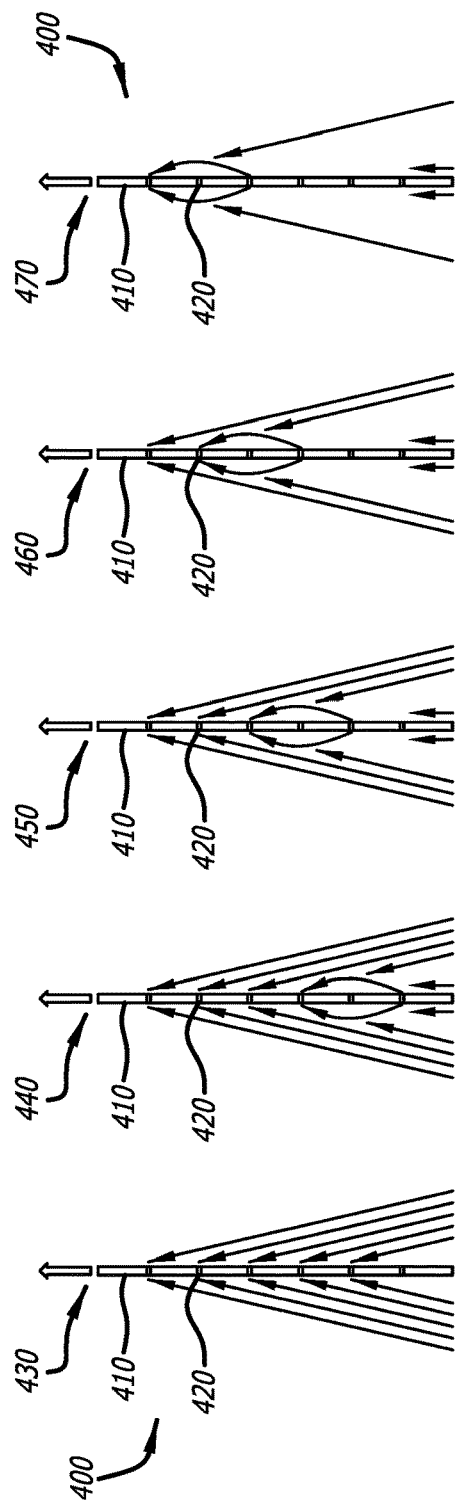
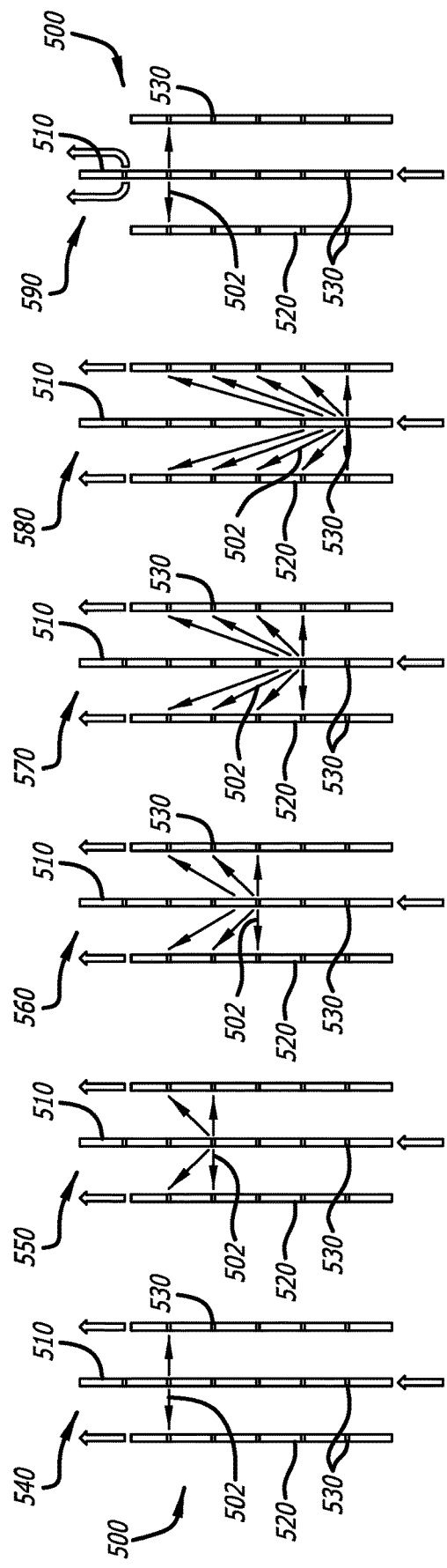

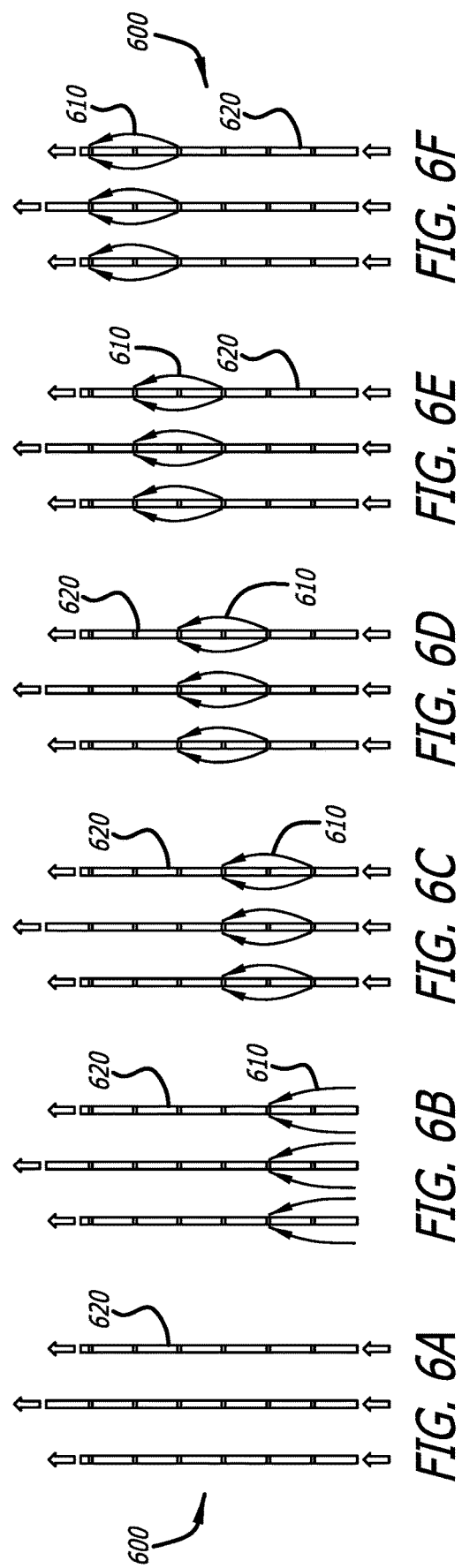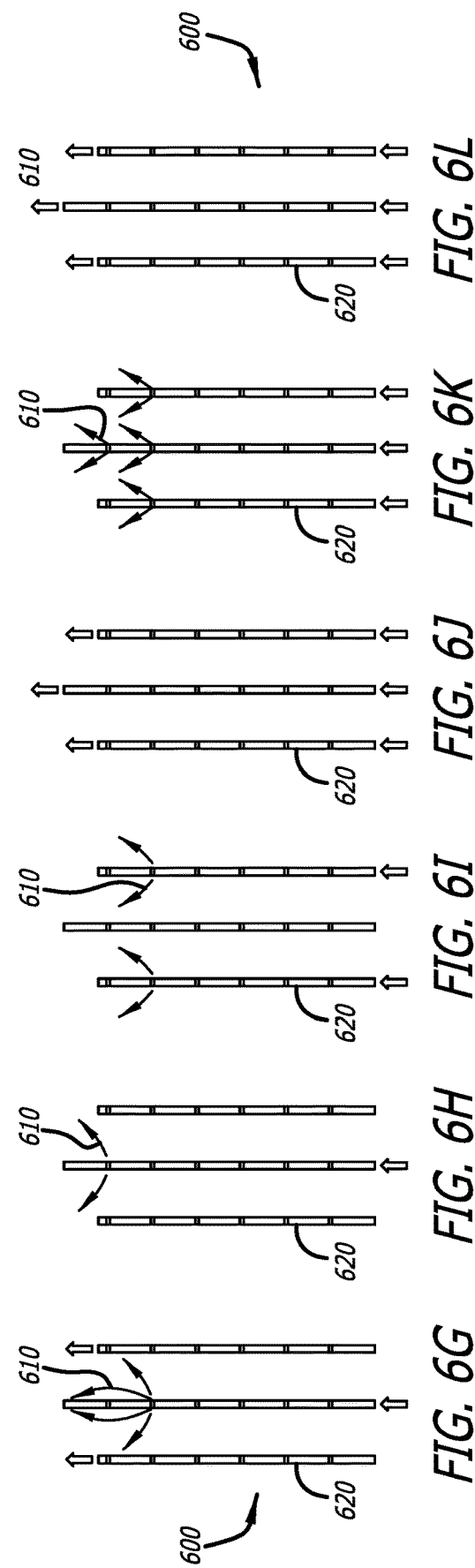

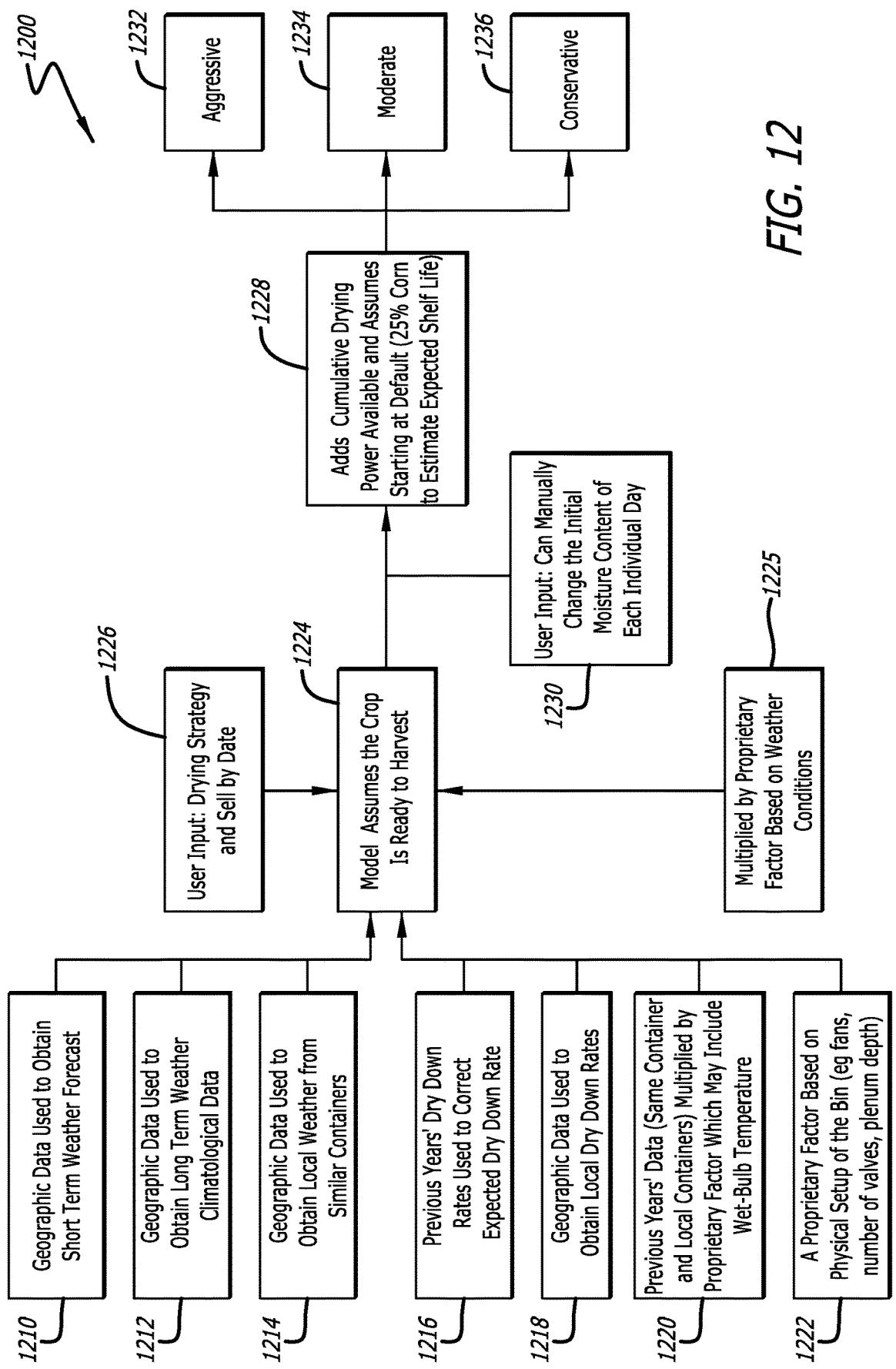

AUTONOMOUS CROP DRYING, CONDITIONING AND STORAGE MANAGEMENT

CROSS-REFERENCE TO RELATED PATENT APPLICATION(S)

Not applicable.

FIELD OF THE INVENTION

The present invention relates to precision agriculture. Specifically, the present invention relates to analyzing data relative to an agricultural crop collected from sensors within crop storage containers, and modeling both characteristics of the crop and flow patterns for delivering air or other fluid to the crop on a section-by-section basis stored in such containers to achieve desired crop and/or storage characteristics, in one or more autonomous crop drying, conditioning and storage management functions.

BACKGROUND OF THE INVENTION

In most existing commercial grain drying systems applied in large-scale and/or bulk grain containers, conditions within a stored crop are regulated by pushing in ambient air from the bottom of the container, and this may be heated on occasion to dry the stored crop. This, however, results in uneven drying across all sections of the stored crop, and creates inconsistent or otherwise undesirable moisture and temperature conditions throughout the various sections of the crop within the container.

Such problems occur at least because of the physical nature of the way crops are situated when inside a container. For example, grains are packed much more tightly in central sections of a container, while at perimeter sections, or near a headspace or top, they are packed much less densely. Similarly, the mechanics of conventional grain-drying systems, where heat is applied from a bottom area of a container referred to as a plenum, mean that more heat is received in sections of the stored crop nearer to the source of such heat. Any air in such conventional systems, whether ambient, heated, or cooled, has a decreasing ability to penetrate sections of the crop, and affect grain characteristics such as moisture and temperature, that are further and further away from the source.

Such problems may have numerous deleterious impacts on the stored crop over time, and in particular, on the quality of the crop at the time it is removed from the container for sale. Damage, for example due to spoilage, may often occur because of overly moist conditions within the container due to under-drying, and such damage may cause severe losses for growers or sellers. Under-drying often occurs on top and within the central core of a stored crop. Conversely, over-drying of a crop within a container may result in stress cracking and may be exasperated by heat damage, which often occurs at the bottom of a container, near the source of the air and heat.

There are no existing, commercial grain-drying systems which attempt to address grain conditions during storage on a section-by-section basis, which also apply fluids (whether they be heated air, ambient air, gases, liquids, or any other treatment applied to crops) from areas other than the plenum. Additionally, there are no in-container drying systems which apply advanced analytical models to assess conditions within the stored crop in real-time, while drying is occurring, and on a section-by-section basis, to deliver fluids and to adjust the delivery of fluids in a section-by-section approach and minimize the potential for losses that are often incurred by conventional systems. Still further, there are no in-container drying systems which include elements of machine learning and artificial intelligence within such advanced analytical models for assessing conditions within the stored crop in real-time, while drying is occurring, and on a section-by-section basis, to predict future crop conditions, and determine and adjust the delivery of fluids in a section-by-section approach based on such predictions.

Additionally, there are no existing assemblies for grain-drying systems that employ such a section-by-section approach in multi-stack assemblies where fluids are transferred between open vents, whether along the same stack or across different stacks positioned within the container at different sections of the stored crop. Still further, there are no existing assemblies for grain-drying systems that employ such a section-by-section approach in multi-stack assemblies to influence airflow around vents by, for example, either pushing air out into the grain, providing a path for the air into the stack, or both, and creating sections of high and low pressure within the stored crop to improve airflow therein, to regulate in-container crop conditions on a section-by-section basis, and which apply such advanced analytical models, whether they are applied together with elements of machine learning and artificial intelligence or otherwise, to perform real-time assessments and actuate the multi-stack assemblies to regulate in-container conditions and achieve target crop characteristics at a future time.

Thousands of conventional systems, in which ambient (and heated) air is pulled through the plenum, and in which the stored crop is treated as a single grain mass for drying and conditioning, continue to be installed and used today throughout the world, resulting at least in continuing inefficiencies and damage to stored crops. Accordingly, there is a need in the existing art for grain-drying systems which overcome these issues and problems, and effect drying of a stored crop in manner which preserves the quality and value of the stored crop until the time of unloading and sale.

BRIEF SUMMARY OF THE INVENTION

The present invention is applicable in precision agricultural situations where grains and other crops, which may be collectively referred to herein as agricultural crops, stored crops, or simply crops, are stored in containers. The present invention performs autonomous crop drying, conditioning and storage management within a post-harvest crop management platform that assesses the moisture content, temperature, or other characteristics of the crop at different levels and sections throughout a container, and dries, aerates, conditions, transfers, and manages the quality of the crop by efficiently applying ambient air, supplemental heat, gas, or other fluid. The post-harvest crop management platform is performed, in accordance with one embodiment of the present invention, in conjunction with an assembly comprised of one or more stacks configured within the container to regulate conditions within the entire container in a section-by-section manner. Alternatively, the present invention may be performed independent of any specific hardware assembly as a stand-alone software application.

The post-harvest crop management platform utilizes data collected from at least one of user inputs, a plurality of sensors that are either positioned proximate to, or embedded within, a crop, and a plurality of sensors inside or proximate to a container holding the crop, and analyzes at least this data to regulate one or more selected crop characteristics affecting the crop in the multiple sections thereof. This is accomplished by sampling conditions of the crop to identify parameters relative to a desired crop characteristic level, generating a profile of the selected crop characteristic across the multiple sections of the crop in the container, modeling an application of a fluid flow pattern to the crop across each section of the container to achieve the desired crop characteristic level, and executing commands to actuate the multi-stack assembly in such a manner as to carry out and apply an appropriate fluid flow pattern. Such modeling may further include an application of machine learning, configured to predict at least a mass transfer across the multiple sections of the crop, based on one or more inputs derived from at least one sampling matrix. The crop storage management platform may be thought of, in one aspect of the present invention, as a fill, set and Forget™ (and/or simply a fill-and-Forget™) system for the drying, storing and further conditioning of any crop. Such a fill, set and Forget™/fill-and-Forget™ system is applicable to any agricultural product derived from plants, regardless of whether it is grains, legumes, seeds, nuts, leaves, stalks, flowers, or any other type.

Such a fill, set and Forget™/fill-and-Forget™ system has as a central concern the storage of agricultural crops, but it is to be understood that the crop storage management platform of the present invention is, more broadly, an element within the precision agriculture ecosystem that easily integrates with multiple other systems that together constitute autonomous field (or farm operation) activities, as well as with other autonomous operations and activities that extend beyond just field and farm, such as for example the coop environment and the transportation and shipping industries, and still further, to derivative elements such as insurance and finance. The crop storage management platform therefore connects and communicates with other precision agriculture implements that act as both inputs for the present invention, and outputs for the present invention. In addition, the crop storage management platform of the present invention may itself serve as a set of inputs to other precision agriculture systems, and to other systems outside the field of agriculture, and may be part of output use-cases for other such systems.

The present invention may be further considered as, in another aspect thereof, applying a 'whole-container' approach to crop storage in which crop characteristics are analyzed on a segmented or even micro basis to achieve a greater understanding of issues affecting crop quality throughout the entire container. Such a whole-container approach models crop characteristics through an understanding that different factors influence crop conditions in different sections of a crop, and that parameters for modeling such factors may be different in each section and at different times. Such a whole-bin approach therefore evaluates the entire container by examining the crop according to multiple segments thereof, as a collection of smaller and varied ecosystems within the same container, rather than regarding conditions with the container as universally the same.

It is one objective of the present invention to provide systems and methods of regulating one or more selected characteristics of an agricultural crop. It is another objective of the present invention to provide systems and methods of regulating one or more selected characteristics of the agricultural crop by sampling and modeling conditions of the agricultural crop within a container. It is another objective of the present invention to provide systems and methods of modeling fluid flow patterns for delivery of fluid to an agricultural crop to achieve a desired crop characteristic level. It is yet another objective of the present invention to provide systems and methods of actuating a multi-stack assembly, configured within such a container, to achieve the desired crop characteristic level. It is still another objective of the present invention to provide systems and methods of autonomously actuating such a multi-stack assembly to achieve desired crop characteristic levels across each section of an agricultural crop stored in a container. It is still a further objective of the present invention to provide a software system for regulating the one or more selected characteristics of an agricultural crop that easily integrates with multiple other systems that together constitute autonomous field or farm operations and activities in the precision agriculture sector.

Other objectives, embodiments, features, and advantages of the present invention and its embodiments will become apparent from the following description of the embodiments, taken together with the accompanying drawings, which illustrate, by way of example, principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

FIGS. 1A-1B are system diagrams illustrating elements of a post-harvest crop management platform of the present invention;

FIGS. 2A-2B are block diagrams and flow charts illustrating elements of an adaptive predictive controller model within the post-harvest crop management platform of the preset invention, according to an embodiment thereof;

FIGS. 4A-4E is an exemplary illustration of fluid flow patterns delivered from a multi-stack assembly by executing one or more control algorithms in the post-harvest crop management platform of the present invention, according to another embodiment thereof;

FIGS. 5A-5F is another exemplary illustration of fluid flow patterns delivered from a multi-stack assembly by executing one or more control algorithms in the post-harvest crop management platform of the present invention, according to another embodiment thereof;

FIGS. 6A-6L is another exemplary illustration of fluid flow patterns delivered from a multi-stack assembly by executing one or more control algorithms in the post-harvest crop management platform of the present invention, according to another embodiment thereof;

FIG. 12 is a block diagram and flow chart illustrating analytics performed within the post-harvest crop management platform of the present invention and generation of weather recommendations in an output use case thereof.

DETAILED DESCRIPTION OF THE INVENTION

Figure 1B:
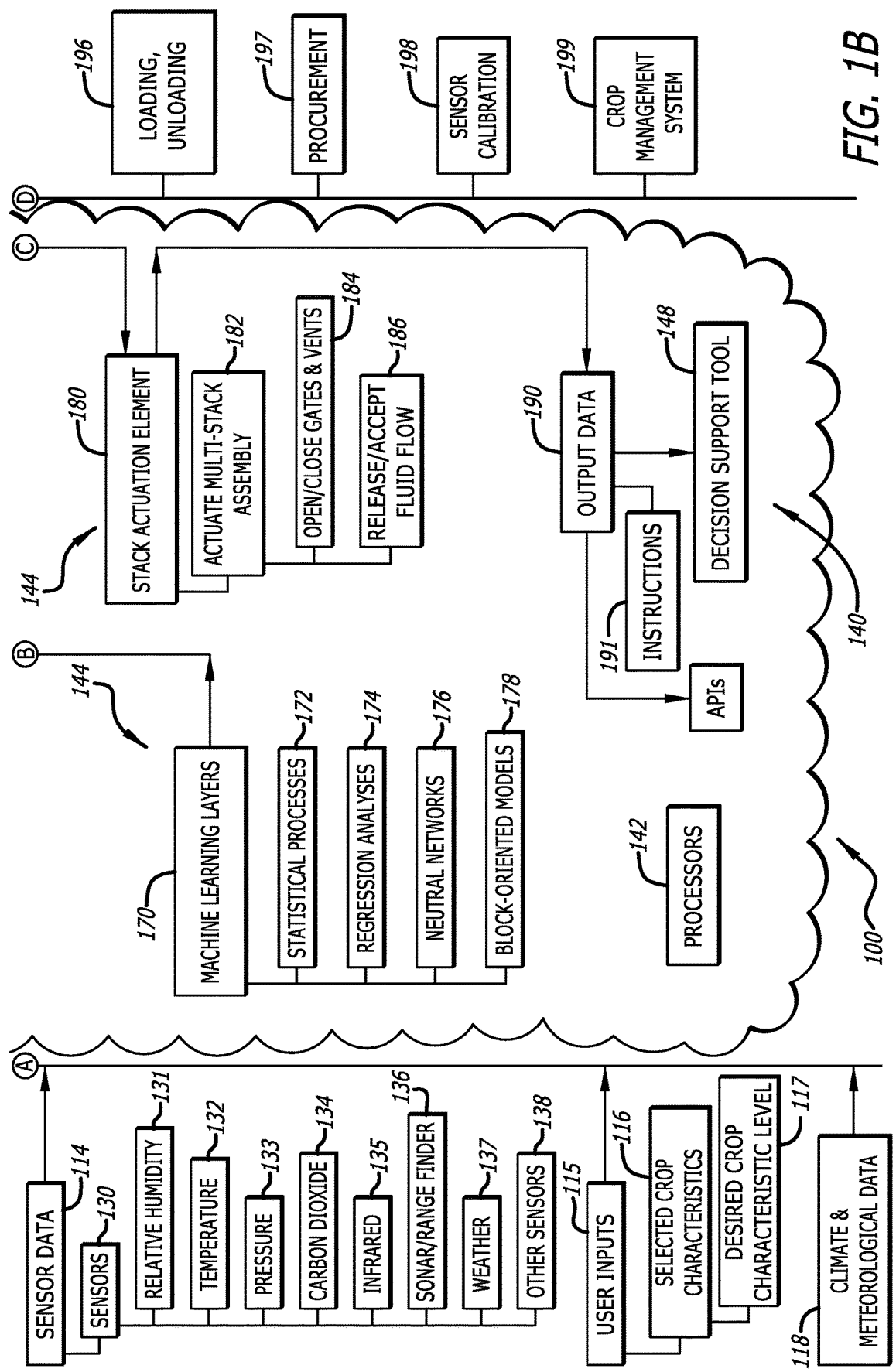

In the following description of the present invention, reference is made to the exemplary embodiments illustrating the principles of the present invention and how it is practiced. Other embodiments will be utilized to practice the present invention and structural and functional changes will be made thereto without departing from the scope of the present invention.

It is to be understood at the outset that, though the present invention may be styled herein as a post-harvest crop management platform, many other attributes of such a platform are possible, whether the present invention is part of other systems that constitute autonomous field or farm operation activities or that involve other autonomous operations and activities that extend beyond such field or farm operations or activities, or whether the present invention is self-contained. The post-harvest crop management platform may therefore manage at least drying and re-conditioning of stored crops, and therefore neither this detailed description, the accompanying figures, or the claims shall be limited to any one type of post-harvest management of crops with such a platform.

Still further, it is to be understood that the post-harvest crop management platform may be embodied as either a stand-alone software application as noted above, or as a combined implementation that may be performed in a conjunction with hardware elements, such as those installed within or otherwise configured with a container 102. Therefore, although the present invention may include actuation of a multi-stack assembly 106 in one or more embodiments described herein, the post-harvest crop management platform is independent of any hardware. Where performed with hardware elements, the present invention is agnostic as to such hardware, such that the post-harvest crop management platform may be performed with any hardware implementation, whether comprised or multiple stacks, single stacks, or no stacks at all.

The present invention is a post-harvest crop management platform 100 that is provided in one or more systems and methods for, in one aspect thereof, regulating crop characteristics affecting a storage of a crop 120 within a container 102, as part of multiple autonomous crop drying, conditioning and storage management functions as described in detail herein. The post-harvest crop management platform 100 includes, in one aspect of the present invention, a modeling framework comprised of multiple elements and layers that execute a plurality of algorithms that include an adaptive predictive controller model 200 for mapping characteristics 152 of a crop 120 within a container 102, and for developing fluid patterns 162 based on the mapped characteristics 152 and the adaptive predictive controller model 200, using input data 110 that is, at least in part, collected from different types of sensors 130 that are either proximate to, or embedded within, the crop 120.

The post-harvest crop management platform 100 processes input data 110 that includes both agricultural crop or product data 112 and sensor data 114 collected from one or more of such sensors 130, as well as other relevant information either provided as user inputs 115, or provided by third-parties or collected from additional data sources such as for example climate and meteorological data 118. The modeling framework that analyzes this input data 110 includes a crop characteristics modeling layer 150, a fluid flow modeling layer 160, and in some embodiments of the present invention, one or more machine learning layers 170 that apply proprietary techniques of machine learning to enhance a profile 158 of selected crop characteristics 116, and improve fluid flow patterns 162 developed based on such a profile 158, for regulating the selected crop characteristics 116 affecting storage of the crop 120 within the container 102.

FIGS. 1A-1B & 2A-2B

FIGS. 1A-1B are systemic, high-level block diagrams showing various elements comprising the post-harvest crop management platform 100 according to one aspect of the present invention. The post-harvest crop management platform 100 is embodied within one or more systems and/or methods that are performed in a plurality of data processing elements 144 that are components within a computing environment 140 that also includes one or more processors 142 and a plurality of software and hardware components. The one or more processors 142 and plurality of software and hardware components are configured to execute program instructions or routines to perform the modules, components, and data processing functions described herein, and embodied within the plurality of data processing elements 144.

The post-harvest crop management platform 100 includes a data collection element 146, embodied in one or more algorithms configured to ingest, receive, request, or otherwise obtain input data 110, which includes many types of information relative to a stored crop 120 to be analyzed. This input data 110 includes, as noted above, agricultural crop-related or product-related data 112 that defines the crop 120, sensor data 114, container-specific data such as container characteristics 104, climate and meteorological data 118, and other information, either provided as user inputs 115, collected by various sensors 120 or other Internet-of-Things (IoT) devices (for example, data collected from devices installed on board harvesting or other farm equipment or machinery), or provided by additional third parties or obtained from additional data sources. Each of these sources include different types of information and are used in the post-harvest crop management platform 100 to analyze multiple sections of the crop 120 within the container 102, model fluid flow patterns 162, and actuate a multi-stack assembly 182 having a plurality of stacks 184 to regulate conditions affecting a storage of the crop 120 in the multiple sections within the container 102 to achieve a desired crop characteristic level 117.

The selected crop characteristic(s) 116 to be analyzed may be provided, as noted above, as a user input 115. Other user inputs 115 may include one or more additional parameters, for example anticipated crop removal or sell dates defining a temporal limit on the storage of the crop 120, and parameters for the desired crop characteristic level 117. Such parameters may include, for example where the selected crop characteristic 116 is moisture content, one or more moisture content set points, such as an initial moisture content value or anticipated starting crop characteristic level, a storage moisture content value comprising a less perishable crop characteristic level, and a market moisture content value comprising a crop characteristic level fit for sale. Still further, user inputs 115 may include information such as the amount of the crop 120 harvested. User inputs 115 may also include, as noted above, crop or product data 112, and climate and meteorological data 118. Regardless of the type of information contained therein, the user inputs 115 may be generated by user, for example using a decision support tool 148, or may be determined automatically from one or more of the other inputs provided to the modeling framework within the post-harvest crop management platform 100.

Crop and/or product data 112 includes many types of information defining the crop 120. Such information may be both historical in nature (for prior growing seasons or off-seasons) or current in nature (for current growing seasons or off-seasons). Such information may include a crop type 121, planting information 122, and harvest information 123. It may further include a location 124 of the crop 120, such as for example geo-positional coordinates of a field or management zone in which the crop was grown, and any other information that identifies a specific field or management zone and any relevant characteristics of such a location. Still further, the crop and/or product data 112 may include information such as a seed type or varietal 125, including a seed year, as well as any treatments or nutrients applied to the crop or soil either before, during, or after the growing season, and soil characteristics for the soil in which the crop 120 was planted. Treatments and nutrients may include any organic or non-organic products, either naturally occurring or synthetic, that have an impact on plants, crops, soils, or fields. Crop data 112 may also include information about off-season crops grown in the same or similar fields, and other farm and field management information, regardless of any temporal element to such information, such as for example crop rotation information, tillage activities, irrigation information, and nutrient levels.

Containers 102 within which crops 120 are maintained and stored are often referred to as grainware and may include any type of structure configured to hold, or warehouse, crops 120 in bulk. Examples of containers 102 include bins, tower silos, bunker silos, hoppers, piles, silo bags, and bulk bags, and may be made of many types of materials and have many shapes and sizes. Containers 102 may further include both fixed, or stationary structures, and mobile structures, and the post-harvest crop management platform 100 (and multi-stack assemblies 106 in communication therewith) may be configured within any such fixed or mobile structure. For example, the present invention may be configured with containers 102 used in shipping, such as road containers for trucks or rail containers for trains, or in bulk holding tanks of commercial vessels for ocean, sea, or other waterway shipping. Many examples of containers 102 are possible, and therefore it is to be understood that any type of container 102 in which a crop 120 may be held is within the scope of the present invention, and that neither this specification nor the claims shall be limited to any specific type of container 102 discussed herein.

A container 102 may be either closed or semi-closed, and may have either a hard structure, a soft structure, or both. Containers 102 typically include a bottom, and walls, and may include a top such as a roof, or a lid, and such roof may have a conical shape; regardless, it is to be understood that containers 102 may have any configuration and any shape suitable for storing a crop 120 therein. Characteristics such as materials of construction, size, and shape may impact storage conditions within the container 102, and therefore the input data 110 may also include characteristics 104 of containers 102. Such characteristics 104 may include, as noted above, a container type, the materials used in construction of the container, and configuration information such as height, width, shape, and other dimensions. Other container characteristics 104 may include the number, position, maintenance status, speed, and type of fans installed in a container, auger characteristics such as speed, type, and configuration for loading and unloading, ventilation characteristics, container capacity, cleaning history, the geographical location of the container, and other characteristics 104 which may be relevant to maintenance and storage of a crop 120 therein.

As noted above, many different types of sensors 130 may be utilized to collect and provide sensor data 114 in the post-harvest crop management platform 100 of the present invention, and these sensors 130 may be placed at many different places throughout a container 102, either within, proximate to, or separate from the crop 120 stored therein. Sensors 130 may include relative humidity sensors 131, temperature sensors 132, pressure sensors 133, carbon dioxide ($CO_2$) sensors 134, infrared sensors 135, sonar/ranging sensors 136, weather sensors 137, and any other sensors 138 that can be utilized to discern conditions within either a crop 120 or a container 102, or both.

Such sensors may be placed anywhere and at any time within a crop 120 or a container 102. For example, relative humidity sensors 131 and temperature sensors 132 may each be positioned with any of the influent space or plenum of a container 102, the crop 120 itself, and effluent area or headspace of a container 102. $CO_2$ sensors 134, and infrared sensors 135 may each be positioned in the effluent area or headspace, while pressure sensors 133 may be positioned in the influent space or plenum. Sensors 130 may also be placed adjacent to, or proximate to, any of these areas.

Other sensors 138 may include sensors that provide hardware-specific information to the modeling framework of the present invention. For example, the sensors 130 may include specific in-line pressure sensors to monitor health and performance of a pneumatic control system for actuating a multi-stack assembly 106. For example, a feed pressure sensor may be utilized to monitor feed pressure of the multi-stack assembly 106, because it indicates that the assembly's compressor is on and working, and feed helps to determine if a valve may be opened. Feed pressure should be within a specified range, and if pressure is not quickly stabilized, an alert and may be generated with an indication that the compressor might need repair or replacement or change. Also, an exhaust pressure sensor may be utilized to ensure proper functioning of the cylinders in the multi-stack assembly 106. An exhaust pressure should have a normal value that is the average of the release pressures seen during a successful system test. Abnormal readings suggest a change of desiccant may be needed within the container 102, and an alert may be generated suggesting such a change. Other sensors 138 may be included in the present invention to monitor fluid flow pressure, and pressure on the stacks themselves.

Other sensors 138 may also include amperage sensors which may also be useful in monitoring health and performance of the pneumatic control system for actuating a multi-stack assembly 106. Amperage sensors may include sensors for monitoring an amperage of the compressor that enables a check for errors in readings of the feed and exhaust pressures. Amperage of the compressor also enables a calculation of a cost to dry a bushel or section of a crop 120 stored in the container 102, as does a control box amperage sensor. Yet another sensor monitors an amperage of solenoids to read the amps that are drawn when a solenoid is switched on to confirm that it is electrically functional. Still other sensors monitor an amperage of central processing units (CPUs), graphics processing units (GPUs), or other processors involved in actuating a multi-stack assembly 106. Yet another sensor monitors an amperage of the fan or fans to determine and confirm with a pressure sensor of the influent or plenum which may further enable a calculation of a cost to dry a bushel or section of a crop 120 stored in the container 102.

Climate and meteorological data 118 also includes many different types of information. For example, climate and meteorological data 118 ingested into the post-harvest crop management platform 100 may include real-time (current), historical (past), and forecasted or predicted (future) field-level data representative of assessments of weather conditions, either localized to a specific geographical area (for example, to the geo-positional coordinates representing the location of the container 102 (provided, for example, in the container characteristics 104) or for more broadly-defined geographical areas). Such field-level data representative of assessments of weather conditions may be produced by many different sources of meteorological data to provide current field-level weather data, historical weather data, forecasted or predicted weather data (such as information provided in long-range climatological and/or meteorological forecasting from predictive weather models), and observed weather data such as data from both in-situ and remotely-sensed observation platforms, or provided by a weather sensor 137. Weather information may also be combined, for example from existing weather prediction models or historical data, with data from weather radar systems and satellites to reconstruct the current or previous weather conditions on any particular area to be analyzed. It is to be understood that the present invention may be configured to ingest climate and meteorological data 118 from many sources, regardless of whether they be publicly or privately provided, or internally developed.

Input data 110 may also include other information such as data collected from sensors 130 or other devices, whether affixed or coupled to particular objects or positioned in or near particular areas, in an Internet-of-Things environment (or other similar paradigms or approaches having similar names, such as the Internet-of-Farms, Internet-of-Plants, Internet-of-Crops, and Internet-of-Fields, etc.). For example, sensors 130 coupled to agricultural vehicles may collect crop-related and field-related data relative to conditions of a crop 120 as it is being harvested or transported, and transmit that information for collection and processing, which may be ingested into the post-harvest crop management platform 100 as input data 110. Other examples include soil sensors, Bluetooth™ components, and other devices which are able to acquire localized information that may be relevant to assessing conditions of a harvested (or about to be harvested) crop 120. Input data 110 may also include data collected from crowdsourcing observations, ground truth data, and other user- or individual-generated information, for example using dedicated applications on smart or mobile computing devices.

Still other types of input data 110 are possible and within the scope of the present invention. These may include image data, such as that collected by satellite systems, photography or video captured by remotely-piloted vehicles, commonly referred to as drones, or field-based robots configured to generate field-level images, such as those using in-field sensors. Manned and unmanned aerial reconnaissance craft may also be used to acquire image data for processing within the post-harvest crop management platform 100 of the present invention. Image data may be processed and utilized, for example, to discern and assess field utilization, and crop and plant growth, health, and any changes thereto over time, that later impact harvesting of the crop 120. Image data may be comprised, at least in part, of information in pixels representing different ranges of frequencies along the electromagnetic spectrum, for example where sensors configured with satellite systems include a multi-spectral instrument imaging system that captures and samples data in different spectral bands.

The present invention is, as noted above, a post-harvest crop management platform 100 that is provided in one or more systems and methods for, in one aspect thereof, utility in the process of mapping selected crop characteristics 116 within a container 102 and in modeling fluid flow patterns 162 from mapped characteristics 152. The post-harvest crop management platform 100 further includes one or more systems and methods that apply this mapping for the regulating crop characteristics to desired crop characteristic levels 117, by actuating multi-stack assemblies 106.

It is to be understood that the plurality of data processing elements 144 are, where applicable, also indicated in FIGS. 1A-1B by their specific, respective reference numerals as indicated below. It is to be further understood that these elements are components of the larger computing environment 140, and constitute one or more structures, hardware, firmware, middleware, or software such as algorithms, routines, sub-routines, and the like, that are specifically configured to execute particular functions within the post-harvest crop management platform 100. It is to be additionally understood that the data processing elements 144, and the respective elements of the present invention that together comprise these specifically-configured components, may interchangeably be referred to as "components," "modules," "algorithms" (where appropriate), "engines," "networks," and any other similar term that is intended to indicate an element for carrying out a specific data processing function.

The data processing elements 144 include, as noted above, a data collection element 146, which is configured to ingest, receive, request, or otherwise obtain input data 110, and to parse and initialize the various types of input data 110 in preparation for the functions performed in other data processing elements 144. Initialized input data 110 is then passed to the modeling framework of the post-harvest crop management platform 100 to analyze multiple sections of the crop 120 within the container 102, and multiple areas of the container 102 itself, for regulating the selected crop characteristic(s) 116.

The crop characteristic modeling layer 150 performs this analysis of the multiple sections of the crop 120 by running one or more sampling cycles to assess the one or more selected crop characteristic(s) 116. It is to be understood that a selected crop characteristic 116 may include moisture content, temperature, pressure, off-gassing or emission of carbon dioxide ($CO_2$) (for example, due to a presence of insects emitting $CO_2$), and any other characteristics that affect storage of the crop 120 within the container 102, and it is to be further understood that sampling cycles that analyze these characteristics are performed in conjunction with the expert control algorithms 164 of the fluid flow modeling layer 160, such that performance of the modeling framework described herein involves transmission or other transfer of data between the various data processing elements 144. Regardless, the crop characteristic modeling layer 150 applies one or more mathematical functions, algorithms, machine learning techniques, and other analytical approaches in an adaptive predictive controller model 200 (as discussed further with regard to FIGS. 2A-2B) which is configured to map the selected crop characteristic(s) 116 in the multiple sections of the crop 120 within the container 102 and generate a profile 158 of the selected crop characteristic(s) 116.

Mapping of selected crop characteristics 116 includes sampling conditions of the multiple sections of the crop 120 within the container 102 by analyzing sensor data 114. Where the selected crop characteristic 116 is moisture content, for example, the crop characteristic modeling layer 150 measures moisture content of the crop 120 for each section of the container 102 when it is full or partially full. Moisture content is calculated from measurements taken by the outputs of the relative humidity sensor 131 and the temperature sensor 132 as described further herein.

The post-harvest crop management platform 100 takes measurements from these sensors 130 by performing a sampling cycle that turns on fan(s), and sets open and close positions for all vents and gates 108, for the multi-stack assembly 106 for each test in the overall cycle. The post-harvest crop management platform 100 records the relative humidity and temperature for each section of the crop 120, calculates the average actual moisture content for each section, and records this information either to a local controller or processor, or within a cloud computing environment. The post-harvest crop management platform 100 then samples the ambient air temperature and relative humidity, and reports a calculated moisture content value for each section within the container 102, and constructs a sampling cycle matrix 156 for each test in addition to a test for a section around each stack. For example, for a six-stack three valve-assembly system, there could be at least twenty-four section-relative humidity records. This matrix serves as the profile 158 of the selected crop characteristic(s) 116, as well as an input to each drying cycle 167 in the fluid flow modeling layer 160.

The post-harvest crop management platform 100 creates matrices for each test, and includes data identifying respective vent and gate positions when measurements are taken. A section is considered to be the area of the crop 120 closest to the valve being utilized to convey the air from the crop 120 to a sensor within each particular container 102. This may also be configured to have multiple valves convey air to multiple sensors, wherein this would be considered to act as one section although said section with multiple valves could, either before or after, act as multiple sections, each valve conveying air for its own sample cycle.

More specifically, the post-harvest crop management platform 100 records relative humidity from the relative humidity sensor 131 mounted at or near the top, or exhaust, of each stack. The air going past the relative humidity sensor 131 is assumed to be the air that is coming out of the crop 120 in the section where the set of valves is open. A controller or processor logs the relative humidity from this section, and combines it with the temperature of the section in one or more mathematical processes to calculate the moisture content for that section, such as for example a modified Chung-Pfost equation.

The measurements of relative humidity and temperature are applied in such a modified Chung-Pfost equation together with several coefficients that may be changed in response to parameters such as the crop type 121, the seed type 125, the geographical location of the field 124 in which the crop 120 was grown, and the geographical location of the container 102. The modified Chung-Pfost equation is used to solve moisture content, and is derived as follows:

$$ERH = \exp\left[-\frac{A}{T+C}\exp(-B \times MC_D)\right]$$

$$MC_D = \frac{1}{B} \times \ln\left[-\frac{A}{(T+C) \times \ln(ERH)}\right]$$

where A, B, and C are coefficients as noted above, and moisture content, $MC_D$, is measured on a dry basis. Relative humidity is ERH and temperature is T.

The modified Chung-Pfost equation may be used to populate a look up table based on coefficients for commonly-stored crop types 121, frequently used seed varietals 125, and known locations of fields 124 and/or containers 102, and expected or historical measurements of both relative humidity and temperature. These inputs may also be provided electronically and/or automatically, for example as user inputs 115 or as data collected by devices affiliated with harvesting or other agricultural equipment, in an Internet-of-Things (IoT) environment. Regardless, the present invention may utilize the values stored in the look-up table for an estimate of moisture content each section, in addition to or instead of, an application of the modified Chung-Pfost equation in each instance.

The post-harvest crop management platform 100 may also generate and report a map of one or more of the relative humidity, the temperature, and the moisture content, in a visual representation of conditions within the container 102. Regardless, it is to be understood that the sampling cycle, and construction of a sampling cycle matrix 156, may be performed either before, during, or after a drying cycle 167 that is described further below, or after any cycle during which a crop 120 is in the container 102.

The post-harvest crop management platform 100 then takes the profile 158 of the selected crop characteristic(s) 116 and proceeds with developing fluid flow patterns 162 in the fluid flow modeling layer 160 of the modeling framework. This is done by modeling one or more ways of actuating the various hardware elements of the multi-stack assembly 106 to achieve a desired crop characteristic level 117 over the specified period of time, in an adaptive predictive controller model 200 (as discussed further with regard to FIGS. 2A-2B). The adaptive predictive controller model 200 analyzes possible fluid flow patterns 162 and configures a plurality of expert control algorithms 164 that execute one or more cycles that deliver the fluid flow patterns 162 to the crop 120 by actuating a plurality of vents and gates 108 in each stack of the multi-stack assembly 106, depending on the specific cycle performed.

The one or more cycles are applied by the adaptive predictive controller model 200 of the post-harvest crop management platform 100 to regulate conditions within the crop 120 while it is stored within the container 102 (or to facilitate such regulation), and are applied at different times based on a variety of factors. These factors at least include the current time period relative to the time period specified in the input data 110 between filling of the container 102 and removal of the crop 120 from the container 102, and the current conditions within the container 102 as determined by the crop characteristic modeling layer 150 or its output sampling matrix 156, represented by the profile 158 of the selected crop characteristic 116.

Figure 2A:
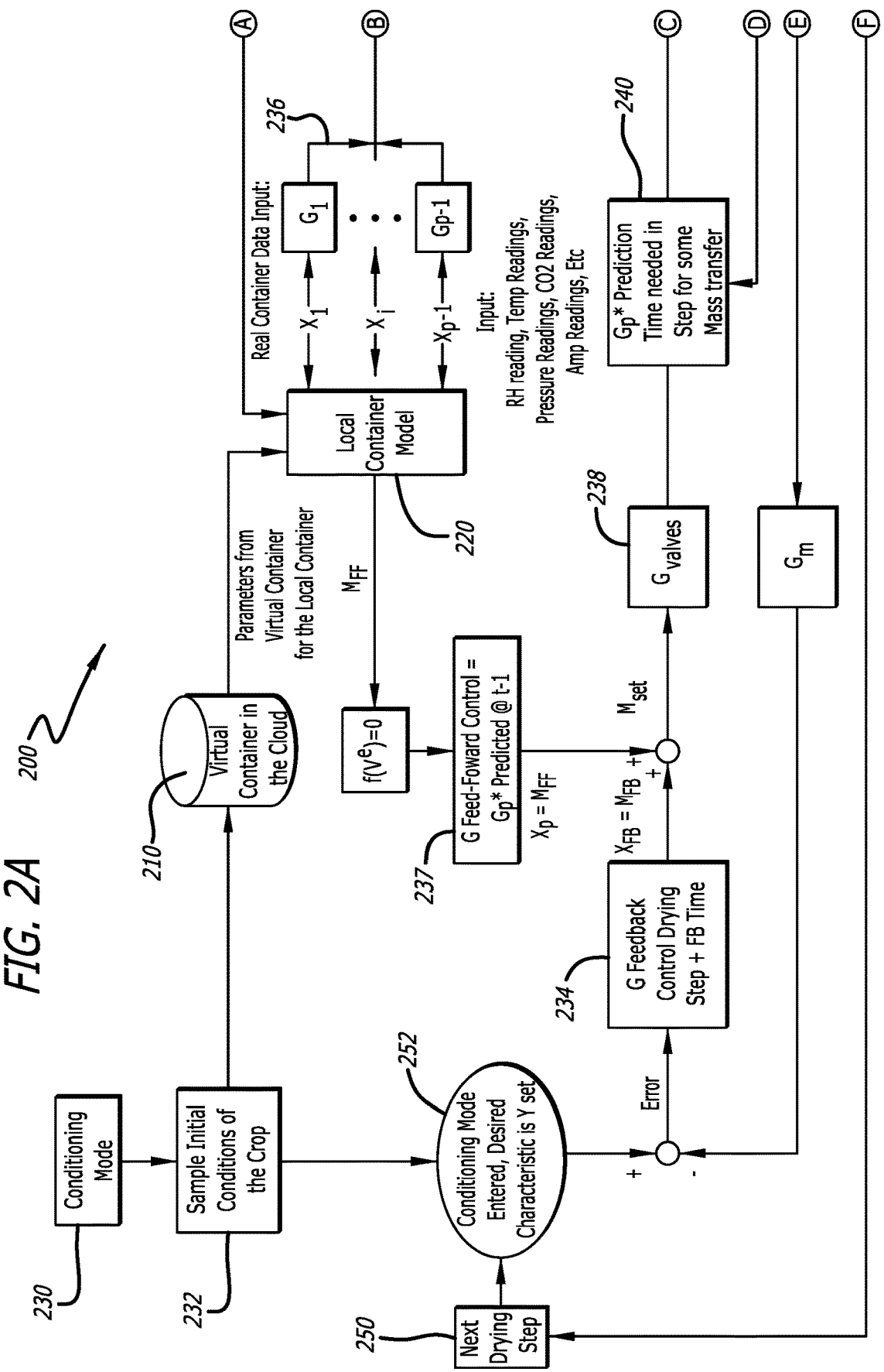

FIGS. 2A-2B are block diagrams and flow charts illustrating components of, and data flow within, the adaptive predictive controller model 200 of the post-harvest crop management platform 100. The adaptive predictive controller model 200 is process performed by at least one gateway or edge computer that integrate one or more Internet-of-Things (IoT) devices into an adaptive controller configured to control atmospheric conditions within a container 102 in one or more drying steps. The adaptive predictive controller model 200 combines a virtual container model 210 configured to find drying parameters, and a local container model 220, running on the at least one gateway or edge computer, to calculate drying times locally using the drying parameters identified by the virtual container model 210 along with a mass balance model which can be tuned and updated using one or more machine learning techniques as discussed herein. The virtual container model 210 may be performed as either a cloud-based model, or on an on-site or otherwise local machine, for example one dedicated to modeling characteristics of a commodity at a seed facility.

The adaptive predictive controller model 200 may be initiated when one or more conditioning modes as discussed herein with regard to FIGS. 8A-8D are entered at step 230 and a desired crop characteristic level 117 has been set, after the container 102 has been filled with the crop 120, and after a fill mode 800 has been performed. FIGS. 2A-2B employ exemplary references to the selected crop characteristic 116 as moisture content, and the crop 120 as a grain, but is to be understood that the adaptive predictive controller model 200 applies to any selected crop characteristic 116, and any crop type 121 to be conditioned and/or stored in a container 102.

At step 232, the adaptive predictive controller model 200 samples the initial conditions of the crop 120, and provides these conditions to the virtual container model 210 which as noted above identifies drying parameters based on the initial conditions, and provides these to the local container model 220. Together, the virtual container model 210 and the local container model 220 calculate drying times in the processes shown in FIGS. 2A-2B during each drying step, at least by analyzing gain within such processes to arrive at desired mass transfer to achieve the selected crop characteristic 116.

The adaptive predictive controller model 200 accounts for the effect x of disturbances L which are external variables affecting the time needed to dry a crop 120 (or effect a mass transfer to reach the desired crop characteristic level 117), represented in FIGS. 2A-2B as $x_{L1}$ and $x_{Lm}$ and calculates gain resulting from such disturbances in blocks 202 and 204. Disturbances include local weather phenomena, container defects, fan performance disruptions, and any other factor which may impact drying times and therefore add to or lessen time needed to dry or re-condition the crop 120 within the container 102. Gain calculated in blocks 202 and 204 are provided to the local container model 220, and added to the feed-forward output represented as f(V) for the gain generated by the adaptive predictive controller model 200 $G_m$ as feedback time needed to assess the effect of feedback $x_{FB}$ as feedback control at block 234.

The local container model 220 calculates the gain that is needed for feed-forward control, based on both modeled or predicted, and real processes, and is based on machine learning elements such as artificial neural networks or block oriented models, either of which may be trained within a cloud-computing environment. The local container model 220 assesses gains from real bin inputs 236 such as data collected from sensors 130, and models this information together with the drying parameters to calculate a predicted feed-forward mass transfer M and gain from feed-forward control at block 237 to arrive a prediction $x_P$. The effects of feedback on mass transfer are combined to calculate gain from valves $G_{valves}$ 238. The adaptive predictive controller model 200 then adds the predicted gain $G_P$ to predict the time and valve configurations to achieve the predicted feed-forward mass transfer Mat block 240, which is combined with one or more models 246 that account for history and physical dimensions of the container 102, to assess the effects of the drying cycle 167 or recondition cycle 169 f(v) at block 242. The adaptive predictive controller 200 then determines whether the mass transfer to reach the desired crop characteristic 117 has been achieved, or not, at block 244; if it has not achieved at block 244, the adaptive predictive controller model 200 returns to a conditioning mode 252. If it has been achieved, the adaptive predictive controller model 200 then determines whether each section of the crop 120, in the whole container 102, is at the desired characteristic level 117 at block 245; if yes, then the adaptive predictive controller model 200 proceeds to a storage mode 248. If no, the adaptive predictive controller model 200 returns to the next drying step 250.

The local container model 220 serves as an adaptive predictive feedback and feedforward controller that performs multiple functions within the post-harvest crop management platform 100, in conjunction at least with the virtual container model 210 within the adaptive predictive controller model 200, and in some embodiments, with the one or more machine learning layers 170 and various elements thereof.

The adaptive predictive controller model 200 takes readings of initial conditions within the crop 120 and container 102, for example via the one or more sensors 120. These readings are used to configure the virtual container model 210. The virtual container model 210 identifies drying parameters that provide a basis for the flow rates for all of the different crop 120 drying configurations to be applied by the multi-stack assembly 106 in fluid flow patterns 162. These drying parameters are sent to the local container model 220 for further processing as discussed below.

The local container model 220 uses a mass model that, in one embodiment of the present invention, combines elements of mass balance modeling and mass transfer modeling, and in any case has dynamic blocks representing the different data inputs that are empirically based and derived from the characteristics of the crop 120 and the container 102.

Such a mass model uses a form of a universal accounting equation to determine the amount of a desired characteristic, in this example, water that has been added to or removed from the system. In this example, relative humidity of the air entering the system past the fan and through the plenum and exiting the system in the headspace are recorded and converted into absolute humidity, which is not a percentage but the mass of water in the air. By contrasting the mass of water in the air entering and leaving the system, the accumulative amount of water in the system is known. If more water is in the air when exiting the system than when entering it, it is known that water has been removed from the system. This same mass balance equation is applied to sensors embedded within the crop 120, treating each section or group of sections as its own system. The sampling of the absolute humidity from within the crop or grain mass may also be carried out with the stacks and valves configured to act as a sampling matrix, to pull the air from a desired location and move it past a sensor located elsewhere. In this way, one can determine the amount of moisture added to or removed from each section or group. This same principle can be applied to different desired characteristics. The absolute amount of moisture in the crop can be determined by the relative rate at which moisture is removed from the system, and as such, can either supplement or replace other methods such as the modified Chung-Pfost equation. For example, a crop that is higher in moisture content tends to dry at a faster rate than a crop that has already been dried. This can also be supplemented by data from a combine that would give the initial moisture content from the combine's on-board moisture content analyzer.

The local container model 220 therefore is, in one embodiment of the present invention, an application of a dynamic, block-oriented model 178 in such a mass model. The local container model 220 applies the drying parameters to this mass model, in combination with other data such as weather forecasts, to analyze one or more mass flows in a mass transfer to achieve the drying that is needed in a drying cycle 167 for various conditions over time. The local container model 220 reads these one or more mass flows, and predicts mass flows to achieve a desired condition of the selected crop characteristic 116 for the crop 120 at some specified future time as an output of such a dynamic, block-oriented model 178. These predicted mass flows serve as the basis for developing fluid flow patterns 162 to achieve the desired crop characteristic level 117 at some time in the future.

The drying cycle 167 is then set, and the multi-stack assembly 106 is actuated to apply the modeled fluid flow patterns 162 to the crop 120 to achieve the desired crop characteristic level 117. The system causes fans and the valve assemblies of the multi-stack assembly 106 to actuate to perform the drying cycle 167 and apply the fluid flow patterns 162, and sensors 120 identify and measure the conditions experienced during the process of performing the drying cycle 167. These conditions are then fed back into the local container model 220.

The gain coming from the local container model 220 is then adjusted to reach the desired state of the desired crop characteristic level 117, and the local container model 220 makes adjustments to the predicted condition based on data collected during performance of the drying cycle 167.

A mass model as described herein therefore serves as the foundation that the local container model 220 uses to determine characteristics of the crop 120, such as moisture content, dynamically during performance of the drying cycles 167 for both the current time and a future time. In addition, the predicted condition generated by the dynamic block-oriented model 178 may serve as one or more inputs for one or more nodes of a neural network 176, such that the local container model 220 is an application of multiple elements of the one or more machine learning layers 170.

The one or more neural networks 176 may use data from both actual processes performed, and the outputs of the dynamic blocks in the mass model, to automatically calculate and update drying parameters within one or more dynamic block equations. This allows for the post-harvest crop management platform 100 to automatically update the drying parameters in the dynamic block equations with non-dynamic machine learning elements such as the neural networks 176. In this manner, the predictions of the mass model may serve as inputs of the one or more neural networks 176, and may be applied at outputs thereof as well. This allows for dynamic and robust performance, driven by an empirical-based model that is enabled with the adaptability and auto tuning capabilities that machine learning can provide. This results in a predictive model that can be applied to a dynamic system without losing adaptability.

Returning to FIGS. 1A-1B, the one or more cycles may include one or more system commissioning cycles that include a pre-fill cycle 165, that is configured to prepare the container 102 to be filled with the crop 120, by executing one or more routines to perform specific actions either before a fill begins, while a fill is occurring, or following a fill. These include automatically executing a system check protocol to determine a fitness-for-use of all systems in the container 102 and multi-stack assembly 106. Another specific action is automatically opening and closing both vent and gate assemblies to rid the stack of accumulated material that would otherwise be difficult to remove from the system once filled. This may be performed either while a filling occurs, or during a fill, and may have the effect of leveling up each stack as the level of the crop 120 rises in the container 102 and along each stack. Once a substantial portion of the container 102 has been filled, another specific action of the pre-fill cycle 165 may automatically open a cleanout or series of cleanouts in the plenum chamber, to optimize air delivery through the plenum to the crop 120 and to the stacks. The need for this aspect of the pre-fill cycle 165 may be indicated by the pressure sensor 133, which as noted above may be configured to measure pressure in the influent area or plenum of the container 102, such that where pressure is rising beyond preset or normal levels, the cleanout(s) are automatically activated in the plenum or transition between the plenum and fan(s). Such preset or normal levels may be either provided as a user input 115, or automatically determined within the modeling framework, for example by the one or more machine learning layers 170.

Such a pre-fill cycle 165 may therefore perform a sequence of actions to test (pass/fail) the entire multi-stack assembly 106 to confirm it is functioning as designed prior to filling bin with the crop 120. For example, the pre-fill or system commissioning cycle 165 may initiate a system commissioning activity that turns each plenum fan on and off independently, and runs each for a preset sequence. The pre-fill cycle 165 may also open and close each valve and each gate, and hold each of them open for a preset sequence. The pre-fill or system commissioning cycle 165 may also test one or more of the sensors 130. For example, the pre-fill cycle 165 may record a reading for each temperature sensor 132 associated with each stack (or within the headspace or plenum) and confirm the reading within x degrees of the ambient temperature. The pre-fill cycle 165 may record a reading for each temperature. Additionally, the pre-fill cycle 165 may record a reading for each relative humidity sensor associated with each stack (or within the headspace or plenum), record the reading for one sensor on each stack, and confirm the reading within x degrees of ambient relative humidity. The pre-fill cycle 165 may also test pressure sensors by recording a reading for the influent or plenum pressure sensors before filling to confirm that they read at or near zero while later on reading an expected value. The pre-fill or system commissioning cycle 165 may further test pressure sensors by recording a reading for each pressure during each stack and valve configuration and confirming the reading within an expected range based on the fluid flow modeling layer 160 which may use the range finding sensor to determine the height of the crop and therefore the resistance to be seen. The post-harvest crop management platform 100 then generates a report 193 of each item tested, for example as a pass/fail indicator, as output data 190.

Still further, the pre-fill cycle 165 may also test $CO_2$ sensor readings in the plenum and in the headspace. Fan power may also be measured during the pre-fill or system commissioning cycle 165, and also air pressure, air flow, and electricity usage. Reports 193 may also be generated for information regarding these aspects of the pre-fill or system commissioning cycle 165.

The post-harvest crop management platform 100 may also apply a system commissioning cycle prior any other cycle that confirms the existence and location of equipment such as fans, burners, stacks, valves etc. The system commissioning cycle creates a matrix for each system commissioning test performed, showing vent and gate positions for entire sequence. The system commissioning cycle is an initial setup protocol for each container 102 based on container characteristics 104 such as for example size, diameter, height at eaves, bushels, and other parameters, as well as the particular design characteristics of the multi-stack assembly 106 that has been installed in the container 102, such as for example the number of stacks, and the number of valve assemblies per stack or sensors and ancillary equipment and their respective locations.

The pre-fill cycle 165 may also be used to determine if certain sensors 130, such as for example relative humidity, temperature or pressure sensors, need calibration. A calibration of the relative humidity and temperature sensors may be carried out simply by the system operating the fan to create a steady state against which the relative humidity and temperature may be calibrated. This may occur more than once to improve the calibration. Calibrating a pressure sensor, may, for example, occur by setting the reading to zero while the fan is in the off position and setting the reading to the 'high' reading during the calibration once filled. In such an action, the post-harvest crop management platform 100 may include defining an expected output of each sensor reading to 'pass' test, and generating a recommendation 192, report 193, or alert regarding sensor calibration or self-healing. Still further, that post-harvest crop management platform 100 may generate a visual or audible indicator that may be used to confirm operational sufficiency or indicate an operational deficiency, and/or display or otherwise alert that a data report has been generated for each action, such as for example where a power spike or pressure drop occurs when a particular gate opens.

The one or more cycles may also include a pre-dry or pre-condition cycle 166, in which modeled fluid flow pattern(s) 162 are applied to the crop 120 to reduce a resistance of one or more of the sections of the crop 120, including at least one of a core section(s) and a top section(s) of the crop 120.

The one or more cycles may also include a drying or conditioning cycle 166 that is configured to change the selected crop characteristic 116 to the desired crop characteristic level 117 for the multiple sections of the crop 120 by executing one or more routines to perform specific actions. In such a cycle, this desired crop characteristic level 117 may coincide with a level that is suitable for storage. Where moisture content is the selected crop characteristic 116, one or more drying cycles 166 are applied to dry the crop 120 evenly across the crop or grain mass, typically in the fastest manner possible to prepare the crop 120 for long-term storage in the container 102.

In one exemplary performance of the drying cycle 166, again where moisture content is the selected crop characteristic 116, the post-harvest crop management platform 100 examines inputs such as the crop type 121, a pre-set moisture content set point, an available drying power that enables fans to operate (a further example of a grainware parameter within the container characteristics 104), and a sampling cycle matrix, representing the map of moisture content, within the profile of the selected crop characteristic 116 generated by the sampling cycle discussed above.

To achieve the desired crop characteristic level 117, the post-harvest crop management platform 100 applies the fluid flow patterns 162 developed in the fluid flow modeling layer 160 and issues instructions for actuation of the multi-stack assembly 106 to direct fluid flow to the crop 120 in different sequences depending at least on the profile 158 of the selected crop characteristics 116 by opening and closing vents and gates 108 of each stack according to the sections of the crop 120 needing to be conditioned to reach the desired crop characteristic level 117, typically as rapidly as possible, so that the crop 120 reaches the moisture content set point, and returns to the beginning of the routine, with a revised profile 158 of the selected crop characteristic 116 representing the mapping performed by the sampling cycle and associated matrix 156, and repeats the routine for the desired sequence until the moisture content set point is again attained.

The post-harvest crop management platform 100 may create an available drying power matrix that represents the relative humidity, the ambient temperature, and the moisture content of the crop 120 in the container 102, as another element of output data 190. Such an available drying power matrix may be generated as a specific output of the modeling framework. This drying power matrix may be compared to the sampling matrix to determine which sections may be dried with the influent air, and in turn, only direct air toward those sections.

For example, the following values may populate a matrix that is a map of available drying power as follows for corn. For an ambient temperature of 40 degrees, and 26% moisture content, drying power is available for operation up to 98% relative humidity of the crop 120. At a 24% moisture content, drying power is available for operation up to 97.5% relative humidity of the crop 120. At 22% moisture content, drying power is available for operation up to 95% relative humidity of the crop 120. At 20% moisture content, drying power is available for operation up to 91% relative humidity of the crop 120. At 18% moisture content, drying power is available for operation up to 85% relative humidity of the crop 120. At 16% moisture content, drying power is available for operation up to 75% relative humidity of the crop 120. At 15% moisture content, drying power is available for operation up to 68% relative humidity of the crop 120. At 14% moisture content, drying power is available for operation up to 62% relative humidity of the crop 120. At 12% moisture content, drying power is available for operation up to 45% relative humidity of the crop 120.

The one or more cycles modeled by the fluid flow modeling layer 160 for delivery of fluid flow patterns 162 to the crop 120 may further include aeration cycle(s) 167 that maintains the crop 120 when it reaches the desired crop characteristic level 117, to equalize and sustain the desired crop characteristic level 117 across each section of the agricultural crop 102 within the container 102. One or more aeration cycles 167 are applied to keep the crop 120 in a particular state to maintain product quality, by applying a fluid as needed to maintain the desired level 117 of the selected characteristic 116 in each section of the crop 120.

Again using moisture content as an exemplary crop characteristic, once the crop mass reaches a user-specified moisture content set point, the post-harvest crop management platform 100 switches to the aeration cycle(s) 167 to maintain crop quality at the moisture content set point for a specified period of time.

An aeration cycle 167 initiates upon completion of a sampling cycle that determines that the moisture content has reached the moisture content set point provided as input data 110 by the user. The post-harvest crop management platform 100 measures various attributes of the crop 120 and creates an aeration cycle matrix, by turning on fan(s), setting an open/close position for all vents and gates 108 in each stack, for each section of the crop 120, and recording relative humidity and temperature sensor measurements for each section. The post-harvest crop management platform 100 then calculates and records the moisture content for each section, and also samples and records the ambient air temperature and relative humidity. The post-harvest crop management platform 100 then delivers fluid to the crop 120 in a fluid flow pattern 162 designed to ensure that moisture content (or any other characteristic being modeled), is maintained to a pre-set level. A moisture content report may also be generated and provided as output data 190 for each section within the container 102. This output may also serve as an input to initiate a further drying cycle 167, if moisture content has risen beyond a preset limit for maintaining quality of the crop 120 over the specified period of time.

It is to be noted that aeration cycles 168 maintain the quality of the crop, as opposed to removing the most amount of moisture in the shortest amount of time which is the general objective of pre-drying cycles 166 and drying cycles 167. Aeration cycles 168 typically utilize a different fluid flow pattern 162 that targets whole sections of the crop 120 at a time, instead of the individual sections as in a pre-drying cycle 166 or drying cycle 167, as the crop 120 typically does not need airflow that is as concentrated as during pre-drying or drying.

The one or more cycles may also include a reconditioning cycle 169 that is an application of the one or more expert control algorithms 164 to return the crop 120 from crop characteristics that are more typical or suitable for storage or transport to crop characteristics desired for market placement, before the crop 120 is removed from the container 102 to maximize the value of the crop 120. As in other cycles, the post-harvest crop management platform 100 measures various attributes of the crop 120 and creates a reconditioning cycle matrix, by turning on fan(s), setting an open/close position for all vents and gates 108 in each stack, for each section of the crop 120, and recording relative humidity and temperature sensor measurements for each section. The post-harvest crop management platform 100 then calculates and records the peak moisture content for each section, and also samples and records the ambient air temperature and relative humidity. The post-harvest crop management platform 100 then delivers fluid to the crop 120 in a fluid flow pattern 162 designed to ensure that moisture content (or any other characteristic being modeled), is returned to a pre-set level. A moisture content report may also be generated and provided as output data 190 for each section within the container 102.

Once the fluid flow modeling layer 160 has developed fluid flow patterns 162 that achieve the desired crop characteristic level 117, instructions are passed to the stack actuation element 180 to execute the plurality of expert control algorithms 164 to actuate 182 the multi-stack assembly 106 and release or accept fluid flow 186 to and from the various sections of the crop 120. It is to be understood that the cycles described herein may not all be performed by the post-harvest crop management platform 100, and that that not every cycle described herein may need to be performed by the post-harvest crop management platform 100 every time or in every instantiation thereof. Therefore individual cycles within the one or more cycles may be performed as determined within the modeling framework, and in any order.

It is to be understood, and as noted above, that the word "fluid(s)" and the words "fluid flow(s)" and "fluid flow pattern(s)" may include any material or composition delivered to or applied to a crop 120, and fluid(s) may exist in any state, such as liquids, suspended solids, and gases. Fluids may include, but are not to be limited to, ambient air, heated air, other gases, liquids, or any other substance applied to a crop 120. It is to be further understood that fluid(s) may be used interchangeably in this specification with the word "airflow(s)".

FIG. 3

Figure 3:
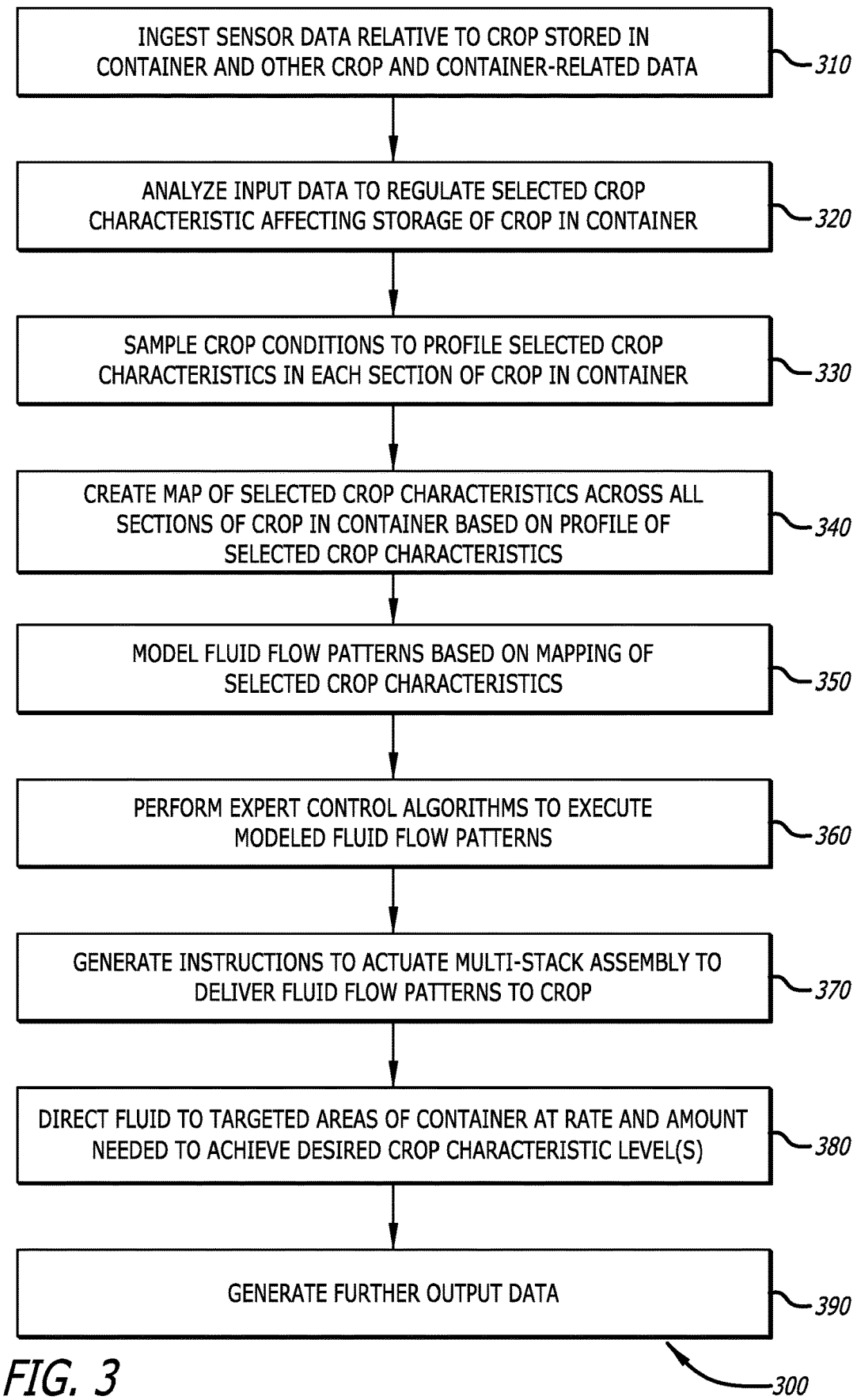
FIG. 3 is a flowchart of steps in a process of performing a crop storage management platform according to another embodiment of the present invention.
Figure 7B:
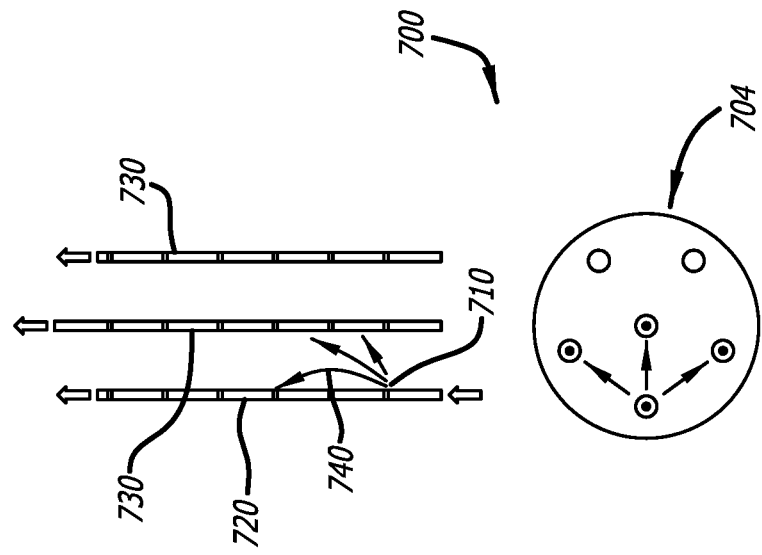
FIGS. 7A-7B are another exemplary illustration of fluid flow patterns delivered from a multi-stack assembly by executing one or more control algorithms in the post-harvest crop management platform of the present invention, according to another embodiment thereof.
Figure 7A:
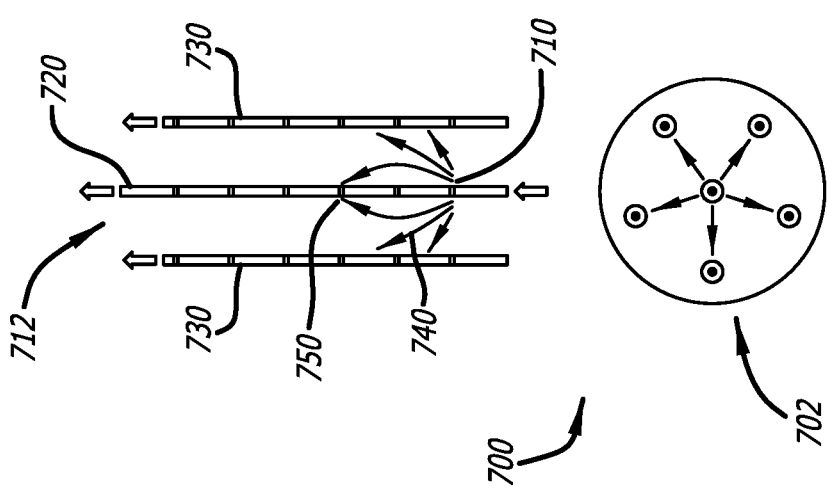

FIG. 3 is a flowchart of steps in a generalized process 300 for performing the post-harvest crop management platform 100, according to another embodiment of the present invention. The process 300 may be initiated by ingesting input data 110 such as sensor data 114 relative to a crop 120 stored in a container 102 at step 310, as well as other data, such as crop data 112 descriptive of the crop 120, and container-related data, such as container characteristics 104. At step 320, this input data 110 is analyzed in multiple algorithmic approaches configured to regulate a selected crop characteristic 116 affecting storage of the crop 120.

The process 300 samples crop conditions at step 330 in a sampling matrix 156 to generate a profile 158 of the selected crop characteristics 116, for each section of the crop 120. At step 340, the process 300 generates a map 152 of the selected crop characteristic 116, across all sections of the crop 120 within the container 102. At step 350, the process 300 then models fluid flow patterns 162 based on the profile 158 and the map 152 of the selected crop characteristic 116.

At step 360, the process 300 executes one or more expert control algorithms 164 to execute modeled fluid flow patterns 162. This occurs by generating instructions at step 370 to actuate elements of the multi-stack assembly 106 as described below, to deliver fluid to the various sections of the crop 120 within the container 102. At step 380, the process 300 directs fluid to targeted areas of the container 102, at a rate and amount needed to achieve desired crop characteristic levels 117, according to the one or more expert control algorithms 164. The process 300 also generates further output data 190 relative to conditions of the crop 120 within the container 102.

Multi-Stack Assemblies

The post-harvest crop management platform 100 is, as noted above, operative in one embodiment of the present invention in conjunction with one or more multi-stack assemblies 106, which are each comprised of at least one stack positioned within a crop 120 and within a container 102. In accordance with an embodiment that includes such a hardware configuration, each stack is configured with one or more of valve assemblies, having at least one vent and at least one gate 108, which each open and close to allow fluid, in the form of for example ambient air, heated or cooled air, gas, or any other solid, liquid, or gaseous substance suitable for applicability to a crop 120, to pass through the various sections of the crop 120.

Stacks may be placed in any manner inside a container 102, such as for example vertically, horizontally, or diagonally, and in any combination thereof, such as for further example in a lattice framework. Stacks may have different shapes, sizes, and configurations. In an exemplary embodiment, stacks may in the form of cylinders, each having an inlet, or bottom, port configured at or near a plenum, and an exhaust, or top port that may be configured with or near a headspace of the container, with the valve assemblies embedded within a mass of the crop 120 stored within the container 102. Regardless, it is to be understood that stacks of different sizes and configurations may be utilized within the same multi-stack assembly 106, depending for example, on the container characteristics 104 and/or crop type 121.

The plenum of a container 102 is an area or space, typically adjacent to a floor, that is separated from bin contents to facilitate air circulation from, for example, fans that cool or dry the contents of the container 102. A container 102 may include a divider that separates the contents from the plenum, serving as an aeration floor for the multi-stack assembly 106. The plenum may include one or more doors or hatches enabling inflows or outflows of air, liquid, or any other substance, for example to clean out the plenum of debris. It should be understood however that not all types of containers 102 include a plenum; instead, some containers 102 are configured, for example, with hopper-bottoms, through which stored crops are dispensed, and that the present invention is not to be limited to containers 102 having a plenum, nor having any one specific type of configuration discussed herein.

Each stack contains one or more valve assemblies, and each such valve assembly forms a valve that includes at least one vent and at least one gate 108 that together provide an opening in each valve, and plurality of openings in each stack, in spaced relation to each other, through which fluid may be released and accepted 186 by opening and closing 184 the vents and gates 108 during actuation 182. Vents and gates 108 may be of any size, shape, or structure, and may include any device capable of releasing and accepting 186 the flow of fluid from or to a stack.

Many configurations of valves, and vents and gates 108 with openings therein, are possible and contemplated within the present invention. In one exemplary embodiment, valves are placed in a vertical orientation; the top valve having some distance from the expected top of the crop or grain mass; the bottom valve having some distance from the bottom of the crop or grain mass; and the middle valve(s) placed evenly in between. It is to be understood that other configurations, and therefore other embodiments, are also possible, such as for example unevenly spaced valves, and top and bottom valves spaced in different relation to the top surface or aeration floor, respectively.

The multi-stack assembly 106 may also include one or more pneumatic actuators that actuate the mechanical components of the stack in response to instructions generated as output data 190 from the crop storage management and monitoring platform 100, such as to open and close 184 vents and gates 108. It is to be understood that the open and close positions do not need to be binary; that is to say, a vent or gate may be half-way open or any position in between. Each multi-stack assembly 106 therefore includes circuitry configured to receive and process signals communicated within the crop storage management and monitoring platform 100, through either a wired connection with the one or more processors 142, or wirelessly transmitted from one or more such processors 142, for actuating 182 the multi-stack assembly 106 particularly in response to the fluid flow modeling described herein.

Each multi-stack assembly 106 is either coupled to, or in communication with, one or more mechanical devices that generate fluid, such as fans, humidifiers, heaters, or other components that generate and condition the fluid delivered to a crop 120 to achieve the desired crop characteristic level 117. Such devices may also be coupled to, or in communication with, the circuitry described above to receive and process signals communicated within the crop storage management and monitoring platform 100, through either a wired connection with the one or more processors 142, or wirelessly transmitted from one or more such processors 142.

In operation, the plurality of valve assemblies, and vents and gates 108, are capable of delivering fluid flow to individual or multiple sections of the crop 120 in the container 102 in many different ways, to achieve the desired crop characteristic level(s) 117, and it is to be understood that many different fluid flow patterns 162 may be modeled and delivered to the crop 120 depending at least in part on modeled conditions within multiple sections of the crop 120, container characteristics 104, and other characteristics either identified by sensors 130 or provided as user inputs 115. Also, it is to be understood that different sections of the crop 120 may need different fluid flows at different types and at different speeds, temperatures, and durations. For example, in typical containers 102 for storage of a crop 120, the core section(s) generally receives less airflow from the plenum. This results in slower drying for the sections of the crop 120 that are located in the core section(s). The present invention addresses this issue by ensuring that core section(s) of the crop 120 receive more airflow when a stack is activated. In addition to enabling fluid flow from the system of vents and gates 108, the operation of the multi-stack assembly 106 also enables introduction of fresh air straight from the plenum, and exhausts the air from the lower half of the container from inside the crop 120 to prevent moisture from bottom or lower sections from re-wetting sections above, through any open vents on any stack (or, through the crop 120 itself). Other examples of fluid flow patterns, and applicable situations, are described further herein, particularly with respect to FIGS. 4-7.

It is to be understood that multi-stack assemblies 106, and more specifically the actuation of components thereof, may be operated via either a wired or wireless system, and that therefore vents and gates 108 may be operated and controlled by a wireless signal or signals from the post-harvest crop management platform 100. The present invention may therefore include wireless connectivity capabilities, and any type of wireless communications protocols may be utilized in the post-harvest crop management platform 100, such as cellular networks, Bluetooth connections, Wi-Fi (wireless local area networking) connection, DSRC (dedicated short-range communications), NFC (near-filed communications) or any other form of wireless transmission.

Fluid Flow Patterns

It is to be understood that there are many configurations of the multi-stack assembly 106 for delivery of fluid flow to the crop 120, and many different fluid flow patterns are possible, and within the scope of the present invention. It is to be further understood that different sections of a stored crop 120 have different densities and therefore different requirements to achieve the desired crop characteristic level 117. For example, a core section(s) of a stored crop often is more dense than either the perimeter or the top (or, in other words, inner sections are often more dense than outer sections or the top section(s) within a container 102).

Therefore, the post-harvest crop management platform 100 should consider the physical issues of having a large amount of a crop 120 to properly actuate the multi-stack assembly to achieve the desired crop characteristic level.

FIGS. 4A-4E illustrate an example of a fluid flow pattern 400 in a perimeter stack 410 having six valve assemblies 420, over five intervals 430 in one exemplary drying cycle 166. In this example, an expert control algorithm 164 ensures that the crop 120 dries in the desired manner to widen the spread of airflow in areas that would otherwise remain harder to penetrate. During the first interval of this fluid flow pattern 400, the bottom gates and vents of the stack 410 are kept closed, the while the rest of the vents and gates 108 are opened. During a second internal of the fluid flow pattern 400, the bottom vents are opened, and the next set of vents upward on the stack 410 are closed. This process continues moving up the stack 410, but not including the top vent.

FIGS. 5A-5F illustrate a fluid flow pattern 500 in this exemplary drying cycle 167 for a second target area, which is a center of the container 102. FIGS. 5A-5F illustrate a center stack 510 with six vents 530, over six intervals of the drying cycle 167 controlled by one or more expert control algorithms 164. The focus of the fluid flow pattern 500 on this area is to preemptively widen the spread of the plumes. This is accomplished by first targeting the top of the very center of the container 102 by flowing air out of the second highest vent 530 in a center stack 510 to the perimeter stacks 520.

FIGS. 6A-6L illustrate a fluid flow pattern 600 in this exemplary drying cycle 167 for a third target area, which is a center of the container 102, in a further application of the expert control algorithms 164 of the modeling framework. This application of the expert control algorithms 164 causes fluid flow 610 to push any remaining condensation and moisture out of the headspace first, then the container 102 section-by-section starting from the bottom in each stack 620, then again back out of the headspace. After this, one final push of the top section(s) occurs, and again one last push of the headspace. FIGS. 6A-6L illustrate twelve intervals in this expert control algorithm in twelve frames 630. The frames should be read left to right, top to bottom.

It should be understood that many different fluid flow patterns 162 are possible in a multi-stack assembly 106 having a plurality of vents assemblies comprised of both vents and gates 108 configured on each stack. Accordingly, the expert control algorithms 164 may be configured to deliver fluid flow patterns 162, and actuate the multi-stack assembly 106 accordingly, in many different ways. For example, one or more expert control algorithms 164 may actuate the multi-stack assembly 106 such that fluid is delivered from a stack around the container 102 one vent assembly at a time, for example based on a timer. In such a fluid flow pattern 162, all of the neighbors of the stack delivering fluid accept fluid from this vent. The vent of the same stack two sections up also accepts air from this vent.

FIG. 7A-7B illustrate a fluid flow pattern 700 according to an expert control algorithm 164 that controls fluid flow around the container 102 one vent 710 at a time, which may be based on a timer. All of the neighboring stacks 730 of the stack 720 releasing airflow 740 accept outflowing air from this vent 710. One or more vents 750 of the same stack 720, for example a vent 750 two sections up as shown in FIG. 7A, also accepts airflow 740 from this vent 710. FIGS. 7A and 7B depicts how this operates for both the center stacks (FIG. 7A) and perimeter stacks (FIG. 7B). FIGS. 7A-7B also illustrate overhead, or top, views 702 and 704 respectively of a multi-stack assembly 106 according to an embodiment in which multi-stack assembly 106 has five stacks, showing airflow emanating from central stacks (FIG. 7A) and from perimeter stacks (FIG. 7B).

Pressure Considerations

The post-harvest crop management platform 100 is also configured, in one aspect of the present invention, to influence airflow around vents within the crop 120 by, for example, pushing air out and allowing air in, and creating sections of high and low pressure. The natural pressure gradient of a container 102 storing a crop 120 is to have high pressure in the plenum or bottom, and near atmospheric pressure in the headspace or top. Airflow and pressure are inversely related, such that where airflow is concentrated or high, there is lower pressure, and where airflow is less concentrated or low, there is higher pressure. In the present invention, when valves of a multi-stack assembly 106 are opened, the drying front in the container 102 is being artificially controlled, and the pressure gradient of the container 102 is artificially bypassed.

When areas such as the headspace, where is little to no pressure other than atmospheric pressure, are connected with the middle of the container by opening and closing 184 vents and gates 108 to release and accept fluid flow 186, that zone of low pressure is extended into the middle area of the container 102, creating a high flow area; when areas such as the plenum are connected to the middle of the container 102, airflow and pressure are introduced into that middle area. Combining these actions and influencing pressure within different areas of a container 102 creates a number of effects, and knowledge of differences in pressure within the crop 120 may be used to detect a hotspot formation from, for example, crop deterioration, and to address the deterioration by adjusting actuation of a multi-stack assembly 106 in one of several different ways.

Changing the pressure in one area of the crop 120 from one state to another has the effect of controlling, spreading, or narrowing the plumes of fluid to produce flow to a desired section of the crop 120. Consider for example that when fluid is exhausted from the middle and sides of the container 102, and fluid is vented to the middle of the container 102, just above the exhaust vents on the sides, the now-existing low-pressure area on the sides and the now-high pressure area in the middle have the effect of spreading that plume out. The post-harvest crop management platform 100 is therefore capable of utilizing pressure differences to assist in spreading plumes of fluid out from vents and gates 108 to increase its drying, aeration, and re-conditioning capabilities, and reduce both energy consumption and time needed to reach a desired crop characteristic level 117.

This same arrangement has the additional effect of changing over the air in the container 102. Fresh air coming from the plenum loses its drying capacity as it moves through the crop or grain mass. This air that has traveled through the crop is exhausted by perimeter stacks and replaced by new fresh air from the plenum re-routed and directed out from the center valve(s) that (is/are) open, venting air to the crop. This pattern may be done with any of the stacks or combination of stacks, but when performed with two neighboring stacks the effect can be amplified. For example, if crop deterioration is detected forming on a North side of the container 102, the present invention may open, and vent to the crop 120, the one or two valves close to that area of deterioration on perimeter stacks, and exhaust from both the center and remaining side valves.

Additionally, opening a valve and venting air from the plenum to that area increases the fluid flow from the plenum through the aeration floor and overall into the container 102. A significant increase (for example, 10%-15% in airflow to the container 102 and that goes to the crop below the valve that is opened and venting air out into the crop may be realized by utilizing pressure differences. By way of further example, if the top or middle valve of a center stack is open and connecting the plenum to the top or middle of the crop 120, then the bottom section(s) in the center receives considerably more fluid flow.

If, by way of further example, deterioration is detected to the South of the center stack, but it is too far to reach with the plume from either the center stack(s) or the outside stacks, one can vent from the center valves in the middle, and exhaust from the perimeter stack to the south.

Such a center stack venting increases the airflow from the plenum through the aeration floor. The center stack venting also "pushes" the airflow coming up from the plenum toward the outside. If necessary, exhausting from the South perimeter stack (further) "pulls" this same airflow (further) toward itself but not into it, such that the end result is that as extra airflow comes from the center of the container 102, the center venting pushes and the South exhausting pulls it, leaving it in the desired location between the stacks. In this manner, the present invention is able to direct more airflow at the area that is unreachable by any stack directly.

Pressure, like any other crop characteristic, may be mapped within the post-harvest crop management platform 100, and like other maps and/or matrices generated by the crop characteristic modeling layer 150, may be provided as input to the fluid flow modeling element 160. Any type of pressure sensed by sensors 120, and/or derived from sensor data 114, may be mapped within the crop characteristic modeling layer 150, such as for example feed pressure, exhaust pressure, fluid flow pressure, or pressure on one or more stacks of the multi-stack assembly 106. Regardless of the type of pressure mapped, such a map may present hotspot information, since as noted above, knowledge of differences in pressure may be used to detect crop deterioration and map a measurement of resistance within the crop 120. If for example the pressure when a particular stack is venting is higher than the other stacks doing the same, it may be indicative of either crop deterioration or excess fines and may be further indicative of poorer condition of the crop 120 in areas above the valve. Conversely, if the pressure when the same stack is exhausting is higher than the other stacks doing the same, it may be indicative of either crop deterioration or excess fines and may be further indicative of poorer condition of the crop 120 in areas below the valve. Utilizing the stacks as a virtual sensor matrix of pressure sensors combines these examples to form a three-dimensional pressure map which may be used to indicate crop deterioration, fines or sections of the crop that are of poorer condition.

Knowledge of pressure differences also aids in lowering a resistance of the top and center sections of a crop 120 which makes fluid flow more uniform, and therefore the end result is more uniform. It also helps to push more fluid through the crop 120, and speed up drying, in effect creating positive and negative feedback conditions. For example, if moisture is successfully and quickly removed, the resistance is lower leading to higher airflow, resulting in a positive feedback response to pressure differentiation and further lowering the resistance. Conversely, if removal of moisture is unsuccessful, a more solid crop or grain mass (i.e., a hotspot or crop deterioration) will form, making it harder to push air through, producing a negative feedback response. Being able to actively map and provide sufficient airflow to these sections of higher resistance increases the probability of a positive feedback response which in turn increases overall airflow to the container and decreases overall time required to condition the crop. Additionally, measuring resistance from pressure readings also enables an assessment of pressure on the stacks resulting from filling and emptying a container 102, as well as movement of a crop 120 within a container 102, which helps the post-harvest crop management platform 100 assess any damage to the container 102 or to the stacks (or components parts thereof) of the multi-stack assembly 106.

Output Data

The post-harvest crop management platform 100 generates output data 190 resulting from its function to regulate selected crop characteristics 116 of a crop 120 within a container 102, and in response to the various analyses and actions performed within the modeling framework. This output data 190 may generally take any form, and provide any type of information. For example, output data 190 may comprise one or more instructions 191 that include signals for follow-on activities, or comprising specific information. Such specific information may include container conditions or in-container crop conditions information 192, either in a raw or processed form, such as specific values for the selected crop characteristic 116, for any section of the crop 120, and for any period of time that the crop 120 was stored in a container 102. The present invention may further be configured to generate follow-on information that results from the data processing performed within the post-harvest crop management platform 100 in one or more functions, such as for example a recommendations and alerting function 192, reporting function 193, and a mapping function 194. One example of information generated in the recommendation and alerting function 193 is a malfunction in one or more sensors 130, in one or more of the vents or gates 108 comprising a multi-stack assembly 106, or in fans used to provide fluid flow to the multi-stack assembly 106.

Specific types of output data 190 are also contemplated, and within the scope of the present invention. For example, output data 190 may include loading and unloading information 196, such as for example scheduling of such activities, where the post-harvest crop management platform 100 integrates with unloading equipment to extract the crop 120 from a container 102. Output data 190 may be generated related to procurement 197 of materials, such as propane needed for powering equipment, for example according to modeled or planned usage of supplemental heat and fans. Output data 190 may also include sensor calibration 198 or sensor maintenance, for example where errors are detected in sensor readings, or sensors return information suggestive of sensor malfunction. An output for sensor calibration 198 may include an instruction to re-calibrate any given sensor 130, based on for example self-testing of the sensor 130, and/or comparison against other sensors 130.

Additionally, output data 190 may be provided to a crop management system 199 for other utility, for example as part of broader actions within autonomous field and farm operations and activities as noted herein. Still further, output data 190 may include information for other systems connected to the post-harvest crop management platform 100, such as for example information provided for external insurance and finance actions.

Output data 190 may further include traceability information, for example as part of the reporting function 193. Such traceability information may include the drying history of a crop 120, on a section-by-section basis throughout the entire temporal spectrum in which the crop 120 is being conditioned, for example so that the drying history may be associated with each section or layer of crop 120 upon emptying of the container 102 up until a transfer of custody. Such traceability information may be combined with other attributes such as sensor data 114 used within the modeling framework to perform drying, aeration, and recondition functions. Traceability information, and all types of output data 190, may be provided as noted herein via one or more APIs, and may be generated so as to be compatible with other follow-on systems.

Output data 190 may also be provided to a decision support tool 148 configured, as noted below, to view and engage with information in the post-harvest crop management platform 100. Still other specific types of output data 190 are shown, for example, in FIGS. 8A-8D.

Decision Support Tool

A decision support tool 148 may be incorporated within, and may operate in conjunction with, the post-harvest crop management platform 100 of the present invention. Such a decision support tool 148 may be configured to enable customized user operation and selection of various attributes for performing the post-harvest crop management platform 100, such as for example input and/or selection of specific agricultural crop data 112, and user inputs 115, including the selected crop characteristic 116 and the desired crop characteristic level 117, and any other parameters or variables, such as specifying a drying strategy and expected outcomes, (for example, conserving energy to expediting drying to increasing maximum storage time). The decision support tool 148 may also be used to monitor performance of, and calibrate, the various elements of a multi-stack assembly 106. Still further, the decision support tool 148 may also be used to monitor sensor 130 performance, calibrate and re-calibrate sensors 130, as well as cross-check with known sensor data 112 values from the same container 102 and similar readings from similar containers, and perform any diagnostic functions on either the sensors 130 or the multi-stack assembly 106. The decision support tool 148 can include a user interface, and pull-down menus on such an interface (or in web-based or application-based modules to customize the input data 110, as well as to modify performance of the modeling framework, such as for example by interactively tuning the expert control algorithms 164 or, where utilized, the various values serving as inputs, weights, and biases, or "knobs", of neural networks 176 as discussed further below. In addition to desktop, laptop, and mainframe computing systems, users may access the decision support tool 148 using applications resident on mobile telephony, tablet, or wearable computing devices.

Machine Learning Layer(s)

In the present invention, the post-harvest crop management platform 100 performs sampling cycles to sample conditions of the crop 120 and model the selected crop characteristic 116 to determine when at least drying cycles 167, aeration cycles 168, and reconditioning cycles 169 are to operate. Accordingly, and as noted above, the various elements of the modeling framework—the crop characteristic modeling layer 150, the fluid flow modeling layer 160, and the stack actuation element 180—all operate together to regulate the selected crop characteristic 116 and achieve the desired crop characteristic level 117. The post-harvest crop management platform 100 may also apply the one or more layers of machine learning 170 to at least the first two of these elements to improve upon, for example, an understanding of input data 110 and data generated in sampling cycles to assist the adaptive predictive controller model 200 at least as to the predictions generated as to mass transfer, and the time and valve configurations needed to achieve those predictions.

The one or more machine learning modeling layer(s) 170 may comprise many different types of machine learning, and apply many different mathematical approaches to analyzing information and generating outputs that improve outcomes of the modeling framework described herein. For example, in one embodiment of the present invention, one or more machine learning modeling layer(s) 170 may be comprised of algorithms that apply techniques of supervised learning, reinforced learning, and other approaches of machine learning further evaluate input data 110 to develop and apply the adaptive predictive controller model 200 in the fluid flow modeling layer 160, and increase its accuracy and improve its efficiency, by analyzing the outcomes of prior, known execution of expert control algorithms 164 and the resulting delivery of fluid flow patterns 162.

The one or more machine learning modeling layer(s) 170 applied in the post-harvest crop management platform 100 may be comprised of any of several different mathematical approaches, as noted above. For example, the post-harvest crop management platform 100 may apply one or more statistical analyses 172, regression analyses 174, neural networks 176, and block oriented models 178, and any of the many types of each.

Statistical analyses are non-deterministic mathematical approaches that enable calculation of probabilities that events will or will not occur. In a statistical model specified via mathematical equations, some of the variables do not have specific values, but instead have probability distributions, so that some of the variables are stochastic or random; in other words, such models examine approaches that involve variables whose values depend on outcomes of random phenomena. Statistical analyses 172 may be applied in the present invention to examine probabilities of different future outcomes, such as the probability that the crop 120 will reach a desired crop characteristic level 117 at a specified future time, given certain variables, some of which have random or uncertain values, for example changing ambient weather conditions over the course of a drying period. Regardless of the variable having such random or uncertain properties, such statistical analyses 172 may be applied either alone, or in conjunction with, other machine learning approaches. Statistical analyses may also be applied, and the one or more machine learning layers 170 may further be configured to, identify outlier data points among sensor data 112 that suggest, as an output 198, checking for and calibrating sensors 120.

Regression analyses 174 are types of statistical analyses where models are used for estimating the relationships between variables of interest, such as for example a dependent variable and one or more independent variables (often called 'predictors'). This type of machine learning is used to infer causal relationships between the independent and dependent variables, and for prediction and forecasting of outcomes where such causal relationships are impactful on future states for application of the overall modeling being performed. There are many types of regression analyses 174, such as linear and non-linear regression, and specific approaches such as logistic regression, that enable the use of derived parameters, such as drying parameters identified by the virtual bin model 210, to interpret the importance of maximum values in form of the log-odds when calculating probability values. For example, other types of logistic functions, and other types of regression analyses, may also be utilized to calculate probabilities in the present invention, and are within the scope of the present invention. Other approaches that may be utilized include, but are not limited to, decision trees, random forest classifiers, support vector machines, and probit. It is therefore to be further understood that the present invention, and the present specification, are not to be limited to any one type of mathematical model or statistical process mentioned herein, particularly as to its application in the one or more machine learning layers 170.

Neural Networks in Machine Learning Layer

Such machine learning layers 170 may also include applications of neural networks 176. Neural networks generally are comprised of nodes, which are computational units having one or more biased input/output connections. Such biased connections act as transfer (or activation) functions that combine inputs and outputs in some way. Nodes are organized into multiple layers that form the neural network. There are many types of neural networks, which are computing systems that "learn" to perform tasks, such as modeling time and valve configuration schemes and fluid flow patterns, and selecting appropriate configuration schemes and patterns, without being programmed with task-specific rules, based on examples.

Neural networks generally are based on arrays of connected, aggregated nodes (or, "neurons") that transmit signals to each other in the multiple layers over the biased input/output connections. Connections, as noted above, are activation or transfer functions which "fire" these nodes and combine inputs according to mathematical equations or formulas. Different types of neural networks generally have different configurations of these layers of connected, aggregated nodes, but they can generally be described as an input layer, a middle or 'hidden' layer, and an output layer. These layers may perform different transformations on their various inputs, using different mathematical calculations or functions. Signals travel between these layers, from the input layer to the output layer via the middle layer, and may traverse layers, and nodes, multiple times.

Signals are transmitted between nodes over connections, and the output of each node is calculated in a non-linear function that sums all of the inputs to that node. Weight matrices and biases are typically applied to each node, and each connection, and these weights and biases are adjusted as the neural network processes inputs and transmits them across the nodes and connections. These weights represent increases or decreases in the strength of a signal at a particular connection. Additionally, nodes may have a threshold, such that a signal is sent only if the aggregated output at that node crosses that threshold. Weights generally represent how long an activation function takes, while biases represent when, in time, such a function starts; together, they help gradients minimize over time. At least in the case of weights, they can be initialized and change (i.e., decay) over time, as a system learns what weights should be, and how they should be adjusted. In other words, neural networks evolve as they learn, and the mathematical formulas and functions that comprise neural networks design can change over time as a system improves itself.

Neural networks 174 instantiated as part of the modeling performed within, or in conjunction with, the one or more machine learning layers 170 may be applicable in one or more of the crop characteristics modeling layer 150, the fluid flow modeling layer 160, and the stack actuation element 180, particularly where modeling of characteristics of the crop 120 within the container 102 involves determining and assigning weights for evaluating drying parameters within the adaptive predictive controller model 200. For example, a neural network 174 trained on historical records representing prior atmospheric conditions, prior usage of the bin in previous years, and physical dimensions of the container 102 may improve the resulting processing required to correctly configure a scheme comprised of time and valve configurations, and calculate a most appropriate fluid flow pattern(s) 162 (or set of such fluid flow patterns 162) to facilitate execution of the expert control algorithms 164 for performing the various cycles to achieve the desired crop characteristic 117. This may be particularly important where configuration schemes and fluid flow patterns 162 must be calculated in time-sensitive, or quickly changing, situations that require a fast and accurate response, for example where ambient weather conditions change rapidly.

The application of neural networks 176 within the one or more machine learning layers 170 may include instantiations of different networks for different purposes. The present invention contemplates both "production" neural network(s), configured to refine the algorithms performed within the overall modeling framework to generate output data 190, and "training" neural network(s), configured to train the production network(s) using improvements on the reasons for prior, historical outcomes of predictions or forecasts that have been learned within the machine learning modeling layer 170.

Neural networks 176 can also incorporate a time delay, or feedback loop, which is calculated to generally account for temporal dependencies at least in identifying and applying drying parameters when performing the bin model 210 and modeling fluid flow patterns 162, to further improve the results of the modeling framework. For example, such a time delay or feedback loop may represent one or more of a lag time between the air traveling past a fan and into and through the plenum, traveling through a stack, coming out of a valve, traversing the crop, returning to a stack through another valve, and finally going past a sensor. Still further, such a time delay or feedback loop may represent the time that it takes for a 'good' signal from the crop—for example reaching equilibrium with a certain section—and then using this data and not the data before it. Regardless, and as noted in more detail below, this may be performed by a particular type of neural network that accounts for timed data sequences, such as for example a Long-Short-Term-Memory (LS™) neural network, discussed further herein. Feedback loops and other time delay mechanisms applied by the various mathematical functions of such a neural network are modeled after one or more temporally-relevant characteristics, for example those derived from the profile of selected crop characteristics 116, the crop characteristic modeling layer 150, or the fluid flow modeling layer 160, and incorporate calculated weights and biases as discussed above. The post-harvest crop management platform 100 applies these elements of neural network design to outputs of production neural networks and generate the output data 190 as part of regulating the selected crop characteristic 116.

Neural networks may be configured to address the problem of decay in longer time-dependent sequences in an architecture that has multiple, interactive components acting as "blocks" in place of the conventional layers of the neural network. Each of these blocks may represent a single layer in that middle layer, or may form multiple layers; regardless, each block may be thought of as representing different timesteps in a time-dependent sequence analysis of input data.

The components of such a specially-focused neural network form its internal state and include a cell, which acts as the memory portion of the block, and three regulating gates that control the flow of information inside each block: an input gate, an output gate, and a forget gate. The cell remembers values over arbitrary time intervals, by keeping track of the dependencies between elements in an input sequence, and the three gates regulate the flow of information into and out of the cell. The input gate controls the extent to which a new value flows into the cell, the forget gate controls the extent to which a value remains in the cell, and the output gate controls the extent to which the value in the cell is used to compute the output of the block. The decision-making function of these gates is often referred to as the logistic sigmoid function for computing outputs of gates in these types of neural networks. There are connections into and out of these gates, and at least the weights of these connections, which need to be learned during training, determine how the gates operate.

Inside neural network blocks, there are additional layers that perform the activation functions needed to ensure that time-dependent data sequences are properly analyzed to avoid decay. One such activation function that may be incorporated is a tanh layer, which effectively classifies input data by determining which input values are added to the internal state of the block. Input gates are a layer of sigmoid-activated nodes whose output is multiplied by inputs classified by preceding tanh layers. The effect of these activation functions is to filter any elements of the inputs that are not required, based on the values assigned to each node for the problem being analyzed, and the weights and biases applied. The weights applied to connections between these nodes can be trained to output values close to zero to switch off certain input values (or, conversely, to pass through other values). Another internal state of a block, the forget gate, is effectively a feedback loop that operates to create a layer of recurrence that further reduces the risk of decay in time-dependent input data. The forget gate helps the neural network learn which state variables should be "remembered" or "forgotten".

Supervised learning is an application of mathematical functions in algorithms that classify input data 110 to find specific relationships or structure therein that allow the post-harvest crop management platform 100 to efficiently produce highly accurate output data 190. There are many types of such algorithms for performing mathematical functions in supervised learning approaches. These include regression analysis (including the logistic regression discussed above, and polynomial regression, and many others), decision trees, Bayesian approaches such as naive Bayes, support vector machines, random forests, anomaly detection, etc.

Neural networks are also a type of such supervised learning approaches, which may also include one or more of the computational techniques in the algorithms described above within their structures. Neural networks are more flexible than regression approaches, and allow for combinations of both structured data (e.g., sensor data 114) and unstructured data (e.g., observations provided by users 115) as inputs to produce the types of outputs desired in the post-harvest crop management platform 100.

Recurrent neural networks are a name given to types of neural networks in which connections between nodes follow a directed temporal sequence, allowing the neural network to model temporal dynamic behavior and process sequences of inputs of variable length. These types of neural networks are deployed where there is a need for recognizing, and/or acting on, such sequences. As with neural networks generally, there are many types of recurrent neural networks.

Neural networks having a recurrent architecture may also have stored, or controlled, internal states which permit storage under direct control of the neural network, making them more suitable for inputs having a temporal nature. This storage may be in the form of connections or gates which act as time delays or feedback loops that permit a node or connection to retain data that is prior in time for modeling such temporal dynamic behavior. Such controlled internal states are referred to as gated states or gated memory, and are part of long short-term memory networks (LSTMs) and gated recurrent units (GRUs), which are names of different types of recurrent neural network architectures. This type of neural network design is utilized where desired outputs of a system, such as the post-harvest crop management platform 100, are motivated by the need for memory, as storage, and as noted above, where the system is designed for processing inputs that are comprised of timed data sequences. Examples of such timed data sequences include video, speech recognition, and handwriting—where processing requires an analysis of data that changes temporally. In the present invention, where output data 190 is in the form of forecasted states of a crop 120, an understanding of the influence of various events and sentiment on a state over a period of time lead to more highly accurate and reliable predictions or forecasts.

Many other types of recurrent neural networks exist. These include, for example, fully recurrent neural networks, Hopfield networks, bi-directional associative memory networks, echo state networks, neural Turing machines, and many others, all of which exhibit the ability to model temporal dynamic behavior. Any instantiation of such neural networks in the present invention may include one or more of these types, and it is to be understood that neural networks 176 applied within the modeling framework and the one or more machine learning layers 170 may include different ones of such types. Therefore, the present invention contemplates that many types of neural networks may be implemented, depending on the specific crop 120 being analyzed, container characteristics 104, the nature of the selected crop characteristic 116 and/or the desired crop characteristic level 117, and/or on the impact of other variables within the input data 110.

Block-Oriented Models

The one or more machine learning layers 170 may also include applications of block-oriented models 178, which are typically based on linear dynamic and non-linear static blocks that are connected in various sequential/parallel ways. Block-oriented models represent dynamics of a problem by a linear transfer function, and capture the nonlinearities using nonlinear functions of inputs and outputs of a linear system.

Block-oriented models are a class of mathematical models that are useful in describing the dynamic behavior of certain classes of systems. These include both linear models that serve as an effective basis for the characterization of important qualitative behavior like stability, for the design of feedback control systems, for the development of empirical models, among other applications, and non-linear models that are based on interconnections of linear dynamic models with static nonlinearities. Feedforward block-oriented models are a subset of this class of non-linear, block-oriented mathematical models that represent nonlinear models, and are comprised of series, parallel, or combined series/parallel interconnections of linear dynamic models and static (i.e., memoryless) nonlinearities. Particular configurations of the involved blocks result in the well-known Hammerstein, Wiener, Hammerstein-Wiener and generalized Hammerstein models.

Block-oriented models 178 may be applied by the post-harvest crop management platform 100 in the adaptive predictive controller model 200 to examine a feed-forward gain and apply those results to predict mass transfer from a feed-forward control in a linear transfer function f(V), by accounting for nonlinearities of at least the various inputs using nonlinear functions. Regardless of the style and form of its applicability however, it is to be understood that block-oriented models 178 may be applied either alone, or in conjunction with, other machine learning approaches discussed herein within the one or more machine learning layers 170.

FIGS. 8-11

Figure 8A:
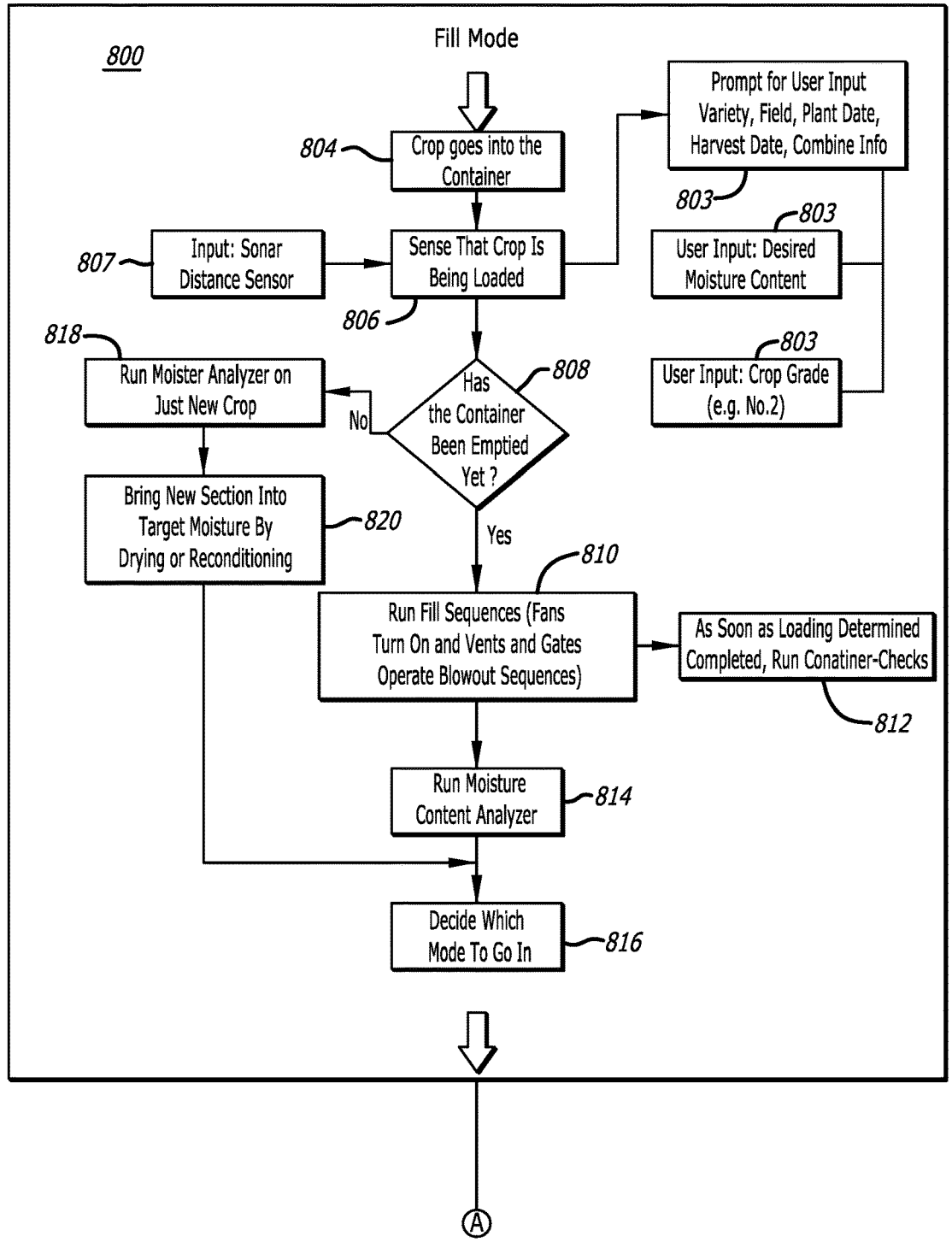
FIGS. 8A-8D are block diagrams and flow charts illustrating elements of container modes within which exemplary fluid flow patterns are delivered from a multi-stack assembly by executing one or more control algorithms in the post-harvest crop management platform of the present invention, according to further embodiments thereof.
Figure 8B:
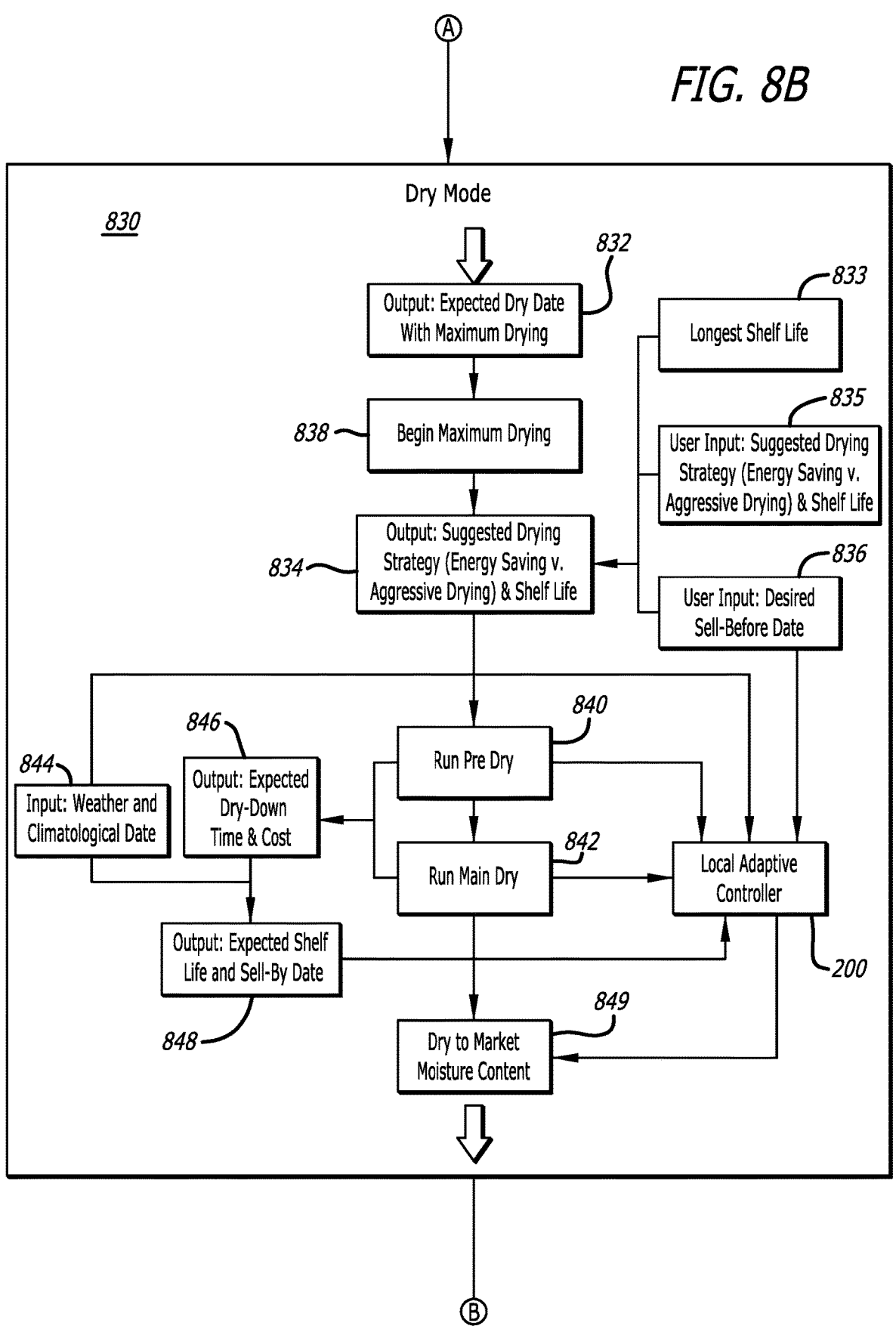

FIGS. 8A-8B are block diagrams and flow charts that illustrate elements of bin modes within which fluid flow patterns 162 are delivered from the multi-stack assembly 106 by executing the one or more control algorithms 164 in the post-harvest crop management platform 100 of the present invention, according to further embodiments thereof.

FIG. 8A illustrates an exemplary fill mode 800 that may represent all or part of a pre-fill cycle 165, with user inputs 115 at blocks 802 that include crop type 121, and desired crop characteristic levels 117 representing an initial moisture content, a storage moisture content, a market moisture content, a crop sell-by date, and a drying strategy (for example, speed vs. cost vs. shelf-life). The fill mode 800 is initiated when the crop 120 goes into a container 102 at block 804, either automatically as the crop 120 begins to be added to the container 102 at block 806 (for example, from a signal(s) communicated from loading equipment, or from a signal(s) communicated by one or more sensors that detect a loading operation such as a range finder either proximate to the container to detect in-position loading equipment or the changing level of the crop 120 in the container), or manually by a user, for example via the decision support tool 148. For example, a sonar/ranging sensor 136 may be utilized to provide an input that the bin is being filled with a crop 120 as in block 807. User prompts 803 may also be provided for further user inputs 115, such as for further entry of desired crop characteristic levels 117 or other user inputs or overrides. Regardless, the fill mode 800 continues by checking 808 whether the container has been partially or fully emptied. If it has only been partially emptied upon another filling cycle, the present invention first treats the newly-filled crop separately, then returns to the previous operation after a set amount has been reached. If it has been fully emptied, it performs a fill sequence 810 that includes operating fans and vents in a blowout sequence. The fill mode 800 then performs bin checks 812, and runs a moisture content analyzer 814 and decides 816 which other mode to enter. If the container 102 has not yet been emptied following a fill operation beginning at block 804, the post-harvest crop management platform 100 runs a moisture analyzer on newly-added material at block 818, and brings the newly-added material to the desired crop characteristic level 117 at block 820 in one or more other modes.

FIG. 8B illustrates an exemplary dry mode 830, where the post-harvest crop management platform 100 is configured with an expected drying date with maximum drying as shown at block 832, directed by an output condition 834 that is provided with either user inputs for maximum storage time/longest shelf life 833, user prompts 835 for inputs such as a desired sell-by date, or inputs 836 such as a suggested drying strategy (for example, energy saving versus aggressive drying speed versus maximum storage time or longevity or shelf life). The dry mode 830 begins drying at block 838, and begins a pre-drying cycle 166 at block 840. The dry mode 830 dries the crop 120 based on the drying strategy 842, and dries to the desired market moisture content 849 (provided as a desired crop characteristic level 117). Other inputs as shown in block 844 may also be provided, such as weather information. Still further, the post-harvest crop management platform 100 may generate specific output data 190 such as for example an expected dry-down time at block 846, or an expected shelf life and sell-by date at block 848.

Figure 8C:
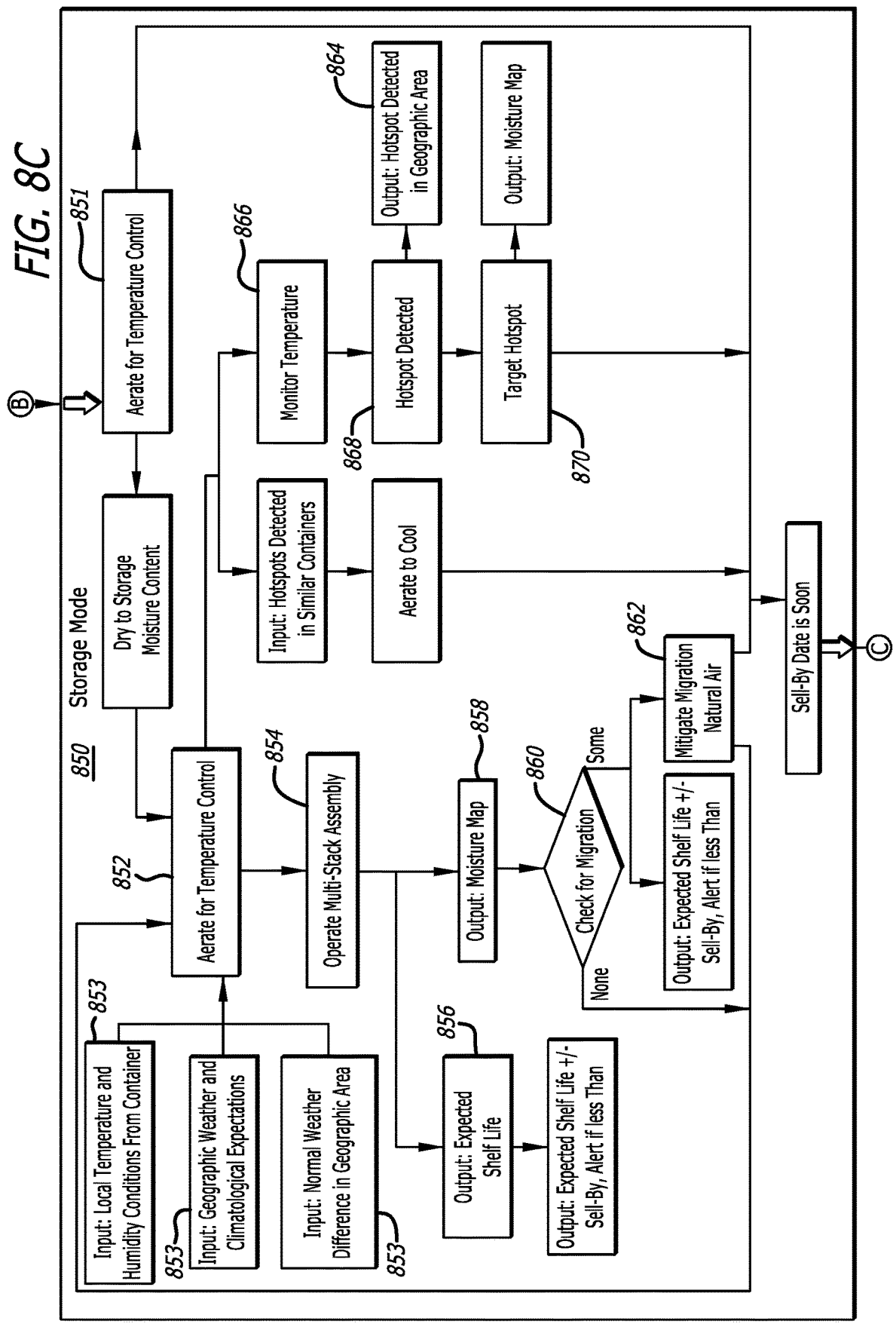

FIG. 8C illustrates an exemplary storage mode 850, which may be initiated where the dry mode 830 provides information regarding completion of a drying cycle 166 and initiation of an aeration cycle 167 to cool a crop 120 at block 851 by aerating for temperature control, and maintain a moisture content level for storage. The storage mode 850 also matches 852 the aeration for temperature control of the crop 120 to ambient temperatures outside the container 102 in periods of time during which it is advantageous to do so such as when the outside average temperature rises to above freezing. Specific inputs 853 to the storage mode 850 may include local temperature information, humidity conditions from within the container 102, expected climate and meteorological information for the particular geographic area where the container 102 is located, and a normal weather differences or ranges for the geographic area where the container is located within a certain radius, latitude or climate. The storage mode 850 operates the multi-stack assembly 106 for example as at block 854, and may generate specific output data 190 such as expected shelf life 856, a moisture content map 858, and may further perform a check for moisture migration 860 to either mitigate the moisture migration at 862, or generate an output 864 with an alert of a detected hotspot in a geographic area. The storage mode 800 may also monitor bin temperature at block 866, and where crop deterioration is detected at block 868, target the crop deterioration at block 870 for extra aeration. Where other user inputs 115 indicate crop deterioration detected in similar bins, switch to a different aeration schedule for the aeration cycle 168 as in block 870.

Figure 8D:
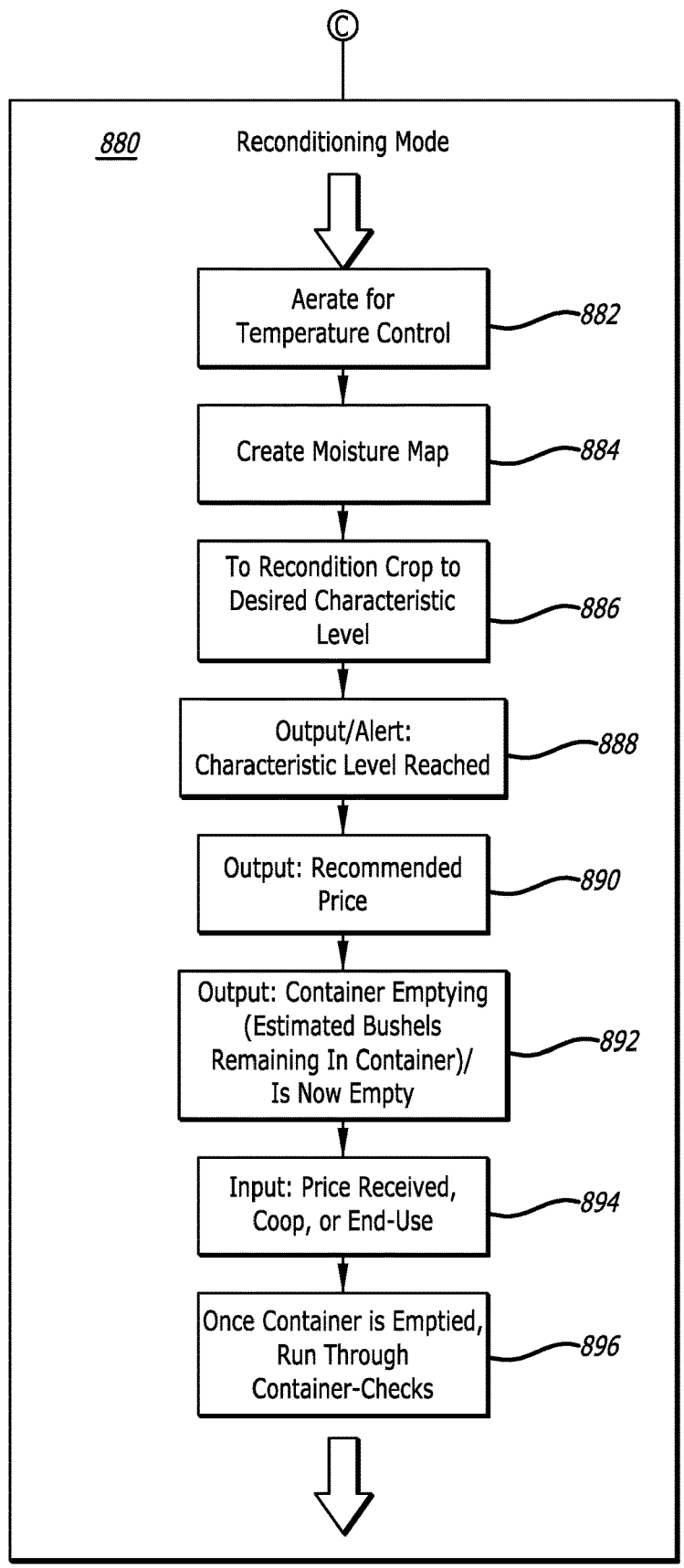

The post-harvest crop management platform 100 may also include a re-conditioning mode 880 as illustrated in FIG. 8D, for performing a reconditioning cycle 169. This re-conditioning mode 880 aerates the crop 120 for temperature control at block 882, creates a moisture content map at block 884, and re-conditions the crop 120 to a desired moisture content at block 886. Outputs that may be generated include an alert that a desired moisture content has been reached at block 888, a recommended price at block 890, and alert that the container 102 is now empty at block 892. The re-conditioning mode 880 may also receive an input at block 894 indicating an end of the storage mode 880 and reconditioning cycle 169, such as for example that a price has been received from a co-op or end user, and once the container 102 is emptied or partially emptied, the storage mode 880 may perform post-emptying bin checks 896. It is to be noted that post-emptying bin checks 896 need not be performed when a container 102 is completely empty, and therefore may be performed where a container 102 has been partially emptied. Regardless, the one or more cycles may also include an emptying cycle 161 that is an application of the one or more expert control algorithms 164 to deliver one or more fluid flow patterns 162 to a partially-empty container 102, or perform other system-level routines on an empty container 102.

Figure 9:
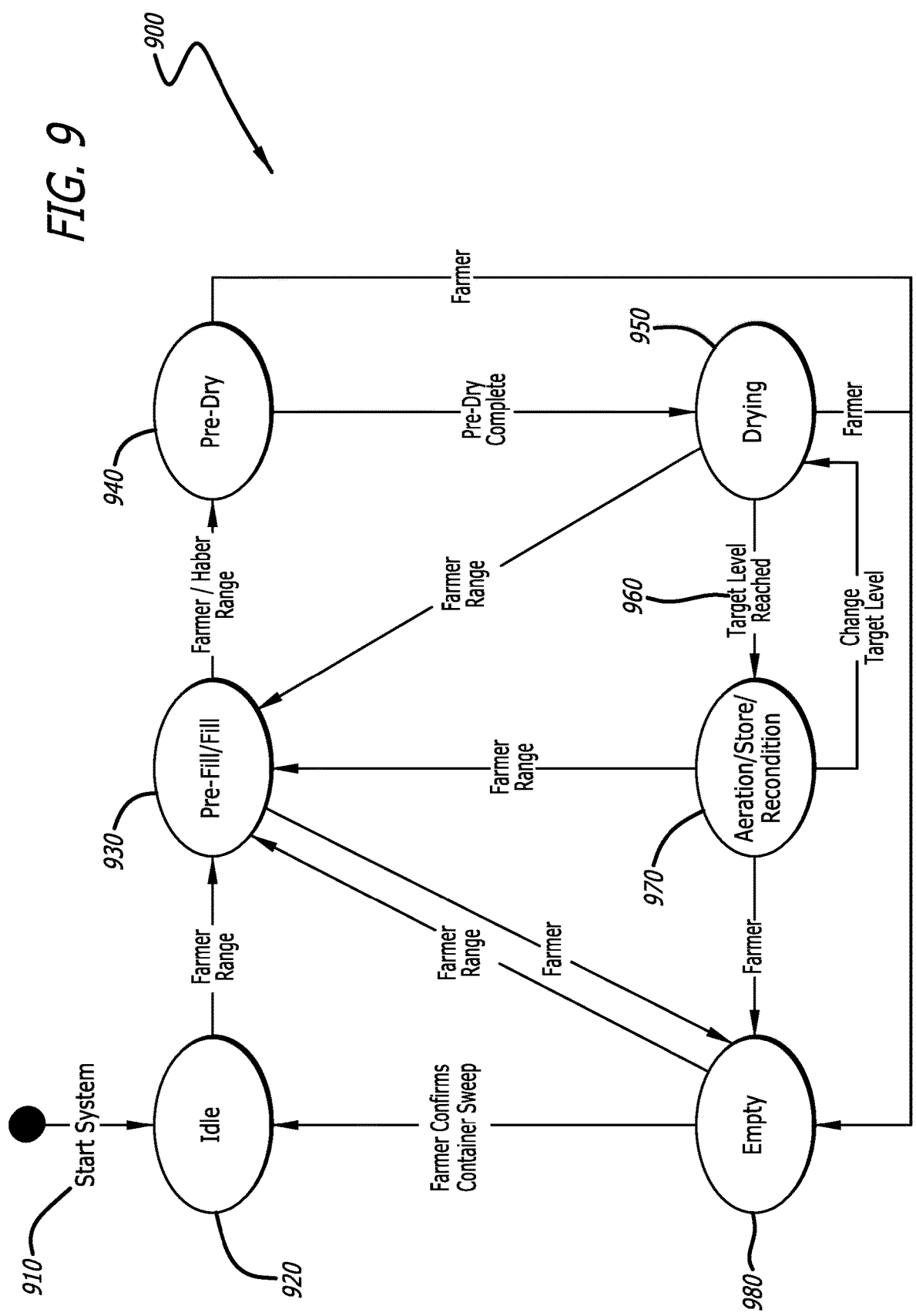
FIG. 9 is a block diagram and flow chart illustrating operational modes as machine states within the post-harvest crop management platform that represent control algorithms executing such operational modes, according to a further embodiment of the present invention.

FIG. 9 is a machine state diagram that illustrates a system 900 of operational modes as machine states within the post-harvest crop management platform 100. These machine states represent the cycles performed by executing the control algorithms 164 for such operational modes, according to a further embodiment of the present invention. The system 900 has, as a starting element, a start system state 910, at a time period zero at which the system 900 remains in an idle state 920. The system 900 begins a fill mode 930, which may be initiated by farmer or other user, for example using a ranging system such as sonar or LiDAR that indicates that filling or loading equipment is approaching, or in position at, a container 102 (or provided as a user input 115). The system 900 then cycles through a pre-dry mode 940 and one or more pre-drying cycles 166, and when that mode is complete, a drying mode 950 and one or more drying cycles 167 are performed. When a target moisture content 960 is reached, indicated by a user input 115 as a desired crop characteristic level 117, an aeration/storage/re-conditioning mode 970, performed in one or more aeration cycles 168, is initiated. The system 900 may continue to invoke the drying mode 950 where the desired crop characteristic level 117 changes over time. When the aeration/storage/re-conditioning mode 970 has completed, and the container 102 is emptied, the system 900 enters an empty state 980, and when the user or farmer confirms the empty state 980 with a bin sweep, returns to the idle state 920.

It should be noted that the system 900 may return to fill mode 930, from any of the drying modes 950, aeration/storage/re-conditioning modes 970, or empty states 980, for example where the system 900 detects that a filling or loading operation has commenced. This may occur, for example and as noted above, using a LiDAR ranging system that indicates that filling or loading equipment is approaching, or in position at, a container 102, or provided by user input 115.

Figure 10A:
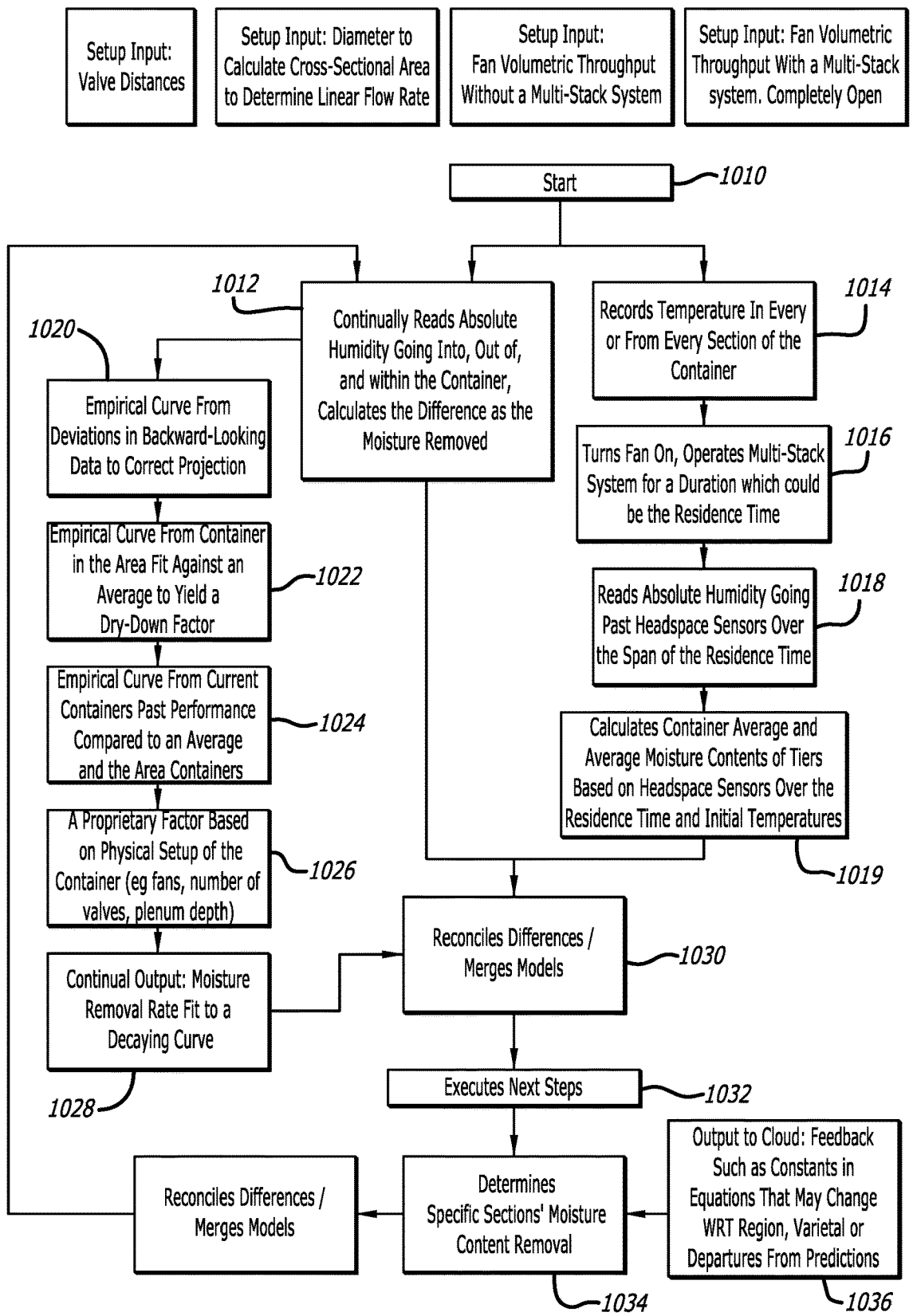
FIGS. 10A-10D are block diagrams and flow charts illustrating analytics performed within the post-harvest crop management platform of the present invention and performance of quality and value analyses as specific functions thereof.

FIGS. 10A-10D are block diagrams and flow charts illustrating analytics performed within the post-harvest crop management platform 100 of the present invention and performance of quality and value analyses as specific functions thereof. FIG. 10A illustrates a quality and value analysis 1000 for assessing performance of the post-harvest crop management platform 100 and the multi-stack assembly 106, in which initializing inputs 1002 that represent lag-time values, container characteristics 104, fan volumetric throughput with no multi-stack assembly 106 installed, and fan volumetric throughput with the multi-stack assembly 106 installed and are provided. The quality and value analysis 1000 may execute one or more algorithms designed to analyze sensor data 114 and model different crop characteristics within container 102 based on different types of such sensor data 114, such as for example a relative humidity model and a temperature model as discussed below.

The quality and value analysis 1000 begins at block 1010, and proceeds with reading relative humidity going into and out of the container 102 at block 1012 representing the relative humidity model, and recording temperature values at every section of the container 102 at block 1014, representing the temperature model. The temperature model operates the multi-stack assembly 106 at block 1016 and records sensor readings of absolute humidity for effluent passing headspace sensors at block 1018, and calculates bin average and average moisture content 1019 based on absolute humidity readings from sensors 130 in the headspace and on initial temperature values. The relative humidity model performs multiple steps that include analyzing empirical curves from deviations in backward-looking data at block 1020, analyzing empirical curves from bins in the same geographical area, fit against a yield average of other bins to a dry-down factor at block 1022, and analyzing empirical curves from the current bin's past performance compared to other bin averages and bins from the same geographical area at block 1024. The relative humidity model also evaluates the physical set up of the container 102 at block 1026, and continually outputs a moisture removal rate that is fit to a decaying curve, to yield an expected dry-down rate at block 1028.

The outcomes of the relative humidity model and a temperature model are merged, and differences reconciled, at block 1030, and the modeling framework performs the next steps in the post-harvest crop management platform 100 at block 1032. The quality and value analysis 1000 then uses lag time and values taken from headspace sensors to determine moisture content removal for specific sections of a container 102 at block 1034, and outputs feedback at block 1036 that may, for example, suggest adjustments to, or new values for, constants in equations that may change with respect to varietal, region or type/brand of container 102, or departures from predictions previously made in the post-harvest crop management platform 100.

Figure 10B:
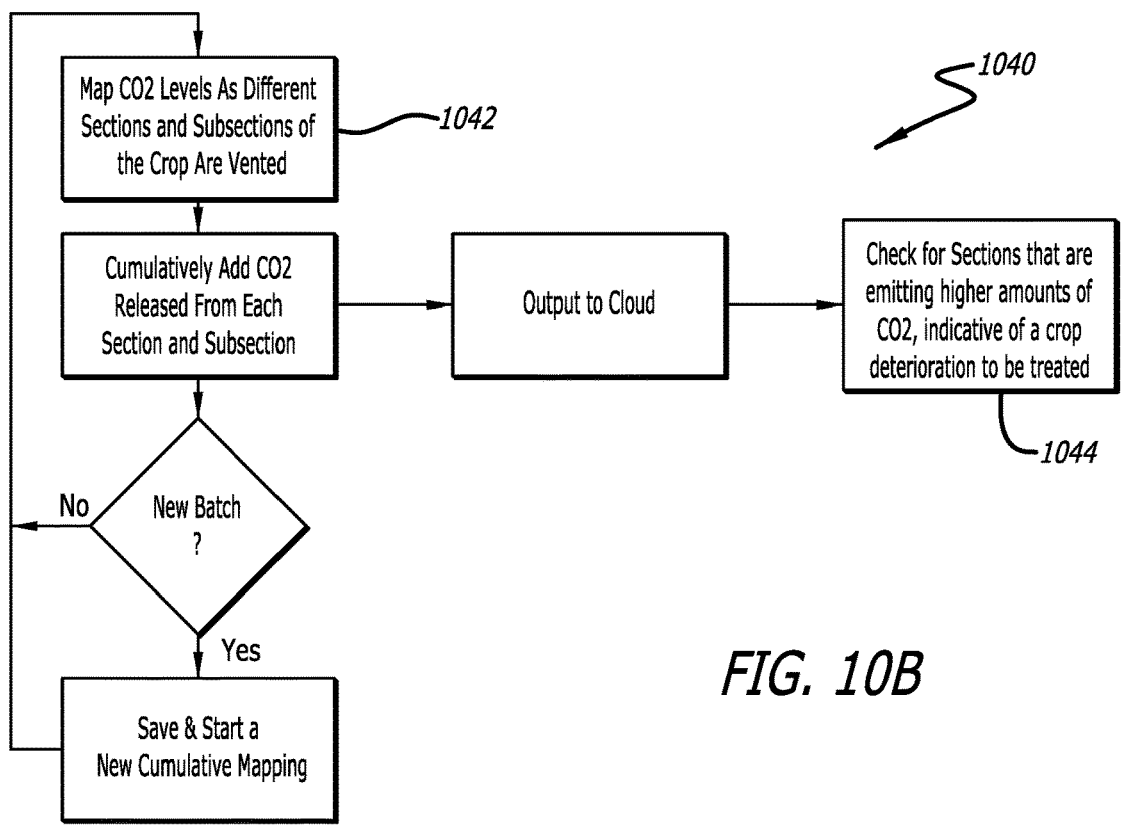
Figure 10C:
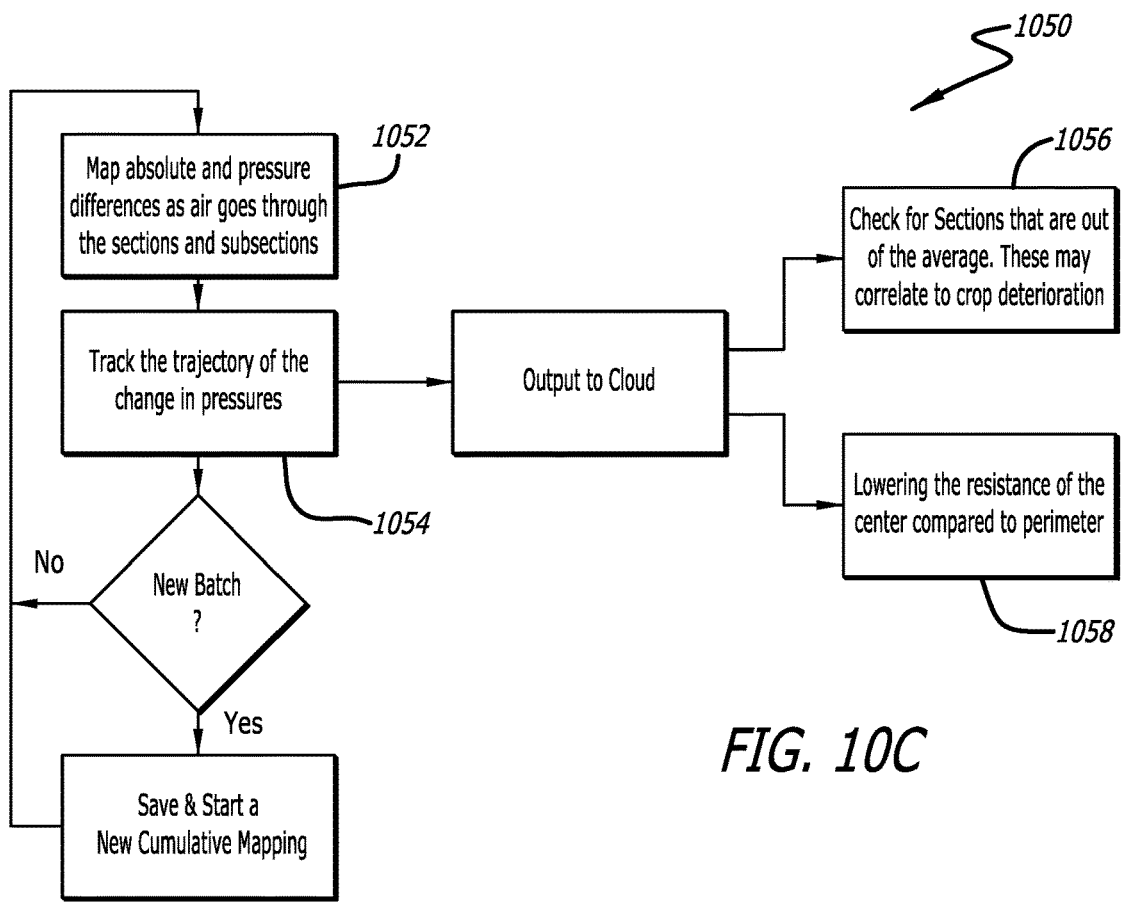

FIGS. 10B and 10C illustrate further embodiments of quality and value analyses 1040 and 1050, respectively, for assessing performance of the post-harvest crop management platform 100 and the multi-stack assembly 106. The quality and value analysis 1040 of FIG. 10B performs an analysis of the crop 120 based on readings of $CO_2$ sensors 134, and maps $CO_2$ off-gassing rates as different sections and subsections of bins are vented, as in block 1042. The quality and value analysis 1040 of FIG. 10B performs checks for, and provides output data 190 representing, sections of the crop 120 that are emitting higher amounts of $CO_2$ and therefore an indication of a crop deterioration to be treated (for example, a presence of insects giving off high levels of $CO_2$) within the container 102, at block 1044.

Figure 10D:
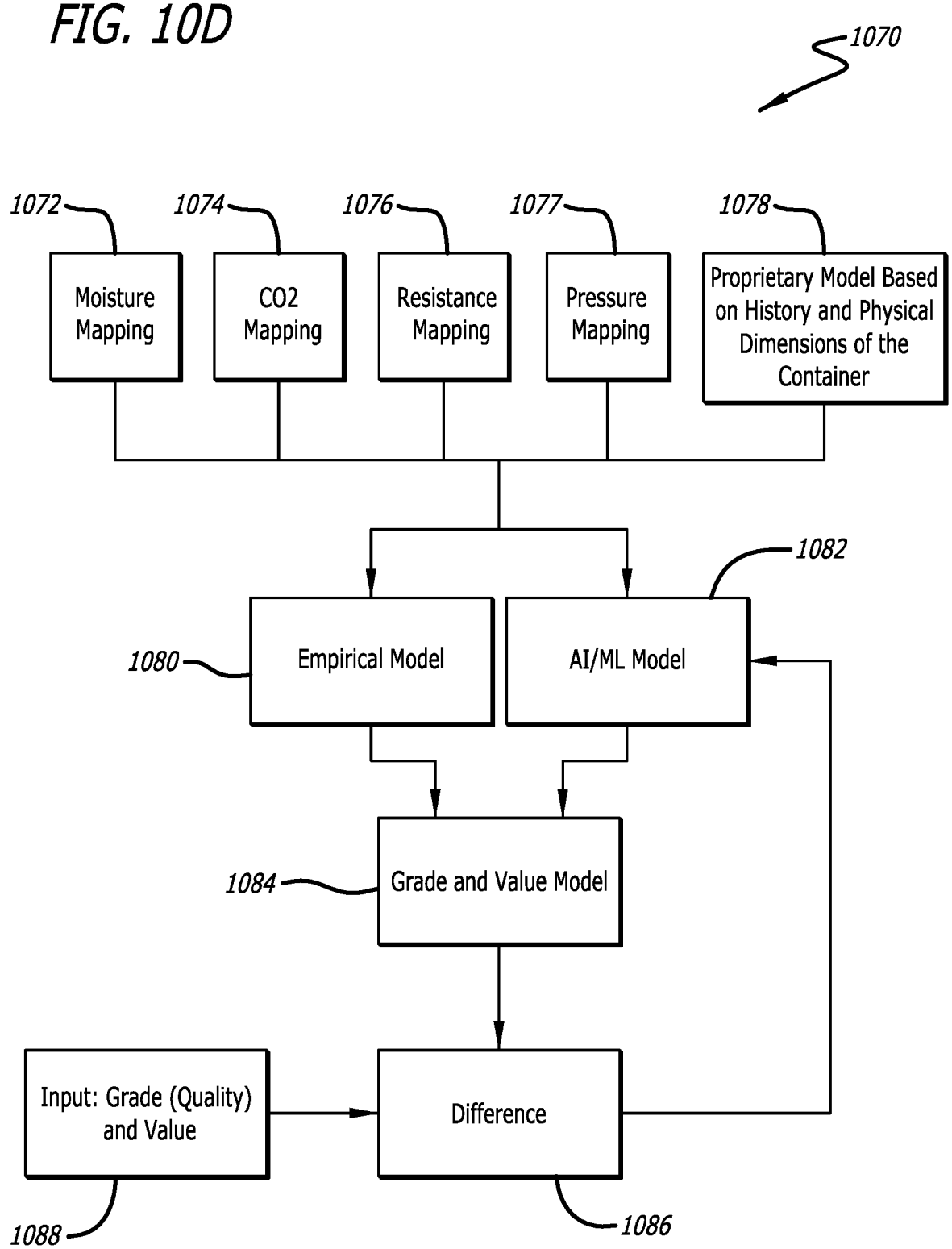

The quality and value analysis 1050 of FIG. 10C performs an analysis of the crop 120 based on absolute pressure and pressure differences as air goes through the sections and subsections of the crop 120 in container 102, as indicated by pressure sensors 133, and maps pressure at different sections and subsections of the crop 120, as in block 1052. At block 1054, the quality and value analysis 1050 tracks a trajectory of the change in pressure(s), and provides output data 190 at block 1056 representing sections of the crop 120 that are outside of expected averages and which may correlate to deterioration within the crop 120, and at block 1058, a value representing a lowering of the resistance of the center of the crop 120 as compared to a perimeter of the crop 120 within a container 102 due to differences in pressure. FIG. 10D illustrates a further quality and value analysis 1070 that combines moisture mapping 1072, $CO_2$ mapping 1074, resistance mapping 176, a pressuring mapping 1077, and a proprietary model 1078 based on historical performance of, and physical dimensions of, a container 102. The further quality and value analysis 1070 of FIG. 10D models these four elements in both an empirical model 1080 and an artificial intelligence-based model 1082, and combines the outputs from these models into a grade and value model 1084. The further quality and value analysis 1070 then generates differences 1086 between the empirical model 1080 and the artificial intelligence-based model 1082, and returns the difference to the artificial intelligence-based model 1082. The inputs 1088 for defining the differences 1086 may include grade, or quality, of the crop 120, or value.

Figure 11A:
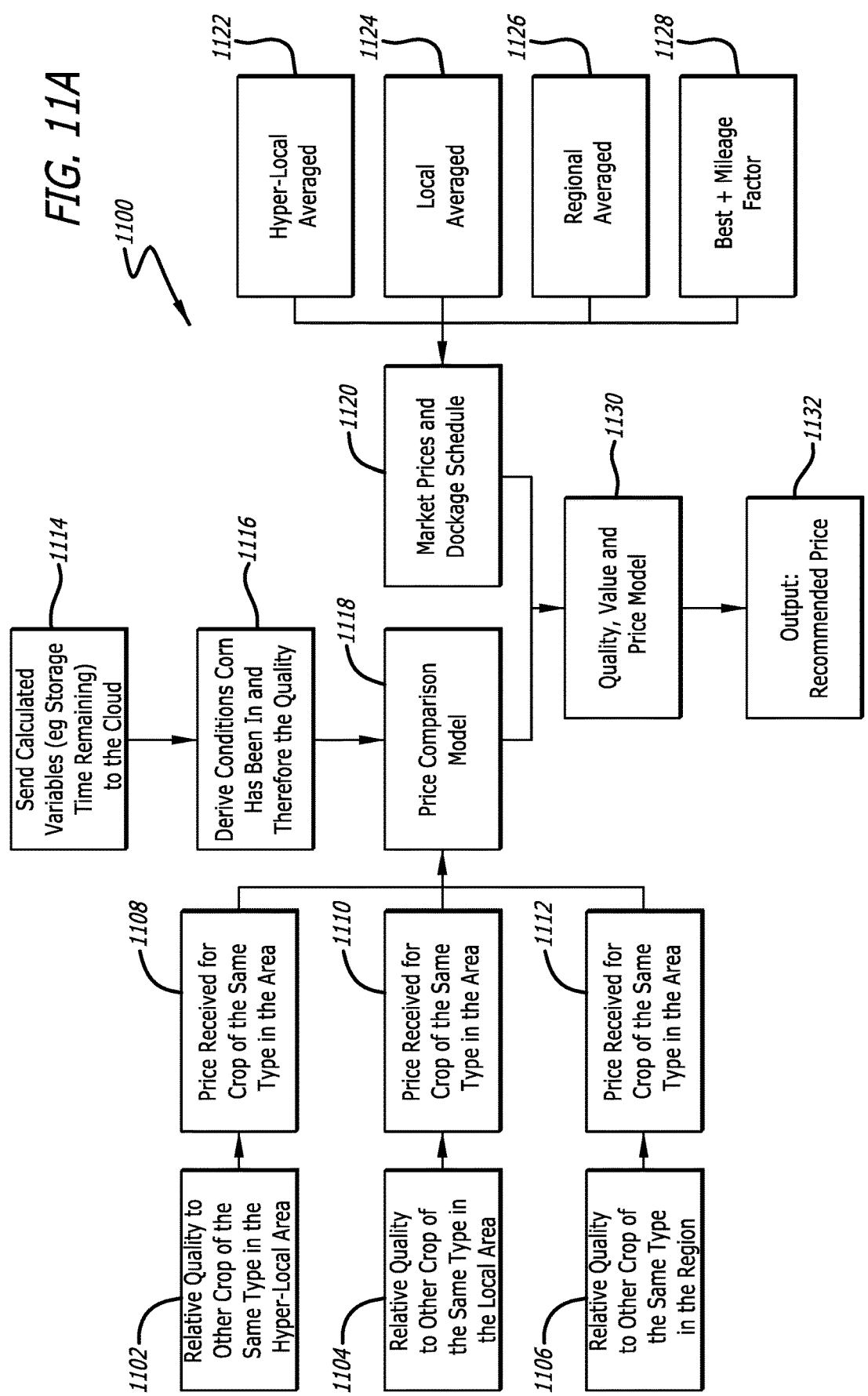
FIGS. 11A-11B are block diagrams and flow charts illustrating analytics performed within the post-harvest crop management platform of the present invention and performance of price estimation and bin checks as output use cases thereof.
Figure 11B:
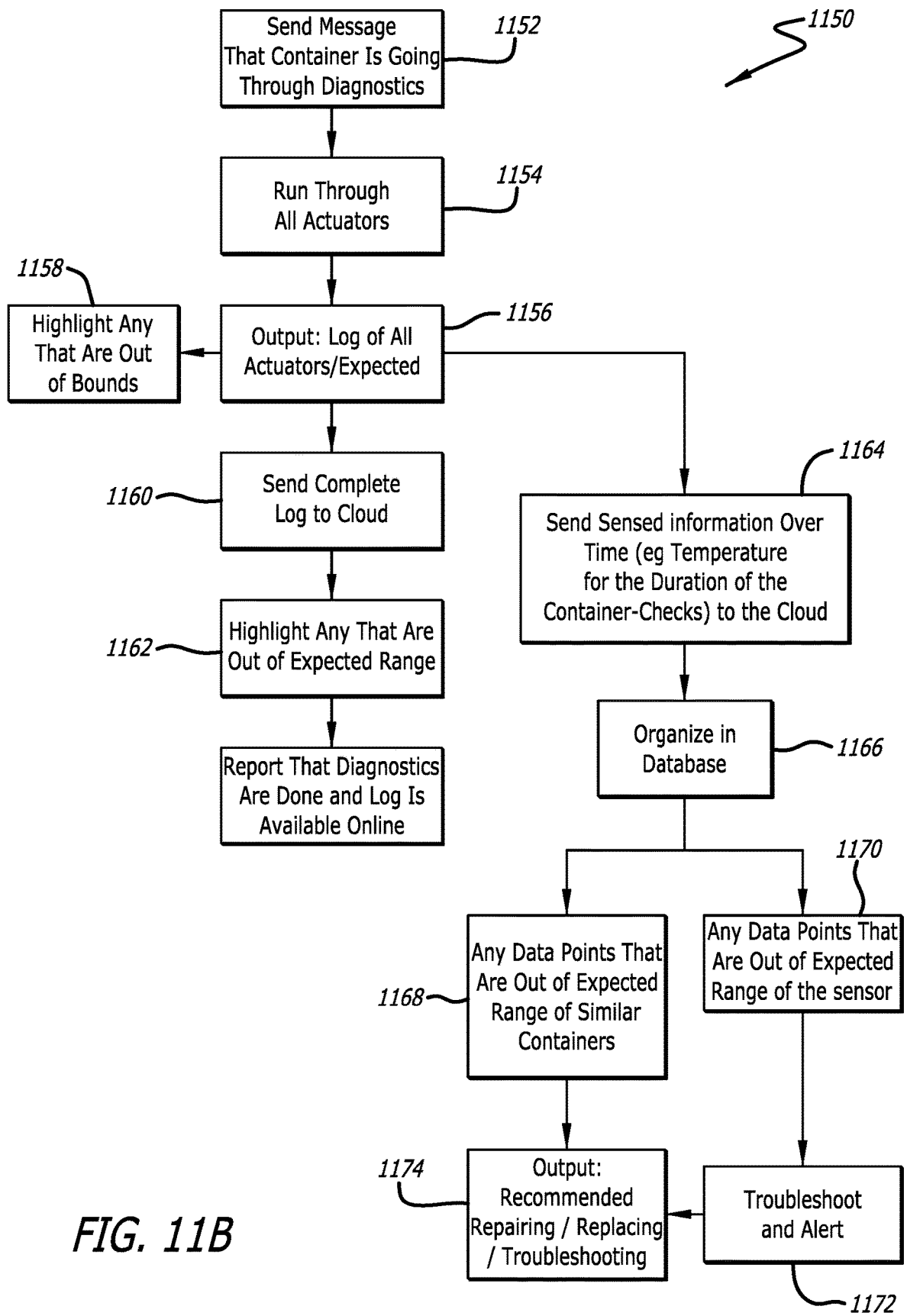

FIG. 11A-11B are block diagrams and flow charts illustrating additional analytics performed within the post-harvest crop management platform 100 of the present invention. FIG. 11A illustrates a price estimation analysis 1100, and FIG. 11B illustrates a bin check function 1150. Each of these may be performed as output use cases of the post-harvest crop management platform 100.

The price estimation analysis 1100 of FIG. 11A performs multiple assessments to arrive at a recommended price 1132. The price estimation analysis 1100 assesses relative quality to other crops of the same type in an area at block 1102, and a price received for the crop of the same type in the same area at block 1108; relative quality to other crops of the same type in a local area at block 1104, and a price received for the crop of the same type in the same local area at block 1110, and relative quality to other crops of the same type in the same region at block 1106, and a price received for the crop of the same type in the same region at block 1112. A price comparison model 1118 inputs these values, as well as other calculated variables from block 1114, and derived conditions in which the crop has been prior to storage in a container 102, as in block 1116.

The comparison model 1118 then combines all of this information with market prices and loading/unloading schedules 1120, which may have inputs for the hyper-local area 1122, local area 1124, an averaged regional area 1126, and regional area plus a mileage factor 1128, and inputs these values into a quality, value, and price model 1130. The price estimation analysis 1100 then generates the recommended price 1132 for the crop 120.

The bin check function 1150 of FIG. 11B begins with a message 1152 that a container 102 is undergoing a diagnostic function, and then runs through all actuators at 1154 for the multi-stack assembly 106 to assess bin conditions. The bin check function 1150 logs values representing all actuators at block 1156, and highlights 1158 any values that are outside expected values. The bin check function 1150 also sends a complete log 1160 to a cloud computing environment, and highlights 1162 any values that are outside of a range. Sensed information recorded over time, for example the temperature recorded during the entire bin check, is sent at block 1164 to the cloud computing environment, organized in a database at block 1166, and any data points either outside of the 3-sigma range 1168 or outside of any other expected range 1170 are recorded. The bin check function 1150 then initiates a troubleshoot or alert message 1172 for any such data points, and generates a recommendation 1174 for repair, replacement, or troubleshooting. Any valves in the multi-stack assembly that are not functioning properly are provided as inputs for analysis of the fluid modeling element 160 to automatically correct for any components that are not working correctly in the event that a repair or replacement has not been made.

FIG. 12 illustrates analytics performed within the post-harvest crop management platform 100 of the present invention, and specifically a weather analysis 1200 for generation of weather recommendations in an output use-case thereof. The weather analysis 1200 incorporates geographic data for short term weather forecasts 1210, geographic data for long term weather forecasts 1212, and geographic data for localized weather 1214 collected from the container 102 or containers that are near to that of the container 102 being analyzed. Added to these inputs are data from previous years' dry down rates 1216, to correct expected dry down rate, geographic data to obtain local dry down rates 1218, data from previous years for the same container 102 and local containers 1220, and a proprietary factor 1222 based on a physical setup of the container 102 (such as the number fans, number of valves, and plenum depth) as well as based on conditions related to the crop (such as growing conditions—precipitation patterns, growing degree days, maximum temperatures, frost dates compared to crop maturity, and varietal).

All of this data is input to a model 1224, which assumes that the crop 120 is ready for harvesting. Additionally, the model 1224 may accept a user input 115 as to a drying strategy and sell date 1226, and proprietary factors or weights that represent weather conditions 1225. Otherwise, the model generates a drying strategy to meet the sell-by date. The weather analysis 1200 then adds cumulative drying power available 1228, and allows a further user input 115 allowing for a manual adjustment 1230 of the moisture content, for example each day and based on user observations. Regardless, the weather analysis 1200 then generates a recommendation for harvest of a crop 120 based on weather, either as aggressive 1232 (for example by ranking of days based on absolute humidity), moderate 1234 (for example synching a harvest recommendation based on pre-set threshold temperature over a period of time), or conservative 1236 (alerting for warm, low humidity days, followed by one preset time period below a threshold temperature value). Another strategy may encompass a maximum storage time by selecting a timeframe with the maximum expected drying capacity, supplementing up to a certain point with heat, then only drying during relatively cool periods to quickly dry the crop down with heat to an acceptable level then allow for maximum storage time by only drying the crop with air that is relatively cool but has an acceptable drying capacity, which may or may not be supplemented with heat (for example, selecting a cool night with relatively dry air but supplementing with very little heat to increase the drying capacity).

API Elements

Access to the post-harvest crop management platform 100 of the present invention may be provided through one or more application programming interfaces (APIs). The present invention contemplates that many layers of APIs may be utilized within the post-harvest crop management platform 100, for example to enable ingestion of particular forms of input data 110, or customized uses of the output data 190. One layer of APIs may be utilized to connect feeds of input data 110 with the post-harvest crop management platform 100 itself, and different APIs may be provided for each type of input data 110, for example where different types of input data 110 have different formats and content, or are ingested from different sources. APIs may be managed by an API element specifically configured for each implementation thereof, for example as a specific sub-element of the data collection element 146 for intake of certain types of information that require a particular format or conversion from a particular format, and the data collection element 142 may itself be thought of as a layer of APIs configured to ingest input data 110.

A further layer of APIs may be utilized to ingest certain information for specific portions of the machine learning modeling engine 170. For example, the data collection element 142 may retrieve historical information via an API that provides this information directly to the processing performed by one or more neural networks 176, and extracts information from such historical data for further analytics in the various data processing elements 144 of the post-harvest crop management platform 100.

APIs may also be utilized to enable messaging within the post-harvest crop management platform 100, for example to communicate real-time operational messages or status messages. APIs may also be utilized for monitoring of activities occurring during performance of expert control algorithms 164 and/or during actuation of a multi-stack assembly 182, and for creating and displaying dashboards of information, for example of an operational status.

A further layer of APIs may be provided for output data 190. One or more APIs may be developed to enable the follow-on forms of the output data 190 that are discussed above. Third parties, for example, may utilize such APIs to develop their own, follow-on uses of the output data 190, such as to generate and export customized reports, comply with regulatory requirements, generate recommendations, risk assessments, or alerts, or develop their own enterprise-specific applications. APIs may also be provided to enable customized interfaces via the support tool 148.

Other Embodiments in Autonomous Field Activities

As noted above, the post-harvest crop management platform 100 of the present invention may be considered as an element within the broader farming ecosystem that easily integrates with multiple other elements that together comprise autonomous field and farm activities and operations. Therefore, although embodiments discussed here are generally more focused on what is happening within a container 102 than any other part of the farming ecosystem or beyond (e.g., shipping container), many other implementations of the present invention are possible.

For example, the post-harvest crop management platform 100 may integrate with farm equipment and hardware and software implements thereon (such as for example tractors, sprayers, combines, grain carts or trucks, drones, irrigation systems, etc.) to collect data that is relevant to the modeling framework for regulating selected crop characteristic 116, such as for example information related to crop type 121, planting dates 123, harvest dates 125, crop readiness, in-field crop moisture levels, nutrient applications, field and soil conditions, and any other information collected by such equipment.

The post-harvest crop management platform 100 may also integrate with container loading and unloading equipment. For example, during loading of a container 102, the post-harvest crop management platform 100 may be configured to generate and transmit one or more signals or instructions 191 as part of output data 190, such as a start/stop signal to a truck or a wet holding container, a signal to turn on or turn off or slow down or speed up a conveyor system for filling the container known as an auger, a signal relative to the amount of crop in a container 102 (which by way of further example may be used to market that space is available for rent in a particular container), or conversely, a signal comprising an alert when a container 102 is full. The post-harvest crop management platform 100 may also integrate with systems operating the loading equipment, by, for example, aerating the then-top section(s) only while the loading equipment returns to the field for fresh grain.

The post-harvest crop management platform 100 may also integrate with other systems by communicating an in-progress crop drying status to other equipment, for example to transfer a crop 120 (such using a "leg" (a bucket elevator or some other type of elevator and conveyor system) to fill peripheral or satellite containers, or temporary trucks/piles that have different drying capabilities to ensure that the desired crop characteristic level 117 is achieved in the desired temporal windows.

The post-harvest crop management platform 100 may also integrate with other systems by monitoring in-bin conditions or conditions within the multiple sections of the crop 120 to identify price signals, for example so that a recommendation or alert 192 may be generated for a farmer, grower, or manager when a desired crop characteristic level 117 is within a specified range (or when an anticipated price for the crop 120 is within a specified range), which may further be used to communicate an instruction 191 or signal for unloading equipment. Still further, the post-harvest crop management platform 100 may also integrate with other systems to clean out the container (for example, the aeration floor), by communicating an instruction 191 and/or signal to automatically start/stop a cleanout auger located in the aeration floor, to automatically run a sweep auger, to automatically raising or lowering stacks to let the sweep auger pass, and to run a pneumatic vibrator to clean off the walls and stacks. Such an instruction 191 and/or signal may further be applied to coordinate with cleanout equipment, for example to order another cleanout truck when one the cleanout truck is full.

Aspects of the present specification may also be described by the following embodiments:

1. A method, comprising:
receiving, as input data, information collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container;
analyzing the input data in a plurality of data processing elements within a computing environment that includes one or more processors and at least one computer-readable non-transitory storage medium having program instructions stored therein which, when executed by the one or more processors, cause the one or more processors to execute the plurality of data processing elements to regulate a selected crop characteristic in the multiple sections of the crop with a multi-stack assembly comprised of a plurality of stacks positioned within the container by:
    sampling conditions of the crop, by measuring at least one of relative humidity taken of effluent within the container or measuring temperature of the crop at each section, and identifying one or more parameters to achieve a desired crop characteristic level in the crop based on at least the measured relative humidity or the measured temperature,
    calculating values for the selected crop characteristic for each section of the crop to create a sampling matrix representing a profile of the selected crop characteristic across the multiple sections of the crop in the container,
    generating one or more inputs for a mass model configured to analyze one or more mass flows across the multiple sections of the crop from the sampling matrix, and
    determining an application of one or more fluid flow patterns to each section of the crop based on the one or more mass flows, to determine at least one sequence of fluid flow for the multiple sections of the crop to achieve the desired crop characteristic level; and
actuating the multi-stack assembly to apply the at least one sequence of fluid flow to achieve the desired crop characteristic level across at least one section of the crop.

2. The method of claim 1, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

3. The method of claim 1, further comprising mapping the selected crop characteristic based on the sampling matrix, wherein the selected crop characteristic is one or more of moisture content of the crop, a temperature of the crop, a pressure of the crop, and an off-gassing of carbon dioxide in the crop.

4. The method of claim 1, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

5. The method of claim 1, wherein the mass model configured to analyze one or more mass flows across the multiple sections of the crop from the sampling matrix feeds a block-oriented model that includes one or more dynamic blocks representing the drying parameters.

6. The method of claim 5, wherein outputs of dynamic blocks in the block-oriented model, and empirical data from actual drying processes performed in the crop, are applied to automatically calculate and update drying parameters in one or more neural networks that are inputs for the mass model.

7. The method of claim 1, wherein the application of the one or more fluid flow patterns is executed by a plurality of algorithms that are configured to perform at least one of:
  preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop,
  pre-drying the crop to reduce a resistance of one or more of the sections of the crop, including a core section of the crop, and a top section of the crop to the fluid flow,
  drying the crop to change the selected crop characteristic to the desired crop characteristic level for the multiple sections of the crop,
  aerating the crop when the selected crop characteristic reaches the desired crop characteristic level to equalize and maintain the desired crop characteristic level across each section of the crop within the container, and
  reconditioning the crop from crop characteristics for storage or transport of the crop, to crop characteristics desired for market placement before the crop is removed from the container to maximize a value of the crop.

8. The method of claim 7, wherein the system check protocol includes at least one of calibration of the multi-stack assembly, calibration of one or more of the sensors, and self-healing of the multi-stack assembly, and self-healing of the one or more sensors.

9. The method of claim 1, wherein the application of the one or more fluid flow patterns comprises directing at least one of ambient air, heated air, cooled air, ethylene, nitrogen, and suspended particles or chemicals to the crop to regulate the selected crop characteristic.

10. The method of claim 1, wherein the input data further comprises meteorological information that includes one or both of historical field-level weather data and extended-range weather forecast data for a geographical position where the container is located.

11. A system for regulating a selected crop characteristic in multiple sections of a crop within a container, comprising:
a data collection element configured to receive input data comprised of information collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container;
a crop characteristic and fluid flow modeling element configured, within a computing environment that includes one or more processors and at least one computer-readable non-transitory storage medium having program instructions stored therein which, when executed by the one or more processors, cause the one or more processors to execute a plurality of data processing elements, to:
  sample conditions of the crop, by measuring at least one of relative humidity taken of effluent within the container or measuring temperature of the crop at each section, and identifying one or more parameters to achieve a desired crop characteristic level in the crop based on at least the measured relative humidity or the measured temperature,
  calculate values for the selected crop characteristic for each section of the container to create a sampling matrix representing a profile of the selected crop characteristic across the multiple sections of the crop in the container,
  generate one or more inputs for a mass model configured to analyze one or more mass flows across the multiple sections of the crop from the sampling matrix, and
  determine an application of one or more fluid flow patterns to each section of the crop based on the one or more mass flows, to determine at least one sequence of fluid flow for the multiple sections of the crop to achieve the desired crop characteristic level; and
a stack actuation element, configured to actuate a multi-stack assembly comprised of a plurality of stacks positioned within the container, to apply the at least one sequence of fluid flow to achieve the desired crop characteristic level across at least one section of the crop.

12. The system of claim 11, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

13. The system of claim 11, wherein the crop characteristic and fluid flow modeling element is further configured to map the selected crop characteristic based on the sampling matrix, wherein the selected crop characteristic is one or more of moisture content of the crop, a temperature of the crop, a pressure of the crop, and an off-gassing of carbon dioxide in the crop.

14. The system of claim 11, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

15. The system of claim 11, wherein the mass model configured to analyze one or more mass flows across the multiple sections of the crop from the sampling matrix feeds a block-oriented model that includes one or more dynamic blocks representing the drying parameters.

16. The system of claim 15, wherein outputs of dynamic blocks in the block-oriented model, and empirical data from actual drying processes performed in the crop, are applied to automatically calculate and update drying parameters in one or more neural networks that are inputs for the mass model.

17. The system of claim 11, wherein the application of the one or more fluid flow patterns is executed by a plurality of algorithms that are configured to perform at least one of:

preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop, pre-drying the crop to reduce a resistance of one or more of the sections of the crop, including a core section of the crop, and a top section of the crop to the fluid flow, drying the crop to change the selected crop characteristic to the desired crop characteristic level for the multiple sections of the crop, aerating the crop when the selected crop characteristic reaches the desired crop characteristic level to equalize and maintain the desired crop characteristic level across each section of the crop within the container, and reconditioning the crop from crop characteristics for storage or transport of the crop, to crop characteristics desired for market placement before the crop is removed from the container to maximize a value of the crop.

18. The system of claim 17, wherein the system check protocol includes at least one of calibration of the multi-stack assembly, calibration of one or more of the sensors, and self-healing of the multi-stack assembly, and self-healing of the one or more sensors.

19. The system of claim 11, wherein the application of the one or more fluid flow patterns comprises directing at least one of ambient air, heated air, cooled air, ethylene, nitrogen, and suspended particles or chemicals to the crop to regulate the selected crop characteristic.

20. The system of claim 11, wherein the input data further comprises meteorological information that includes one or both of historical field-level weather data and extended-range weather forecast data for a geographical position where the container is located.

21. A method, comprising:

within a computing environment that includes one or more processors and at least one computer-readable non-transitory storage medium having program instructions stored therein which, when executed by the one or more processors, cause the one or more processors to execute a plurality of data processing elements for performing functions comprised of:

modeling an application of one or more fluid flow patterns to multiple sections of a crop within a container, by analyzing input data collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container, to develop a profile of a selected crop characteristic across the multiple sections of the crop, by measuring at least one of relative humidity taken of effluent within the container or measuring temperature of the crop at each section, and identifying one or more parameters to achieve a desired crop characteristic level in the crop based on at least the measured relative humidity or the measured temperature, creating a sampling matrix representing a profile of the selected crop characteristic across the multiple sections of the crop in the container, by calculating values for the selected crop characteristic for each section of the crop, configuring a mass model to analyze one or more mass flows across the multiple sections of the crop, having one or more inputs generated from the sampling matrix, and applying the mass model to identify one or more fluid flow patterns for application to each section of the crop based on one or more mass flows, and determine at least one sequence of fluid flow for the multiple sections of the crop to achieve the desired crop characteristic level; and regulating the selected crop characteristic level in an application of the at least one sequence of fluid flow to achieve the desired crop characteristic level across at least one section of the crop, by actuating a multi-stack assembly comprised of at least one stack positioned within the container.

22. The method of claim 21, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

23. The method of claim 21, wherein the modeling the application of the one or more fluid flow patterns to the multiple sections of the crop further comprises mapping the selected crop characteristic based on the sampling matrix, wherein the selected crop characteristic is one or more of moisture content of the crop, a temperature of the crop, a pressure of the crop, and an off-gassing of carbon dioxide in the crop.

24. The method of claim 21, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

25. The method of claim 21, wherein the mass model feeds a block-oriented model that includes one or more dynamic blocks representing the drying parameters.

26. The method of claim 25, wherein outputs of dynamic blocks in the block-oriented model, and empirical data from actual drying processes performed in the crop, are applied to automatically calculate and update drying parameters in one or more neural networks that are inputs for the mass model.

27. The method of claim 21, wherein the one or more fluid flow patterns for application to each section of the crop are executed by a plurality of algorithms that are configured to perform at least one of:

preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop, pre-drying the crop to reduce a resistance of one or more of the sections of the crop, including a core section of the crop, and a top section of the crop to the fluid flow, drying the crop to change the selected crop characteristic to the desired crop characteristic level for the multiple sections of the crop, aerating the crop when the selected crop characteristic reaches the desired crop characteristic level to equalize and maintain the desired crop characteristic level across each section of the crop within the container, and reconditioning the crop from crop characteristics for storage or transport of the crop, to crop characteristics desired for market placement before the crop is removed from the container to maximize a value of the crop.

28. The method of claim 27, wherein the system check protocol includes at least one of calibration of the multi-stack assembly, calibration of one or more of the sensors, and self-healing of the multi-stack assembly, and self-healing of the one or more sensors.

29. The method of claim 21, wherein the regulating the selected crop characteristic level further comprises directing at least one of ambient air, heated air, cooled air, ethylene, nitrogen, and suspended particles or chemicals to the crop to regulate the selected crop characteristic.

30. The method of claim 21, wherein the input data further comprises meteorological information that includes one or both of historical field-level weather data and extended-range weather forecast data for a geographical position where the container is located.

The systems and methods of the present invention may be implemented in many different computing environments 140. For example, the various algorithms embodied in the data processing elements 144 may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, GPU and any comparable means. Still further, the present invention may be implemented in cloud-based data processing environments, and where one or more types of servers are used to process large amounts of data, and using processing components such as CPUs (central processing units), GPUs (graphics processing units), TPUs (tensor processing units), and other similar hardware. In general, any means of implementing the methodology illustrated herein can be used to implement the various aspects of the present invention. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors or general processing units), memory, nonvolatile storage, input devices, and output devices. Furthermore, alternative software implementations including, but not limited to, distributed processing, parallel processing, or virtual machine processing can also be configured to perform the methods described herein.

The systems and methods of the present invention may also be wholly or partially implemented in software that can be stored on a non-transitory computer-readable storage medium, executed on programmed general-purpose computer with the cooperation of a controller and memory, a special purpose computer, a microprocessor, or the like. In these instances, the systems and methods of this invention can be implemented as a program embedded on a mobile device or personal computer through such mediums as an applet, JAVA® or CGI script, as a resource residing on one or more servers or computer workstations, as a routine embedded in a dedicated measurement system, system component, or the like. The system can also be implemented by physically incorporating the system and/or method into a software and/or hardware system.

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, machine learning, artificial intelligence, fuzzy logic, expert system or combination of hardware and software that is capable of performing the data processing functionality described herein.

The foregoing descriptions of embodiments of the present invention have been presented for the purposes of illustration and description. It is not intended to be exhaustive or to limit the invention to the precise forms disclosed. Accordingly, many alterations, modifications and variations are possible in light of the above teachings, may be made by those having ordinary skill in the art without departing from the spirit and scope of the invention. For example, the post-harvest crop management platform may be provided as a stand-alone software application or as software-as-a-service, independent of any hardware system. Alternatively, the post-harvest crop management platform may be implemented in conjunction with specific hardware systems, such as the multi-stack assembly 106, but it is to be understood that the post-harvest crop management platform is agnostic of any particular hardware, and therefore may be implemented with any type of hardware, regardless of the configuration of the assembly or assemblies comprising such hardware. It is therefore intended that the scope of the invention be limited not by this detailed description. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. A method, comprising:
    receiving, as input data, information collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container;
    analyzing the input data in a plurality of data processing elements within a computing environment that includes one or more processors and at least one computer-readable non-transitory storage medium having program instructions stored therein which, when executed by the one or more processors, cause the one or more processors to execute the plurality of data processing elements to regulate a selected crop characteristic in the multiple sections of the crop with a multi-stack assembly comprised of a plurality of stacks disposed between a top of the container and a bottom of the container and positioned within the multiple sections of the crop throughout the container and configured to transfer at least one sequence of fluid flow to and from the multiple sections of the crop throughout the container, by:
        sampling conditions of the crop, by measuring at least one of relative humidity taken of effluent in at least one section of the crop within the container or measuring temperature of the crop at each section, to achieve a desired crop characteristic level in a specific section of the crop based on at least the measured relative humidity or the measured temperature,
        calculating values for the selected crop characteristic for each section of the crop to create a sampling matrix representing a profile of the selected crop characteristic across each of the multiple sections of the crop in the container, generating one or more inputs for a mass model configured to analyze one or more mass flows across each of the multiple sections of the crop that flow into the plurality of stacks from the sampling matrix, and
        determining an application of one or more targeted fluid flow patterns through the plurality of stacks to each desired section of the crop based on the one or more mass flows, to determine the at least one sequence of fluid flow from the plurality of stacks to the multiple sections of the crop to achieve the desired crop characteristic level without moving the crop within the multiple sections; and
    actuating the multi-stack assembly to apply the at least one sequence of fluid flow to achieve the desired crop characteristic level in at least one section of the crop while one or both of an amount or position of the crop within the multiple sections remains constant.

2. The method of claim 1, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

3. The method of claim 1, further comprising mapping the selected crop characteristic based on the sampling matrix, wherein the selected crop characteristic is a pressure of the crop within the container, and adjusting the one or more targeted fluid flow patterns to deliver the at least one sequence of fluid flow to a section of the crop where a disparity in pressure is detected.

4. The method of claim 1, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

5. The method of claim 1, wherein the mass model configured to analyze one or more mass flows across the multiple sections of the crop from the sampling matrix feeds a larger block-oriented model that includes one or more dynamic blocks representing drying parameters obtained from the multiple sections of the crop, wherein the one or more dynamic blocks are adjusted in real time as the drying parameters are obtained.

6. The method of claim 5, wherein outputs of dynamic blocks in the block-oriented model, and empirical data from actual drying processes performed in the crop, are applied to automatically calculate and update drying parameters in one or more neural networks in real time that act as dynamic inputs for the mass model.

7. The method of claim 1, wherein the application of the one or more fluid flow patterns is executed by a plurality of algorithms that are configured to perform at least one of:
    preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop,
    pre-drying the crop to reduce a resistance of one or more of the sections of the crop, including a core section of the crop, and a top section of the crop to the fluid flow,
    drying the crop by altering the specific flow patterns based on selected crop characteristics to achieve the desired crop characteristic for the multiple sections of the crop,
    aerating the crop when the selected crop characteristic reaches the desired crop characteristic level to equalize and maintain the desired crop characteristic level across each section of the crop within the container, and
    reconditioning the crop from crop characteristics for storage or transport of the crop, to crop characteristics desired for market placement before the crop is removed from the container to maximize a value of the crop.

8. The method of claim 7, wherein the system check protocol includes at least one of calibration of the multi-stack assembly, calibration of one or more of the sensors, and self-healing of the multi-stack assembly, and self-healing of the one or more sensors.

9. The method of claim 1, wherein the application of the one or more fluid flow patterns comprises directing at least one of ambient air, heated air, cooled air, ethylene, nitrogen, and suspended particles or chemicals to the crop to regulate the selected crop characteristic.

10. The method of claim 1, wherein the input data further comprises meteorological information that includes one or both of historical field-level weather data and extended-range weather forecast data for a geographical position where the container is located.

11. A system for regulating a selected crop characteristic in multiple sections of a crop within a container, comprising:
a data collection element configured to receive input data comprised of information collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container;
a crop characteristic and fluid flow modeling element configured, within a computing environment that includes one or more processors and at least one computer-readable non-transitory storage medium having program instructions stored therein which,
when executed by the one or more processors, cause the one or more processors to execute a plurality of data processing elements, to:
sample conditions of the crop, by measuring at least one of relative humidity taken of effluent in at least one section of the crop within the container or measuring temperature of the crop at each section, to achieve a desired crop characteristic level in a specific section of the crop based on at least the measured relative humidity or the measured temperature,
calculate values for the selected crop characteristic for each section of the container to create a sampling matrix representing a profile of the selected crop characteristic across each of the multiple sections of the crop in the container,
generate one or more inputs for a mass model configured to analyze one or more mass flows across each of the multiple sections of the crop that flow into a plurality of stacks comprising a multi-stack assembly from the sampling matrix, and
determine an application of one or more targeted fluid flow patterns through the plurality of stacks to each desired section of the crop based on the one or more mass flows, to determine at least one sequence of fluid flow from the plurality of stacks to the multiple sections of the crop to achieve the desired crop characteristic level without moving the crop within the multiple sections; and
a stack actuation element, configured to actuate the plurality of stacks comprising the multi-stack assembly, the plurality of stacks disposed between a top of the container and a bottom of the container and positioned within the multiple sections of the crop throughout the container and configured to transfer the at least one sequence of the fluid flow to and from the multiple sections of the crop throughout the container, achieve the desired crop characteristic level in at least one section of the crop while one or both of an amount or position of the crop within the multiple sections remains constant.

12. The system of claim 11, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

13. The system of claim 11, wherein the crop characteristic and fluid flow modeling element is further configured to map the selected crop characteristic based on the sampling matrix, wherein the selected crop characteristic is a pressure of the crop within the container, and adjusting the one or more targeted fluid flow patterns to deliver the at least one sequence of fluid flow to a section of the crop where a disparity in pressure is detected.

14. The system of claim 11, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

15. The system of claim 11, wherein the mass model configured to analyze one or more mass flows across the multiple sections of the crop from the sampling matrix feeds a larger block-oriented model that includes one or more dynamic blocks representing drying parameters obtained from the multiple sections of the crop, wherein the one or more dynamic blocks are adjusted in real time as the drying parameters are obtained.

16. The system of claim 15, wherein outputs of dynamic blocks in the block-oriented model, and empirical data from actual drying processes performed in the crop, are applied to automatically calculate and update drying parameters in one or more neural networks in real time that act as dynamic inputs for the mass model.

17. The system of claim 11, wherein the application of the one or more fluid flow patterns is executed by a plurality of algorithms that are configured to perform at least one of:
preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop,
pre-drying the crop to reduce a resistance of one or more of the sections of the crop, including a core section of the crop, and a top section of the crop to the fluid flow,
drying the crop by altering the specific flow patterns based on selected crop characteristics to achieve the desired crop characteristic for the multiple sections of the crop,
aerating the crop when the selected crop characteristic reaches the desired crop characteristic level to equalize and maintain the desired crop characteristic level across each section of the crop within the container, and
reconditioning the crop from crop characteristics for storage or transport of the crop, to crop characteristics desired for market placement before the crop is removed from the container to maximize a value of the crop.

18. The system of claim 17, wherein the system check protocol includes at least one of calibration of the multi-stack assembly, calibration of one or more of the sensors, and self-healing of the multi-stack assembly, and self-healing of the one or more sensors.

19. The system of claim 11, wherein the application of the one or more fluid flow patterns comprises directing at least one of ambient air, heated air, cooled air, ethylene, nitrogen, and suspended particles or chemicals to the crop to regulate the selected crop characteristic.

20. The system of claim 11, wherein the input data further comprises meteorological information that includes one or both of historical field-level weather data and extended-range weather forecast data for a geographical position where the container is located.

21. A method, comprising:
within a computing environment that includes one or more processors and at least one computer-readable non-transitory storage medium having program instructions stored therein which, when executed by the one or more processors, cause the one or more processors to execute a plurality of data processing elements for performing functions comprised of:
modeling an application of one or more fluid flow patterns to multiple sections of a crop within a container, by analyzing input data collected from a plurality of sensors that are either positioned proximate to, or embedded within, a crop and inside or proximate to a container containing the crop, the plurality of sensors at least including sensors configured to sense at least one of a relative humidity and a temperature at multiple sections of the crop within the container, to develop a profile of a selected crop characteristic across the multiple sections of the crop, by
measuring at least one of relative humidity taken of effluent in at least one section of the crop within the container or measuring temperature of the crop at each section, to achieve a desired crop characteristic level a specific section of in the crop based on at least the measured relative humidity or the measured temperature,
creating a sampling matrix representing a profile of the selected crop characteristic across each of the multiple sections of the crop in the container, by calculating values for the selected crop characteristic for each section of the crop,
configuring a mass model to analyze one or more mass flows across each of the multiple sections of the crop that flow into a plurality of stacks comprising a multi-stack assembly, having one or more inputs generated from the sampling matrix, and
applying the mass model to identify one or more targeted fluid flow patterns through the plurality of stacks for application to each desired section of the crop based on one or more mass flows, and determine at least one sequence of fluid flow from the plurality of stacks to the multiple sections of the crop to achieve the desired crop characteristic level without moving the crop within the multiple sections; and
regulating the selected crop characteristic level in an application of the at least one sequence of fluid flow to achieve the desired crop characteristic level in at least one section of the crop while one or both of an amount or position of the crop within the multiple sections remains constant, by actuating at least one stack of the plurality of stacks comprising the multi-stack assembly, the plurality of stacks disposed between a top of the container and a bottom of the container and positioned within the multiple sections of the crop throughout the container and configured to transfer the at least one sequence of the fluid flow to and from the multiple sections of the crop throughout the container.

22. The method of claim 21, wherein the input data further includes one or more user inputs relative to the crop, the one or more user inputs including an initial moisture content value comprising an anticipated starting crop characteristic level, a storage moisture content value comprising a less perishable crop characteristic level, a market moisture content value comprising a crop characteristic level fit for sale, a crop harvest date, and an anticipated crop sell date defining a temporal limit on the storage of the crop beyond the crop harvest date.

23. The method of claim 21, wherein the modeling the application of the one or more fluid flow patterns to the multiple sections of the crop further comprises mapping the selected crop characteristic based on the sampling matrix, wherein the selected crop characteristic is a pressure of the crop within the container, and adjusting the one or more targeted fluid flow patterns to deliver the at least one sequence of fluid flow to a section of the crop where a disparity in pressure is detected.

24. The method of claim 21, wherein the fluid flow is directed to the crop from one or more valve assemblies positioned in at least one stack, each valve assembly comprised of at least one gate and at least one vent, wherein exhaust intervals and plume intervals are achieved by selectively opening and closing the at least one gate and the at least one vent at each vent assembly at the at least one stack.

25. The method of claim 21, wherein the mass model feeds a larger block-oriented model that includes one or more dynamic blocks representing drying parameters obtained from the multiple sections of the crop, wherein the one or more dynamic blocks are adjusted in real time as the drying parameters are obtained.

26. The method of claim 25, wherein outputs of dynamic blocks in the block-oriented model, and empirical data from actual drying processes performed in the crop, are applied to automatically calculate and update drying parameters in one or more neural networks in real time that act as dynamic inputs for the mass model.

27. The method of claim 21, wherein the one or more fluid flow patterns for application to each section of the crop are executed by a plurality of algorithms that are configured to perform at least one of:

preparing the container for filling with the crop by performing at least one of a system-check protocol, opening and closing vent and gate assemblies of the multi-stack assembly to check functionality and blow out debris, raising and lowering the stacks in response to a sweep auger, and cleaning out a plenum chamber to enable fluid delivery through a plenum to the crop, pre-drying the crop to reduce a resistance of one or more of the sections of the crop, including a core section of the crop, and a top section of the crop to the fluid flow, drying the crop by altering the specific flow patterns based on selected crop characteristics to achieve the desired crop characteristic for the multiple sections of the crop, aerating the crop when the selected crop characteristic reaches the desired crop characteristic level to equalize and maintain the desired crop characteristic level across each section of the crop within the container, and reconditioning the crop from crop characteristics for storage or transport of the crop, to crop characteristics desired for market placement before the crop is removed from the container to maximize a value of the crop.

28. The method of claim 27, wherein the system check protocol includes at least one of calibration of the multi-stack assembly, calibration of one or more of the sensors, and self-healing of the multi-stack assembly, and self-healing of the one or more sensors.

29. The method of claim 21, wherein the regulating the selected crop characteristic level further comprises directing at least one of ambient air, heated air, cooled air, ethylene, nitrogen, and suspended particles or chemicals to the crop to regulate the selected crop characteristic.

30. The method of claim 21, wherein the input data further comprises meteorological information that includes one or both of historical field-level weather data and extended-range weather forecast data for a geographical position where the container is located.

\* \* \* \* \*